United States Patent
Leonhardt et al.

(10) Patent No.: US 10,208,084 B2
(45) Date of Patent: Feb. 19, 2019

(54) MEANS AND METHODS FOR SITE-SPECIFIC FUNCTIONALIZATION OF POLYPEPTIDES

(71) Applicants: LUDWIG-MAXIMILIANS-UNIVERSITÄT MÜNCHEN, Munich (DE); FORSCHUNGSVERBUND BERLIN E.V., Berlin (DE)

(72) Inventors: Heinrich Leonhardt, Munich (DE); Jonas Helma, Munich (DE); Dominik Schumacher, Berlin (DE); Christian Hackenberger, Berlin (DE)

(73) Assignees: LUDWIG-MAXIMILIANS-UNIVERSITÄT MÜNCHEN, Munich (DE); FORSCHUNGSVERBUND BERLIN E.V., Berlin (DE)

( * ) Notice: Subject to any disclaimer, the term of this patent is extended or adjusted under 35 U.S.C. 154(b) by 0 days.

(21) Appl. No.: 15/521,675

(22) PCT Filed: Oct. 29, 2015

(86) PCT No.: PCT/EP2015/075130
§ 371 (c)(1),
(2) Date: Apr. 25, 2017

(87) PCT Pub. No.: WO2016/066749
PCT Pub. Date: May 6, 2016

(65) Prior Publication Data
US 2017/0349625 A1 Dec. 7, 2017

(30) Foreign Application Priority Data

Oct. 29, 2014 (LU) .......................................... 92588
Jun. 18, 2015 (EP) .................................... 15172797

(51) Int. Cl.
*C12P 21/00* (2006.01)
*C07K 1/107* (2006.01)
*C12P 21/02* (2006.01)

(52) U.S. Cl.
CPC .......... *C07K 1/1075* (2013.01); *C12P 21/005* (2013.01); *C12P 21/02* (2013.01); *C12Y 603/02025* (2013.01)

(58) Field of Classification Search
None
See application file for complete search history.

(56) References Cited

FOREIGN PATENT DOCUMENTS

WO 2013/003555 A1 1/2013
WO 2015/041729 A2 3/2015

OTHER PUBLICATIONS

M. Rudiger et al., "The carboxy-terminal peptide of detyrosinated alpha tubulin provides a minimal system to study the substrate specificity of tubulin-tyrosine kinase", European Journal of Biochemistry, vol. 220, No. 2, 1994, pp. 309-320, XP002741133, Wiley-Blackwell Publishing Ltd. ISSN: 0014-2956.
A. E. Prota et al., "Structural basis of tubulin tyrosination by tuibulin tyrosine ligase", The Journal of Cell Biology : JCB, vol. 200, No. 3, Jan. 28, 2013, pp. 259-270, XP002741134, The Rockefeller University Press ISSN: 0021-9525.
H.M. Kalisz et al., "Incorporation of nitrotyrosine into alpha-tubulin by recombinant mammalian tubulin-tyrosine ligase", Biochimica et Biophysica ACTA., vol. 1481, No. 1, 2000, pp. 131-138, XP004287993, Elsevier, ISSN: 0006-3002.
A. Banerjee et al., "Site-specific orthogonal labeling of the carboxy-terminus of tubulin", Acs Chemical Biology, vol. 5, No. 8, 2010, pp. 777-785, XP002753023, American Chemical Society, Washington, DC ISSN: 1554-8929.
D. Schumacher et al., "Versatile and efficient site-specific protein functionalization by tubulin tyrosine ligase", Angewandte Chemie International Edition, vol. 54, 2015, pp. 13787-13791, XP002753024, Wiley—VCH Verlag GmbH & Co. KGaA, ISSN: 1433-7851.
PCT International Search Report dated Jan. 26, 2016 from corresponding Application No. PCT/EP2015/075130.
Hackenberger et al., Angew. Chem. Int. Ed. 2008, 47, 10030-10074.
Arce et al., Eur. J. Biochem. 59, 145-149 (1975).
Szyk et al., Nature Structural & Molecular Biology (2011) 18(11): 1250-1259.
Pall et al., Fungal Genetics Newsletter (1991) 40: 59-61.
Keppler et al., A general method for the covalent labeling of fusion proteins with small molecules in vivo. Nature Biotechnology 21, 86-89, doi:10.1038/nbt765 (2003).
Los et al., HaloTag: a novel protein labeling technology for cell imaging and proteinanalysis. Acs Chem Biol 3, 373-382, doi:10.1021/cb800025k (2008).
Schumacher et al., More than add-on: chemoselective reactions for the synthesis of functional peptides and proteins. Current opinion in chemical biology 22, 62-69, doi:10.1016/j.cbpa.2014.09.018 (2014).
Liebscher et al., N-terminal protein modification by substrate-activated reverse proteolysis. Angewandte Chemie International Edition 53, 3024-3028, doi:10.1002/anie.201307736 (2014).
Mao et al., Sortase-mediated protein ligation: a new method for protein engineering. Journal of the American Chemical Society 126, 2670-2671, doi:10.1021/ja039915e (2004).
Yin et al., Genetically encoded short peptide tag for versatile protein labeling by Sfp phosphopantetheinyl transferase. Proceedings of the National Academy of Sciences of the United States of America 102, 15815-15820, doi:10.1073/pnas.0507705102 (2005).
Chen et al., Site-specific labeling of cell surface proteins with biophysical probes using biotin ligase. Nature methods 2, 99-104, doi:10.1038/nmeth735 (2005).
Fernandez-Suarez et al., Redirecting lipoic acid ligase for cell surface protein labeling with small-molecule probes. Nature Biotechnology 25, 1483-1487, doi:10.1038/nbt1355 (2007).

(Continued)

*Primary Examiner* — Jeanette M Lieb
(74) *Attorney, Agent, or Firm* — Dilworth IP, LLC

(57) ABSTRACT

The present invention provides means and methods for equipping a polypeptide of interest at its C-terminus with a versatile adaptor amino acid that allows the functionalization of the polypeptide of interest.

31 Claims, 27 Drawing Sheets

Specification includes a Sequence Listing.

(56) References Cited

OTHER PUBLICATIONS

Wu et al., Site-specific chemical modification of recombinant proteins produced in mammalian cells by using the genetically encoded aldehyde tag. Proceedings of the National Academy of Sciences of the United States of America 106, 3000-3005, doi:10.1073/pnas.0807820106 (2009).
Hamers-Casterman et al., Naturally occurring antibodies devoid of light chains. Nature 363, 446-448, doi:10.1038/363446a0 (1993).
Trinkle-Mulcahy et al., Identifying specific protein interaction partners using quantitative mass spectrometry and bead proteomes. J Cell Biol 183, 223-239, doi:10.1083/jcb.200805092 (2008).
Rothbauer et al., Targeting and tracing antigens in live cells with fluorescent nanobodies. Nature Methods 3, 887-889, doi:Doi 10.1038/Nmeth953 (2006).
Kirchhofer et al. Modulation of protein properties in living cells using nanobodies. Nat Struct Mol Biol 17, 133-138, doi:10.1038/nsmb.1727 (2010).
Agard et al., A strain-promoted [3+2] azide-alkyne cycloaddition for covalent modification of biomolecules in living systems. Journal of the American Chemical Society 126, 15046-15047, doi:10.1021/ja044996f (2004).
Saxon et al., Cell surface engineering by a modified Staudinger reaction. Science 287, 2007-2010 (2000).
Serwa et al., Site-specific PEGylation of proteins by a Staudinger-phosphite reaction. Chem Sci 1, 596-602, doi:Doi 10.1039/C0sc00324g (2010).
Sletten et al., Bioorthogonal chemistry: fishing for selectivity in a sea of functionality. Angewandte Chemie International Edition 48, 6974-6998, doi:10.1002/anie.200900942 (2009).
Guizetti et al., Cortical constriction during abscission involves helices of ESCRT-III-dependent filaments. Science 331, 1616-1620, doi:science.1201847 [pii] 10.1126/science.1201847 (2011).
Ries et al., A simple, versatile method for GFP-based super-resolution microscopy via nanobodies. Nat Methods 9, 582-584, doi:nmeth.1991 [pii] 10.1038/nmeth.1991 (2012).
Zink et al., Tubulin detyrosination promotes monolayer formation and apical trafficking in epithelial cells. J Cell Sci 125, 5998-6008, doi:10.1242/jcs.109470 (2012).
Patel et al., Biotechnology Letters 25: 331-334, 2003, Kluwer Acadamic Publishers.
Sambrook et al., Molecular Cloning: A Laboratory Manual, 4th edition (date), Chapter 19, "Choosing an appropriate expression vector", pp. 1488-1493, Cold Spring Harbor Laboratory Press.

SEQUENCE LISTING

<160> NUMBER OF SEQ ID NOS: 12

<210> SEQ ID NO 1
<211> LENGTH: 450
<212> TYPE: PRT
<213> ORGANISM: Homo sapiens

<400> SEQUENCE: 1

Met Arg Glu Cys Ile Ser Ile His Val Gly Gln Ala Gly Val Gln Ile

-continued

```
1               5                   10                  15
Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Asp Asp Ser
            35                  40                  45

Phe Asn Thr Phe Phe Ser Glu Thr Gly Ala Gly Lys His Val Pro Arg
50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
            115                 120                 125

Cys Thr Gly Leu Gln Gly Phe Leu Val Phe His Ser Phe Gly Gly Gly
130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
            195                 200                 205

Ile Tyr Asp Ile Cys Arg Arg Asn Leu Asp Ile Glu Arg Pro Thr Tyr
210                 215                 220

Thr Asn Leu Asn Arg Leu Ile Gly Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
            275                 280                 285

Ala Glu Ile Thr Asn Ala Cys Phe Glu Pro Ala Asn Gln Met Val Lys
            290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Thr Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
            355                 360                 365

Ala Lys Val Gln Arg Ala Val Cys Met Leu Ser Asn Thr Thr Ala Ile
            370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430
```

```
Glu Glu Val Gly Val Asp Ser Val Glu Gly Glu Gly Glu Glu Glu Gly
        435                 440                 445

Glu Glu
    450
```

<210> SEQ ID NO 2
<211> LENGTH: 4
<212> TYPE: PRT
<213> ORGANISM: artificial
<220> FEATURE:
<223> OTHER INFORMATION: TTL recognition sequence

<400> SEQUENCE: 2

```
Glu Gly Glu Glu
1
```

<210> SEQ ID NO 3
<211> LENGTH: 14
<212> TYPE: PRT
<213> ORGANISM: artificial
<220> FEATURE:
<223> OTHER INFORMATION: TTL recognition sequence

<400> SEQUENCE: 3

```
Val Asp Ser Val Glu Gly Glu Gly Glu Glu Glu Gly Glu Glu
1               5                   10
```

<210> SEQ ID NO 4
<211> LENGTH: 12
<212> TYPE: PRT
<213> ORGANISM: artificial
<220> FEATURE:
<223> OTHER INFORMATION: TTL recognition sequence

<400> SEQUENCE: 4

```
Ser Val Glu Gly Glu Gly Glu Glu Gly Glu Glu
1               5                   10
```

<210> SEQ ID NO 5
<211> LENGTH: 10
<212> TYPE: PRT
<213> ORGANISM: artificial
<220> FEATURE:
<223> OTHER INFORMATION: TTL recognition sequence

<400> SEQUENCE: 5

```
Ser Ala Asp Gly Glu Asp Glu Gly Glu Glu
1               5                   10
```

<210> SEQ ID NO 6
<211> LENGTH: 11
<212> TYPE: PRT
<213> ORGANISM: artificial
<220> FEATURE:
<223> OTHER INFORMATION: TTL recognition sequence

<400> SEQUENCE: 6

```
Ser Val Glu Ala Glu Ala Glu Glu Gly Glu Glu
1               5                   10
```

<210> SEQ ID NO 7
<211> LENGTH: 10
<212> TYPE: PRT
<213> ORGANISM: artificial
<220> FEATURE:
<223> OTHER INFORMATION: TTL recognition sequence

```
<400> SEQUENCE: 7

Ser Tyr Glu Asp Glu Asp Glu Gly Glu Glu
1               5                   10

<210> SEQ ID NO 8
<211> LENGTH: 10
<212> TYPE: PRT
<213> ORGANISM: artificial
<220> FEATURE:
<223> OTHER INFORMATION: TTL recognition sequence

<400> SEQUENCE: 8

Ser Phe Glu Glu Glu Asn Glu Gly Glu Glu
1               5                   10

<210> SEQ ID NO 9
<211> LENGTH: 58
<212> TYPE: DNA
<213> ORGANISM: artificial
<220> FEATURE:
<223> OTHER INFORMATION: synthetic primer sequence for TTL recognitioon
      sequence

<400> SEQUENCE: 9
ggggccatgg cccatcatca ccatcaccat gatgtgcagc tgcaggagtc tgggggag          58

<210> SEQ ID NO 10
<211> LENGTH: 71
<212> TYPE: DNA
<213> ORGANISM: artificial
<220> FEATURE:
<223> OTHER INFORMATION: synthetic primer sequence for TTL recognition
      sequence

<400> SEQUENCE: 10
ccccgaattc ttattcttcg ccttcttctt cgccttcgcc ttccacgcta tccactgagg          60
agacggtgac c                                                              71

<210> SEQ ID NO 11
<211> LENGTH: 4
<212> TYPE: PRT
<213> ORGANISM: artificial
<220> FEATURE:
<223> OTHER INFORMATION: TTL recognition sequence
<220> FEATURE:
<221> NAME/KEY: misc
<222> LOCATION: (1)..(1)
<223> OTHER INFORMATION: X can be any amino acid
<220> FEATURE:
<221> NAME/KEY: misc
<222> LOCATION: (2)..(2)
<223> OTHER INFORMATION: X can be any amino acid
<220> FEATURE:
<221> NAME/KEY: misc
<222> LOCATION: (3)..(3)
<223> OTHER INFORMATION: X can be E, D or C
<220> FEATURE:
<221> NAME/KEY: misc
<222> LOCATION: (4)..(4)
<223> OTHER INFORMATION: X can be E

<400> SEQUENCE: 11

Xaa Xaa Xaa Xaa
1

<210> SEQ ID NO 12
<211> LENGTH: 377
```

<212> TYPE: PRT
<213> ORGANISM: Homo sapiens

<400> SEQUENCE: 12

```
Met Tyr Thr Phe Val Val Arg Asp Glu Asn Ser Ser Val Tyr Ala Glu
1               5                   10                  15

Val Ser Arg Leu Leu Leu Ala Thr Gly His Trp Lys Arg Leu Arg Arg
            20                  25                  30

Asp Asn Pro Arg Phe Asn Leu Met Leu Gly Glu Arg Asn Arg Leu Pro
        35                  40                  45

Phe Gly Arg Leu Gly His Glu Pro Gly Leu Val Gln Leu Val Asn Tyr
    50                  55                  60

Tyr Arg Gly Ala Asp Lys Leu Cys Arg Lys Ala Ser Leu Val Lys Leu
65                  70                  75                  80

Ile Lys Thr Ser Pro Glu Leu Ala Glu Ser Cys Thr Trp Phe Pro Glu
                85                  90                  95

Ser Tyr Val Ile Tyr Pro Thr Asn Leu Lys Thr Pro Val Ala Pro Ala
            100                 105                 110

Gln Asn Gly Ile Gln Pro Pro Ile Ser Asn Ser Arg Thr Asp Glu Arg
        115                 120                 125

Glu Phe Phe Leu Ala Ser Tyr Asn Arg Lys Lys Glu Asp Gly Glu Gly
    130                 135                 140

Asn Val Trp Ile Ala Lys Ser Ser Ala Gly Ala Lys Gly Glu Gly Ile
145                 150                 155                 160

Leu Ile Ser Ser Glu Ala Ser Glu Leu Leu Asp Phe Ile Asp Asn Gln
                165                 170                 175

Gly Gln Val His Val Ile Gln Lys Tyr Leu Glu His Pro Leu Leu Leu
            180                 185                 190

Glu Pro Gly His Arg Lys Phe Asp Ile Arg Ser Trp Val Leu Val Asp
        195                 200                 205

His Gln Tyr Asn Ile Tyr Leu Tyr Arg Glu Gly Val Leu Arg Thr Ala
    210                 215                 220

Ser Glu Pro Tyr His Val Asp Asn Phe Gln Asp Lys Thr Cys His Leu
225                 230                 235                 240

Thr Asn His Cys Ile Gln Lys Glu Tyr Ser Lys Asn Tyr Gly Lys Tyr
                245                 250                 255

Glu Glu Gly Asn Glu Met Phe Phe Lys Glu Phe Asn Gln Tyr Leu Thr
            260                 265                 270

Ser Ala Leu Asn Ile Thr Leu Glu Ser Ser Ile Leu Leu Gln Ile Lys
        275                 280                 285

His Ile Ile Arg Asn Cys Leu Leu Ser Val Glu Pro Ala Ile Ser Thr
    290                 295                 300

Lys His Leu Pro Tyr Gln Ser Phe Gln Leu Phe Gly Phe Asp Phe Met
305                 310                 315                 320

Val Asp Glu Glu Leu Lys Val Trp Leu Ile Glu Val Asn Gly Ala Pro
                325                 330                 335

Ala Cys Ala Gln Lys Leu Tyr Ala Glu Leu Cys Gln Gly Ile Val Asp
            340                 345                 350

Ile Ala Ile Ser Ser Val Phe Pro Pro Asp Val Glu Gln Pro Gln
        355                 360                 365

Thr Gln Pro Ala Ala Phe Ile Lys Leu
370                 375
```

MEANS AND METHODS FOR SITE-SPECIFIC FUNCTIONALIZATION OF POLYPEPTIDES

BACKGROUND

Protein engineering has become a widely used tool in many areas of protein biochemistry. For example, protein fusion tags are indispensable tools used to improve recombinant protein expression yields, enable protein purification, and accelerate the characterization of protein structure and function. Solubility-enhancing tags, genetically engineered epitopes, and recombinant endoproteases have resulted in a versatile array of combinatorial elements that facilitate protein detection and purification. However, also protein modifications are of importance to study structure and function relationships.

Instead of the random labeling of amino acids, such as lysine residues, methods have been developed to (sequence) specific label proteins. Next to chemical modifications, tools to integrate new chemical groups for bioorthogonal reactions/modifications or chemoselective modifications have been applied. Alternatively, proteins can also be selectively modified by enzymes. By modifying existing amino acids or introducing non-natural amino acids, proteins can be manipulated at the single amino acid level. Several methods involving the site-specific modification of proteins have been reported in the last decade. This allows the spatial and temporal control of proteins in vivo, as well as single molecule tracking. Modifications are introduced during protein translation, as post translational modification or chemically, after protein isolation.

After translation, almost all proteins require post-translational modifications (PTMs) before becoming mature. The oxidation of cysteines is a common PTM and is important for protein folding and stability. Other PTMs increase the functional diversity of proteins by the modification of amino acids including phosphorylation, glycosylation, ubiquitination, nitrosylation, methylation, acetylation and proline cis-trans isomerization. Site-specific enzymatic PTMs are of particular interest since they can be used to manipulate and/or study proteins.

Examples for PTM are membrane associated modifications facilitated by farnesyl- and N-myristoyltransferases. In another approach the native formylglycine generating enzyme (FGE) is used to introduce formylglycine in both prokaryotes and eukaryotes. The aldehyde tagged protein can be readily functionalized with aminooxy- or hydrazide-functionalized biomolecules. Besides the modification of other proteins, some enzymes can be used for self-modification such as human O6-alkylguanine-DNA alkyl transferase (hAGT), cutinase and halo alkane dehalogenase.

A straightforward class of enzymes for modifying proteins after translation are the ligases. Biotin ligase (BirA) was shown to accept also a ketone isostere of biotin as a cofactor. Ligation of this biotin analog to proteins bearing the 15-amino-acid acceptor peptide (AP) was demonstrated in vitro and in vivo, followed by subsequent ketone-hydrazine conjugation. Second, the microbial lipoic acid ligase (LplA) was used to specifically attach an alkyl azide onto proteins with an engineered LplA acceptor peptide (LAP). Another ligase is the intein-based protein ligation system. A prerequisite for this intein-mediated ligation method is that the target protein is expressed as a correctly folded fusion with the intein, which may be challenging.

Another set of post-translational modifications is performed by phosphopantetheinyl transferases (PPTases). PPTases transfer a phosphopantetheinyl (P-pant) group through a phosphodiester bond onto peptidyl/acyl carrier protein (PCP/ACP) domains. These typically 80-120 residues long domains are present on nonribosomal peptide synthetases (NRPSs), polyketide synthases (PKSs), and fatty acid synthases (FASs). Interestingly, orthogonal fluorescent labeling of cell surface receptors was demonstrated by using the PPTases Sfp and AcpS selective peptide tags.

Instead of exploring the chemical space in which biomolecules can be modified by functional groups and subsequently incorporated in proteins of interest, some general applicable enzymatic modifications preexist in nature. Transpeptidation is, for example, catalyzed by sortases, a transpeptidase from *Staphylococcus aureus*, has emerged as a general method for derivatizing proteins with various types of modifications. For conventional sortase modifications, target proteins are engineered to contain a sortase recognition motif (LPXT) near their C-termini. When incubated with synthetic peptides containing one or more N-terminal glycine residues and a recombinant sortase, these artificial sortase substrates undergo a transacylation reaction resulting in the exchange of residues C-terminal to the threonine residue with the synthetic oligoglycine peptide, resulting in the protein C-terminus being ligated to the N-terminus of the synthetic peptide (WO 2013/003555).

Other techniques for protein engineering are based on chemoselective ligation and incorporation of modified amino acid residues which may serve as joint connection for the addition of functional moieties such as drugs, dyes, etc. (Hackenberger and Schwarzer (2008), Angew. Chem. Ed. 47, 10030-10074).

Site-specific modification of proteins has emerged as powerful tool to study proteins at the single amino acid level. However, it is still challenging to engineer a protein after its translation, i.e., making post-translational modifications, since the reactions required to functionalize a translated protein, e.g. by adding a label at only one specific amino acid are oftentimes difficult, time- and material-consuming. Thus, there is still a demand for engineering a protein so as to have readily available a protein with an adaptor that allows a functionalization of said polypeptide.

The present application satisfies this demand by the provision of means and methods for equipping a protein of interest with a C-terminal adaptor amino acid which allows a functionalization of said protein as described herein below, characterized in the claims and illustrated by the appended Examples and Figures.

The inventors have unexpectedly discovered that, in contrast to the widespread prejudice in the prior art, tubulin-tyrosine ligase (TTL) is able to tyrosinate polypeptides modified to comprise a TTL-recognition sequence. In other words, the present inventors transferred action of TTL out of its context, i.e., its action on tubulin and showed that TTL is also active on heterologous substrates such as peptides or polypeptides that merely contain a TTL recognition sequence at their C-terminus, but are otherwise not structurally related to a tubulin, i.e., non-tubulin peptides or polypeptides. As explained in more detail below, the prevailing view in the prior art was that TTL merely acts on tubulin polypeptides, while the present inventors proofed much to their surprise the opposite (see Examples 8 and 8.1). TTL is active on heterologous polypeptides and equips them with a tyrosine or tyrosine derivative which acts as versatile adaptor for, e.g., moieties that functionalize a polypeptide.

It was also surprising for the present inventors to observe that within the "artificial", (i.e. non-natural environment and non-tubulin polypeptides as substrate for TTL) in which they used TTL to tyrosinate polypeptides that TTL even introduced a tyrosine derivative to the C-terminus of a polypeptide of interest, which is different from tubulin. Thus, TTL is able to incorporate a tyrosine derivative into a non-tubulin polypeptide in a non-natural environment, while it was taught in the art that TTL is strictly tubulin dependent.

Accordingly, this finding enables the attachment of a tyrosine or tyrosine derivative to a plethora of different polypeptides, and, by further addition of other moieties, opens new perspectives for research, diagnosis, and treatment. Hence, by making use the action of TTL, it is possible to functionalize a polypeptide of interest (POI), since tyrosine or a tyrosine derivative added by TTL to the C-terminus of a protein having a TTL recognition sequence allows coupling of moieties by way of a non-peptidic bond which serve, e.g. as labels, enzymes, drugs, etc. Thus, having recognized and proofed that TTL is active on heterologous substrates such as peptides or polypeptides that merely contain a TTL recognition sequence at their C-terminus, but are otherwise not structurally related to a tubulin, makes TTL a tool for equipping a POI with a tyrosine or tyrosine derivative that acts as versatile adaptor that itself is connected with moieties which functionalize a POI for, e.g. research, diagnosis, and treatment.

Tubulin-tyrosine ligase (TTL), which was first isolated from brain extracts in 1977, catalyzes the post-translational retyrosination of detyrosinated α-tubulin. It has a marked degree of sequence conservation from echinoderms to humans, and exhibits >96% identity among mammalian orthologs (Szyk, Deaconsecu and Piszczek). Remarkably, the enzyme is indispensable for cell and organism development, and TTL suppression has been linked to cell transformation and correlates with poor prognosis in patients suffering from diverse forms of cancers (Prota, Magiera and Kujpers).

In nature, TTL plays an important role in recurrent α-tubulin detyrosination/tyrosination cycles. The high substrate specificity of TTL has early been acknowledged. Even before TTL had been isolated, Arce, Hallak and Rodriguez reported in 1975 that when brain extracts are incubated with radioactive tyrosine, the label is only incorporated into a tubulin. In 1994, Rüdiger et al. assessed TTL substrate requirements by using a variety of synthetic peptides corresponding to the C-terminal sequence of α-tubulin.

Interestingly, the prejudice that αβ-tubulin or fragments thereof were the only substrate accepted by TTL for efficient tyrosination persisted in the prior art. In consequence, research on TTL activity was, in the following years, confined to assess whether TTL would accept tyrosine derivatives and attach them to the αβ-tubulin heterodimer. For example, Kalisz et al. (2000), Biochim Biophys Acta 1481: 131-138 pioneered in generating recombinant TTL in *E. coli*. The recombinant TTL exhibited similar catalytic properties as the mammalian brain tissue derived enzyme and was capable of covalently incorporating nitrotyrosine into the C-terminus of α-tubulin in vitro, albeit at 35-fold lower affinity than for tyrosine. Recently, Banerjee et al. (2010), ACS chemical biology 5: 777-785 successfully employed the TTL to conjugate a fluorescent label to αβ-tubulin. The authors developed a two step labeling systems under mild conditions and used 3-formyltyrosine as a TTL substrate and attached it to the C-terminus of a tubulin. Subsequently, 7-hydrazino-4-methyl coumarin was added by hydrazone formation to the modified tubulin as a fluorescent label under mild conditions, allowing fluorescently labeled tubulin to retain its ability to assemble into microtubules. Again, the authors here emphasize that the only TTL substrate is the C-terminus of α tubulin with the minimal requirement of EE as the last amino acids.

However, the idea to use TTL for attaching a tyrosine (or derivative thereof) to polypeptides other than tubulin did not evolve—presumably because preceding studies implied that a unique interaction between TTL and αβ-tubulin was required in order to enable tyrosination. Recently, the prejudice has been confirmed by two studies conducted by (Szyk, Deaconsecu and Piszczek) and (Prota, Magiera and Kujpers).

Szyk et al. (2011), Nature Struc Mol Biol 18(11): 1250-1259 determined the crystal structure of frog TTL. The study revealed that TTL has an elongated shape and is composed of an N-terminal domain, a central domain and a C-terminal domain, which together form the active site of the enzyme. The authors further reported that TTL recognizes tubulin by a bipartite strategy. It engages the tubulin tail through low-affinity, high-specificity interactions, and co-opts what is otherwise a homo-oligomerization interface to form a tight hetero-oligomeric complex with the tubulin body. Put it differently, Szyk et al. clearly teach that TTL is highly specific for tubulin and for its action it requires a tight interplay with tubulin.

Prota et al. (2013), J Cell Biol 200(3): 259-270 recently revealed the structural basis of TTL-tubulin interaction and tubulin tyrosination. Interestingly, based on the structural information obtained during the study, the authors conclude that a characteristic bipartite a p tubulin-TTL binding and a tubulin tail-TTL binding mode account for the high specificity of TTL for a tubulin. The authors state that the complex bipartite interaction mode observed between tubulin and TTL reveal how the enzyme has specifically evolved to recognize and modify tubulin; they virtually preclude that the enzyme modifies additional substrates.

In sum, the prior art implies that the unique interaction between TTL and its substrate αβ tubulin is an indispensable prerequisite for tyrosination. Clearly, the finding of the present invention, allowing the tyrosination by TTL of virtually any polypeptide carrying a TTL recognition motif, was unexpected. The fact that adding or introducing a TTL recognition sequence into any functional polypeptide would suffice in order to render it a suitable TTL substrate was clearly and could not be foreseen. All the more, apart from taking action on heterologous polypeptides, the fact that TTL uses in a heterologous context even tyrosine derivatives as shown by the present inventors (see Examples 5 and 8.2) could not at all have been expected and highlights the non-obviousness of the present invention.

SUMMARY

The present invention provides a method for the production of a polypeptide comprising
(a) introducing or adding at the C-terminus of a polypeptide a recognition sequence for tubulin tyrosine ligase;
(b) optionally contacting the polypeptide obtained in step (a) in the presence of tubulin tyrosine ligase and a tyrosine derivative under conditions suitable for the tubulin tyrosine ligase to tyrosinate said polypeptide with said tyrosine derivative; and
(c) optionally conjugating a moiety to said tyrosinated polypeptide obtained in step (b).

Step (c) is also envisaged to be a preferred step of the above method. Hence, in a preferred embodiment, said above method of the present invention further comprises step (c) conjugating a moiety to said tyrosinated polypeptide obtained in step (b).

The present invention also provides a polypeptide which is obtainable by the methods, particularly by said above method of the present invention. Such polypeptide obtainable by the methods of the present invention and applied therein may advantageously have a length of more than 19 amino acids and/or may be a polypeptide other than tubulin.

The present invention, as an alternative to the afore described method, provides a method for the production of a polypeptide, comprising
(a') introducing or adding at the C-terminus of a polypeptide a recognition sequence for tubulin tyrosine ligase; and
(b') contacting the polypeptide obtained in step (a') in the presence of tubulin tyrosine ligase and a tyrosine derivative conjugated to a moiety under conditions suitable for the tubulin tyrosine ligase to tyrosinate said polypeptide with said tyrosine derivative conjugated to said moiety.

The present invention also provides a polypeptide obtainable by said alternative method of the present invention. Such a polypeptide may, for example, also be tubulin, since the prior art did not provide tubulin comprising a tyrosine derivative and a further moiety, preferably a moiety as described herein.

The recognition sequence for tubulin tyrosine ligase of a polypeptide that is subjected to a method of the present invention and that may also be comprised by a polypeptide of the present invention may preferably have at least the amino acid sequence $X_1X_2X_3X_4$ (SEQ ID No: 11), wherein $X_1$ and $X_2$ is any amino acid, $X_3$ is E, D or C and $X_4$ is E. Advantageously, $X_2$ may be G, S, A, V, or F and/or $X_1$ may be E, D, A, K, or P. The recognition sequence may be EGEE (SEQ ID No. 2), VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

The polypeptide that is produced and thus obtainable by the methods of the invention may comprise a linker sequence preceding the recognition sequence of tubulin tyrosine ligase.

The moiety that may be conjugated to a tyrosinated polypeptide by way of the methods of the present invention and that may be comprised by a polypeptide of the present invention may be a carrier, a polypeptide, a detectable label, a chemical compound, a nucleic acid, a carbohydrate, or a lipid. Such a polypeptide that is conjugated to a tyrosinated polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

Suitable conditions applied in the methods for producing a polypeptide of the invention may comprise a buffer containing a nucleoside triphosphate, such as ATP, potassium chloride, magnesium chloride, a reducing agent such as DTT.

A tyrosine derivative that is applied in the methods of the invention and also comprised by a polypeptide of the invention may contain an unnatural (non-natural) functional group for a chemoselective or bioorthogonal modification however, it may alternatively contain a natural functional group for a chemoselective or bioorthogonal modification. Sometimes, when used herein, a tyrosine derivative that contains an unnatural (non-natural) functional group for a chemoselective or bioorthogonal modification is also referred to as a "click chemistry handle". This unnatural functional moiety may be selected from the group consisting of terminal alkyne, azide, strained alkyne, diene, dienophile, alkoxyamine, carbonyl, phosphine, phosphonite, phosphite, hydrazide, thiol, tetrazine, alkene, cyclooctyne, electron-withdrawing substituents such as halogens, e.g. F, Br, Cl, I, phenol-derivatives (e.g. OTs, ONs, OTf), nitriles (CN), carbonyls (CO), or nitro groups (NO2).

The tyrosine derivative applied in the methods of the invention may be substituted with the above mentioned functional groups at positions 2, 3 and 4 as well as at the benzylic position. The functional groups may be connected directly at the above mentioned positions or via a spacer, such as an alkyl spacer in between. By way of example, the tyrosine derivative may be a 3-substituted or 4-substituted tyrosine, such as 3- or 4-substituted tyrosine derivative is 3-nitrotyrosine, 3-aminotyrosine, 3-azidotyrosine, 3-formyltyrosine, 3-acetyltyrosine, or 4-aminophenylalanine.

A polypeptide that is provided herein which is, for example, obtainable by the present invention has at its C-terminus a recognition sequence for tubulin tyrosine ligase (TTL) which has preferably at least the amino acid sequence $X_4X_3X_2X_1$, wherein $X_2$ is E, D or C and $X_1$ is E. Advantageously, such a polypeptide is modified to introduce or add said recognition sequence Said polypeptide has advantageously biological activity.

$X_4$ can be E, D, A, K, or P. $X_3$ can be G, S, A, V, or F. $X_2$ may also be G, S, A, V, or F. $X_1$ may also be E, D, A, K, or P. Preferably, the recognition sequence may be EGEE (SEQ ID No. 2), VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

The polypeptide can comprise a linker sequence preceding the recognition sequence of tubulin tyrosine ligase.

In the polypeptide of the invention, a tyrosine derivative can be covalently bonded to said recognition sequence. Said tyrosine derivative may contain an unnatural (non-natural) functional group for a chemoselective or bioorthogonal modification however, it may alternatively contain a natural functional group for a chemoselective or bioorthogonal modification. This unnatural functional moiety may be selected from the group consisting of terminal alkyne, azide, strained alkyne, diene, dienophile, alkoxyamine, carbonyl, phosphine, phosphonite, phosphite, hydrazide, thiol, tetrazine, alkene, cyclooctyne, electron-withdrawing substituents such as halogens, e.g. F, Br, Cl, I, phenol-derivatives (e.g. OTs, ONs, OTf), nitriles (CN), carbonyls (CO), or nitro groups (NO2). The tyrosine derivative may be substituted with the above mentioned functional groups at positions 2, 3 and 4 as well as at the benzylic position. The functional groups may be connected directly at the above mentioned positions or via a spacer, such as an alkyl spacer in between. By way of example, the tyrosine derivative may be a 3-substituted or 4-substituted tyrosine, such as 3- or 4-substituted tyrosine derivative is 3-nitrotyrosine, 3-aminotyrosine, 3-azidotyrosine, 3-formyltyrosine, 3-acetyltyrosine, or 4-aminophenylalanine.

Further, a moiety can be conjugated to said tyrosine derivative. Said moiety can be a carrier, a polypeptide, a detectable label, a chemical compound, a nucleic acid, a carbohydrate, or a lipid. The polypeptide can be, in particular, an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. The detectable label may comprise a fluorophore, an enzyme (peroxidase, luciferase), a radioisotope, a fluorescent protein, or a fluorescent dye. The chemical compound can be a small molecule, a polymer, such as a synthetic polymer (PEG) or a therapeutic agent. The nucleic acid can be DNA, RNA, or an aptamer.

Also provided by the present invention is a diagnostic composition comprising a polypeptide that is, for example, obtainable by the methods of the present invention.

Furthermore, also provided is a pharmaceutical composition a polypeptide that is, for example, obtainable by the methods of the present invention.

The present invention moreover provides a kit comprising means for performing the method of the present invention. The kit may comprise an expression vector which allows expression of a protein of interest fused at its C-Terminus to a recognition sequence for tubulin tyrosine ligase, tubulin tyrosine ligase and a tyrosine derivative.

Also provided by the present invention is the use of tubulin tyrosine ligase for tyrosinating a polypeptide other than tubulin having at its C-terminus a recognition sequence for tubulin tyrosine ligase.

A method for installing a chemistry handle to the C-terminus of a polypeptide other than tubulin is also provided herein, said method comprising:
(a) providing a polypeptide having at its C-terminus a tubulin tyrosine ligase recognition sequence; and
(b) contacting the polypeptide of step (a) in the presence of tubulin tyrosine ligase and a tyrosine derivative containing a chemistry handle under conditions suitable for the tubulin tyrosine ligase to tyrosinate said polypeptide with said tyrosine derivative.

Said method may optionally further comprise the step of conjugating a moiety as described herein to said tyrosinated polypeptide obtained in step (b).

The present invention also provides the use of tubulin tyrosine ligase for installing a chemistry handle to the C-terminus of a polypeptide other than tubulin, said polypeptide having at its C-terminus a tubulin tyrosine ligase recognition sequence.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

a) Schematic outline of Tub-tag labeling of GFP in complex protein mixtures (*E. coli* lysate). b) Coomassie staining and western blot analysis showing the high selectivity of the tyrosine ligation and subsequent biotinylation. (+: lysate treated with TTL, 3-$N_3$-L-tyrosine (1) and DBCO-biotin; C1: no 3-$N_3$-L-tyrosine (1) added; C2: lysate treated with DBCO-biotin; C3: lysate; C4: purified GFP).

c) Outline of the site-specific biotinylation of the GFP-binding nanobody GBP1 and subsequent immunoprecipitation of GFP.

d) Coomassie staining and western blot analysis showing efficient and specific GFP pulldown (Mock GBP1-biotin: lysate lacking overexpressed GFP; GFP GBP1-biotin: beads loaded with GBP1 and lysate containing GFP; GFP control beads: beads without immobilized GBP1, I: input to streptavidin beads; FT: flow-through; B: beads).

e) Outline of the site-specific labeling of GBP1 with Alexa594 f) Immunofluorescence with GBP1-Alexa594. Shown is a fixed HeLa cell nucleus with the lamina co-labeled with LaminB1-GFP and GBP1-Alexa594. Scale bar: 10 mm.

g) expansion of the region highlighted in (d).

h) Fluorescence intensity profile along the dotted line shown in (g) demonstrates high colocalization accuracy at sub-diffraction resolution.

Figure 24:
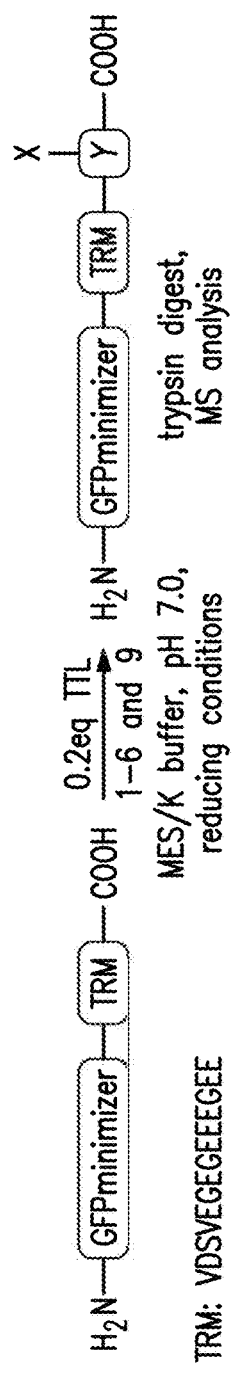

FIG. 24 is a representation of the C-terminal incorporation of tyrosine derivatives to nanobodies.

Figure 25:
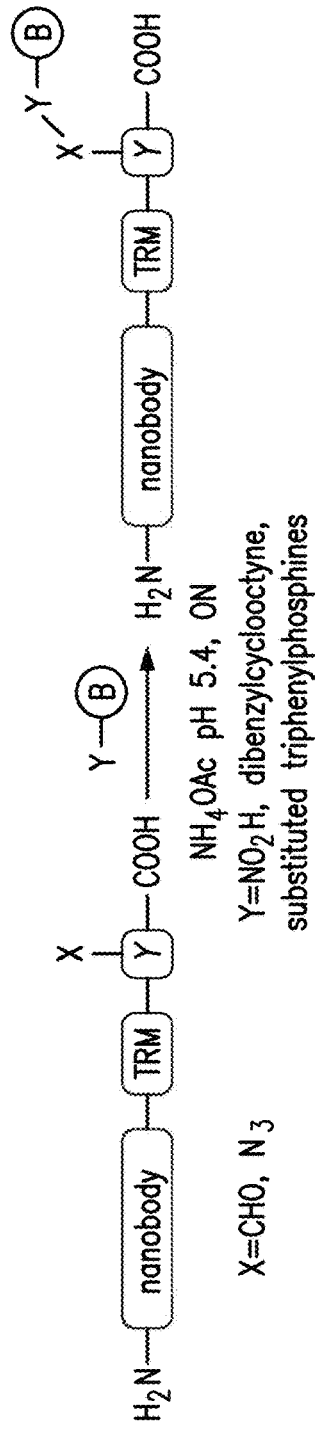

FIG. 25 is a representation of the labelling of tyrosinated nanobodies with biotin.

Figure 26:
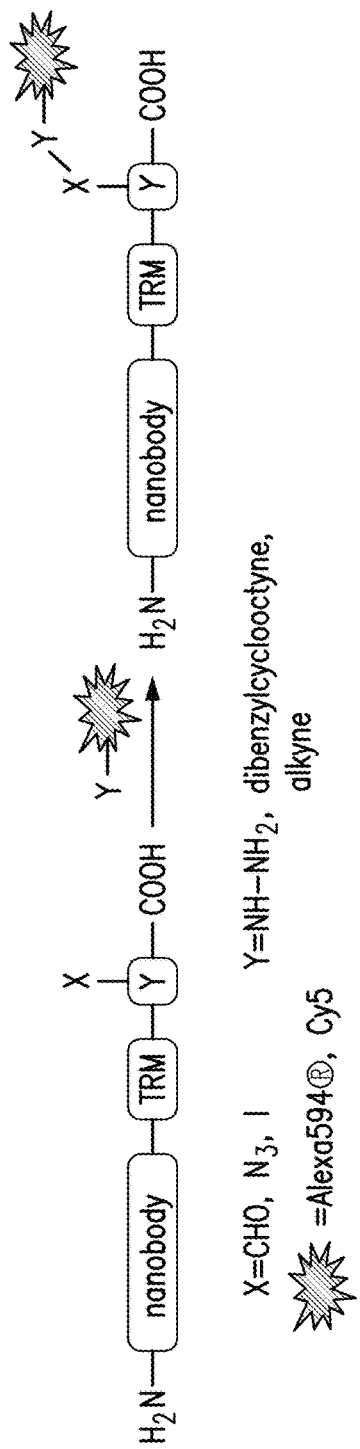

FIG. 26 is a representation of the labelling of a tyrosinated nanobody with Alexa594®.

Figure 27:
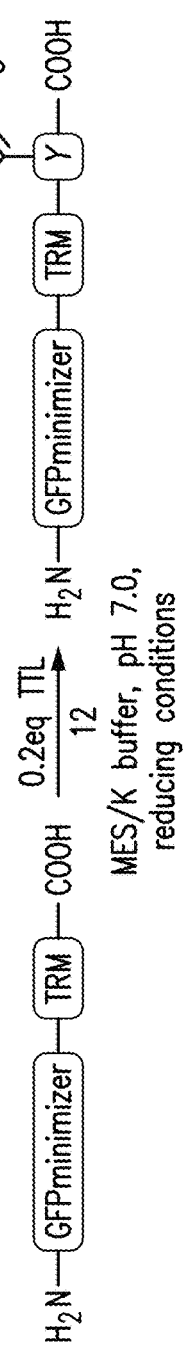

FIG. 27 is a representation of the one-step labeling of nanobody with biotin 12.

Figure 28:
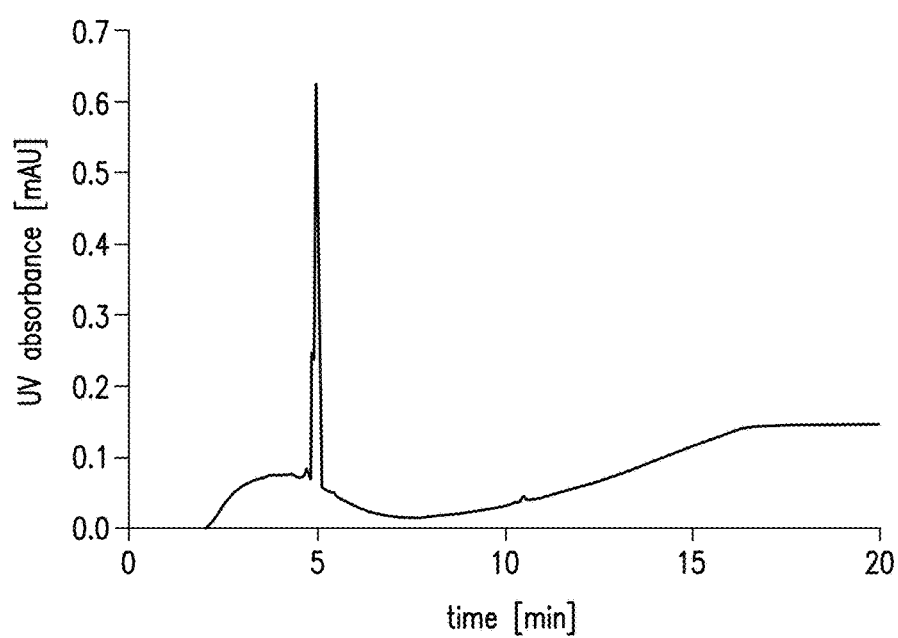

FIG. 28 shows a plot, UV absorbance [mAU] on the y-axis versus time [min] on the x-axis for a LC-UV at 220 nm, 10 to 100% of acetonitrile in water containing 0.1% TFA on a RP-C18 column.

DETAILED DESCRIPTION

The present inventors have, for the first time, acknowledged that TTL activity is not limited to tubulin, but that TTL is capable of tyrosinating virtually any polypeptide having a C-terminal TTL recognition motif in its amino acid sequence. This insight was by far not self-evident—in the past, several studies investigated the principles of TTL-tubulin interaction, and came to the conclusion that the unique interaction of TTL and its substrate tubulin was essential for effective tyrosination. The insight that TTL could tyrosinate any functional polypeptide carrying the specific recognition motif therefore came as a surprise. It also came as a surprise that TTL can incorporate tyrosine derivatives at the C-terminus of a non-tubulin polypeptide. These two surprising findings open up new avenues for post-translational modifications of polypeptides, since the tyrosine derivative may comprise a functional entity that allows its conjugation to whatever moiety that can confer functionality to a polypeptide of interest that is tyrosinated. The present invention therefore provides novel polypeptides carrying a C-terminal TTL recognition sequence; which can, inter alia, act as TTL substrates to become tyrosinated and, advantageously further functionalized, since—as explained—the C-terminal tyrosine can beneficially be used as an "adapter" for attaching further moieties, e.g. fluorescent labels or therapeutic agents. Therefore, the present invention provides means and methods that hold considerable potential for therapy, diagnosis and research.

Thus, the present invention provides a preferably recombinant or synthetic polypeptide having at its C-terminus a recognition sequence for tubulin tyrosine ligase (TTL). Said recognition sequence has preferably at least the amino acid sequence $X_4X_3X_2X_1$, wherein $X_2$ is E, D or C and $X_1$ is E. Said polypeptide is, as described herein, modified to introduce or add said recognition sequence. Said polypeptide has advantageously biological activity. Said polypeptide has preferably a length of more than 19 amino acids, such as 20, 30, 40, 50, 60, 70, 80, 90, 100, 150, 200, 250, or more amino acids in length.

The present invention also provides a method for the production of a polypeptide comprising
(a) introducing or adding at the C-terminus of a polypeptide a recognition sequence for tubulin tyrosine ligase;
(b) optionally contacting the polypeptide obtained in step (a) in the presence of tubulin tyrosine ligase and a tyrosine derivative under conditions suitable for the tubulin tyrosine ligase to tyrosinate said polypeptide with said tyrosine derivative; and
(c) optionally conjugating a moiety to said tyrosinated polypeptide obtained in step (b).

Step (c) is also envisaged to be a preferred step of the above method. Hence, in a preferred embodiment, said above method of the present invention further comprises step (c) conjugating a moiety to said tyrosinated polypeptide obtained in step (b).

As an alternative, the present in invention also provides a method for the production of a polypeptide comprising
(a') introducing or adding at the C-terminus of a polypeptide a recognition sequence for tubulin tyrosine ligase; and
(b') contacting the polypeptide obtained in step (a') in the presence of tubulin tyrosine ligase and a tyrosine derivative (already) conjugated to a moiety under conditions suitable for the tubulin tyrosine ligase to tyrosinate said polypeptide with said tyrosine derivative conjugated to said moiety.

Said alternative method allows, so to say, a one-step functionalization of a polypeptide in that tubulin tyrosine ligase tyrosinates a polypeptide into which a recognition sequence for tubulin tyrosine ligase is introduced or added at its C-terminus with a tyrosine derivative conjugated to a moiety. Thus, said method, so to say, simplifies the functionalization in that no extra tyrosination step is required, where tubulin tyrosine ligase first adds a tyrosine derivative to the C-terminus of a polypeptide into which a recognition sequence for tubulin tyrosine ligase is introduced or added in order to then conjugate a moiety to said tyrosinated polypeptide. Rather, tubulin tyrosine ligase was found by the present inventors to tyrosinate a polypeptide into which a recognition sequence for tubulin tyrosine ligase is introduced or added at its C-terminus with a tyrosine derivative already conjugated to a moiety.

The terms "protein," "peptide" and "polypeptide" are used interchangeably herein, and refer to a polymer of amino acid residues linked together by peptide (amide) bonds. Said term also encompasses fragments of polypeptides. Said fragments may have preferably biological activity. Said fragments may have a length of 10, 20, 30, 40, 50, 60, 70, 80, 90, 100, 150, 200, 250, 300, 350, 400, 450 or more amino acids. The terms refer to a protein, peptide, or polypeptide of any size, structure, or function, with the exception of tubulin. The term "tubulin" as used herein comprises any isoform (i.e., α-, β-, γ-, δ-, ε-, ζ-tubulin), mutant, variant or derivative of tubulin. As explained herein, the finding of the present invention is, inter alia, that polypeptides other than tubulin, i.e. non-tubulin polypeptides are tyrosinated by TTL, provided they have a TTL recognition sequence. In other words, the present inventors found that TTL is active on heterologous substrates, such as peptides or polypeptides that merely contain a TTL recognition sequence at their C-terminus, but are otherwise not structurally related to a tubulin. "Heterologous substrate" means a peptide or polypeptide on which TTL is active by way of tyrosination, but which is not a tubulin.

"A polypeptide or peptide other than tubulin" or "a non-tubulin peptide or polypeptide" encompasses a polypeptide which is not structurally related to a tubulin polypeptide. Such a tubulin polypeptide has preferably an amino acid sequence having a sequence identity of 60% or more, such as 70%, 80%, 90% or 100%, to SEQ ID No. 1.

Thus, such tubulin polypeptides are preferably excluded from a polypeptide of the present invention that is tyrosinated and further modified by conjugation of a moiety to the tyrosine of the tyrosinated polypeptide or that is tyrosinated with a tyrosine derivative (already) conjugated to a moiety.

A variety of sequence based alignment methodologies, which are well known to those skilled in the art, can be used to determine identity among sequences. These include, but not limited to, the local identity/homology algorithm of Smith, F. and Waterman, M. S. (1981) Adv. Appl. Math. 2: 482-89, homology alignment algorithm of Peason, W. R. and Lipman, D. J. (1988) Proc. Natl. Acad. Sci. USA 85: 2444-48, Basic Local Alignment Search Tool (BLAST) described by Altschul, S. F. et al. (1990) J. Mol. Biol. 215: 403-10, or the Best Fit program described by Devereau, J. et al. (1984) Nucleic Acids. Res. 12: 387-95, and the FastA and TFASTA alignment programs, preferably using default settings or by inspection. Alternatively, an alignment may be done manually/visually as follows: the percent identity between an amino acid sequence in question and the amino acid sequence shown in SEQ ID No. 1 (reference sequence) is determined by pairwise alignment in such a way that the maximum identity is obtained between both amino acid sequences. The identical amino acid residues between both amino acid sequences are counted and divided by the total number of residues of the amino acid sequence shown in SEQ ID No. 1 (including positions that do not contain amino acid residues, e.g. one or more gaps) yielding the percentage of identity.

A protein, peptide, or polypeptide may refer to an individual protein or a collection of proteins. One or more of the amino acids in the polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, a fusion partner for half-life extension, an affinity tags, such as a histidine tag, Flag-tag, streptavidin tag, strep II tag, an intein, a maltose-binding protein, an IgA or IgG Fc portion, protein A or protein G, and other modifications. Other possible chemical modifications of the polypeptide include acylation or acetylation of the amino-terminal end or amidation or esterification of the carboxy-terminal end or, alternatively, on both. The modifications may also affect the amino group in the side chain of lysine or the hydroxyl group of threonine. Other possible modifications include, e.g., extension of an amino group with polypeptide chains of varying length (e.g., XTEN technology or PASylation®), N-glycosylation, O-glycosylation, and chemical conjugation of carbohy-

```
                                                       (SEQ ID NO. 1)
MRECISIHVG QAGVQIGNAC WELYCLEHGI QPDGQMPSDK TIGGGDDSFN        50

TFFSETGAGK HVPRAVFVDL EPTVIDEVRT GTYRQLFHPE QLITGKEDAA       100

NNYARGHYTI GKEIIDLVLD RIRKLADQCT GLQGFLVFHS FGGGTGSGFT       150

SLLMERLSVD YGKKSKLEFS IYPAPQVSTA VVEPYNSILT THTTLEHSDC       200

AFMVDNEAIY DICRRNLDIE RPTYTNLNRL IGQIVSSITA SLRFDGALNV       250

DLTEFQTNLV PYPRIHFPLA TYAPVISAEK AYHEQLSVAE ITNACFEPAN       300

QMVKCDPRHG KYMACCLLYR GDVVPKDVNA AIATIKTKRT IQFVDWCPTG       350

FKVGINYQPP TVVPGGDLAK VQRAVCMLSN TTAIAEAWAR LDHKFDLMYA       400

KRAFVHWYVG EGMEEGEFSE AREDMAALEK DYEEVGVDSV EGEGEEEGEE
``` drates, such as hydroxyethyl starch (e.g., HESylation®) or polysialic acid (e.g., PolyXen® technology). Chemical modifications such as alkylation (e. g., methylation, propylation, butylation), arylation, and etherification may be possible and are also envisaged. It is however preferred that the modification does not abolish the capability of TTL to recognize the TTL recognition sequence and/or to tyrosinate the polypeptide of the invention. A protein, peptide, or polypeptide may also be a single molecule or may be a multi-molecular complex. A protein, peptide, or polypeptide may be just a fragment of a naturally occurring protein or peptide, as long as it exhibits biological activity as defined herein.

The term "Tubulin tyrosine ligase", abbreviated sometimes herein as TTL, encompasses polypeptides that are capable of tyrosinating polypeptides, i.e. covalently attaching a tyrosine or tyrosine derivative to a polypeptide. Preferably a TTL is capable of tyrosinating a polypeptide at the C-terminus of said polypeptide. For that action it is preferred that said polypeptide comprises a recognition sequence for TTL. Said term encompasses TTLs from eukaryotes, preferably mammals, more preferably from humans. A preferred TTL is shown in SEQ ID No: 12. Also encompassed by said term is a TTL that has 70%, 80%, 90% or 95% or more identity over its entire amino acid sequence with the amino acid sequence of the TTL shown in SEQ ID No: 12. Preferably, such polypeptides having an amino acid sequence which shares an identity as described before have TTL activity. TTL activity can be tested as is known in the art or described herein. The percentage of sequence identity can, for example, be determined herein as described above. Preferably the amino acid sequence shown in SEQ ID No: 12 is used as reference in a pairwise comparison. It is calculated as the percentage of numbers of "positives" (homologous amino acids) indicated as result in the BLASTP program output divided by the total number of amino acids selected by the program for the alignment.

Figure 22:
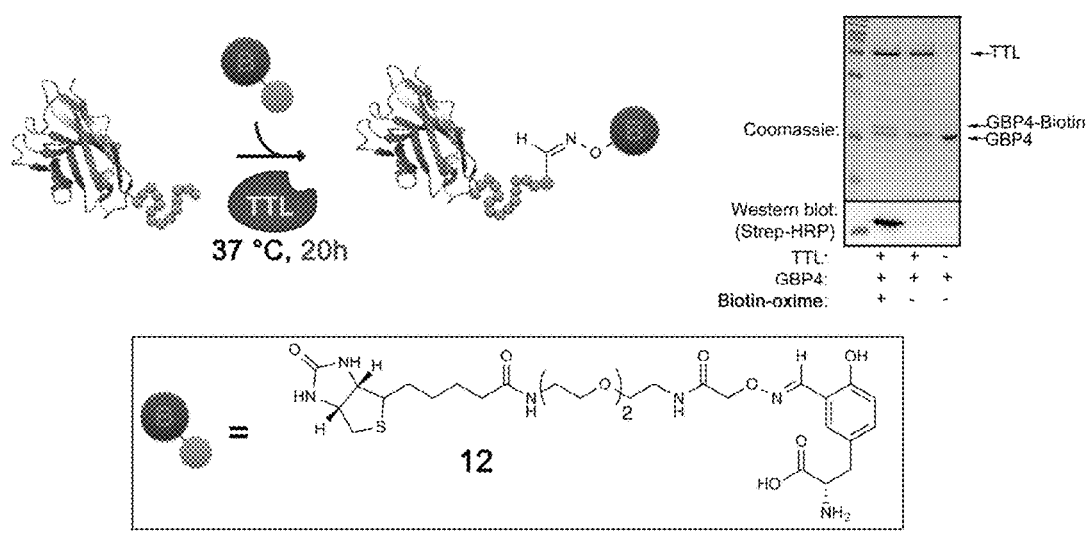
FIG. 22: One-Step Functionalization: TTL is able to add a tyrosine derivative, which is already coupled to a moiety, to a polypeptide.
Figure 23:
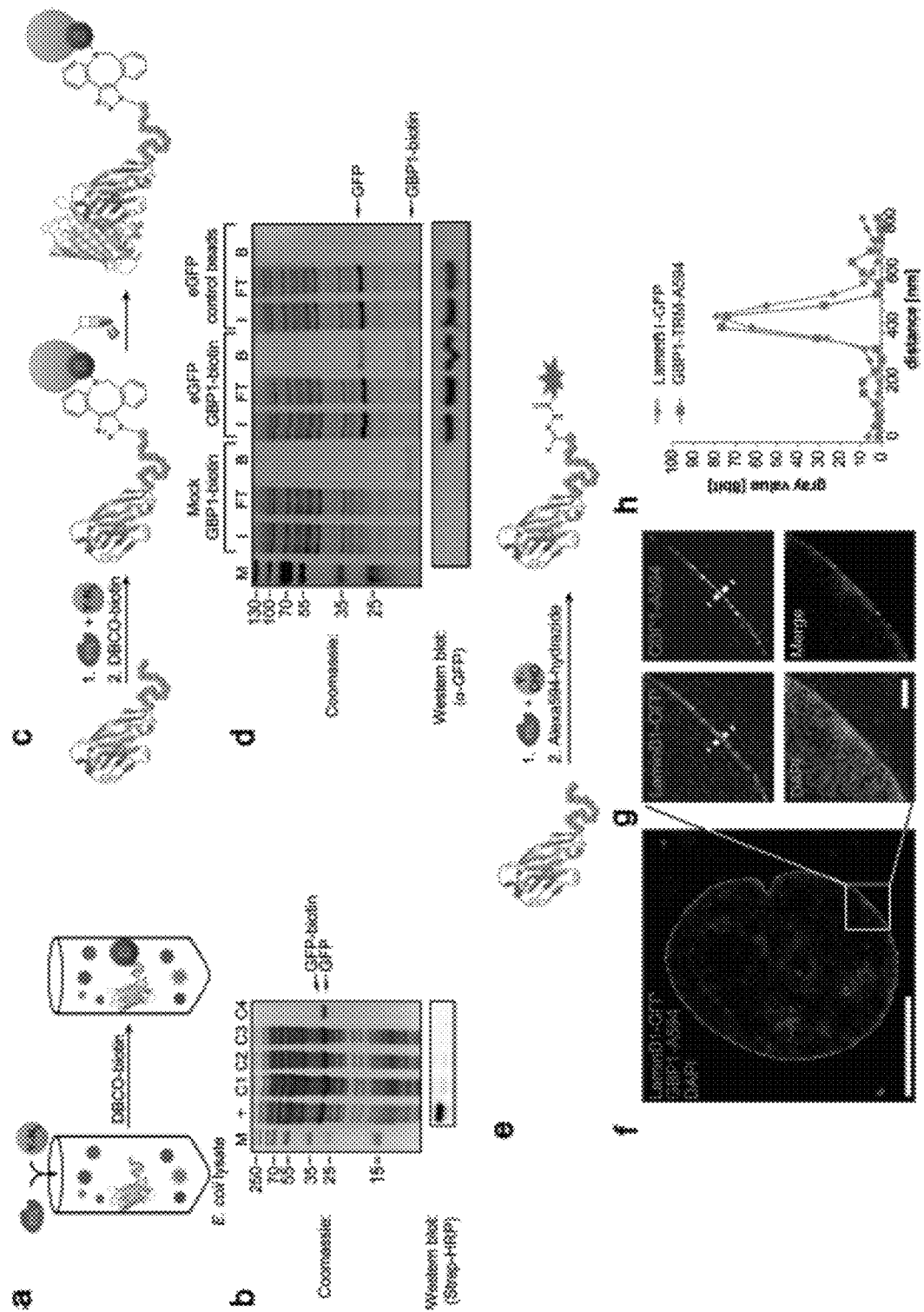
FIG. 23. Lysate labeling and the application of chemoenzymatically functionalized nanobodies to protein enrichment and super resolution microscopy.

The term "tyrosinating" in all its grammatical forms as used herein means "covalently attaching a tyrosine or tyrosine derivative" to a polypeptide. Without wishing to be bound by a specific theory, it is envisaged that the TTL adds a tyrosine or tyrosine derivative to the ultimate C-terminal amino acid of the TTL recognition motif. Said tyrosine or tyrosine derivative may already be conjugated to a moiety as described herein. Conjugation of a moiety to a tyrosine or tyrosine derivative may be done as is known in the art or preferably be done as described herein. Accordingly, it is thus also envisaged that the term "tyrosinating" encompassed that tubulin tyrosine ligase tyrosinates a polypeptide having a recognition sequences for TTL as described herein with a tyrosine or tyrosine derivative that is (already) conjugated with a moiety as described herein. This finding of the present inventors was again surprising in that TTL is able to use even tyrosine derivatives conjugated to large or bulky moieties (see FIG. 22).

The present invention preferably pertains to a "recombinant" or "synthetic" polypeptide. A "synthetic" polypeptide in the context of the present invention refers to a polypeptide that has been obtained by methods of synthetic biology, including solid phase peptide synthesis (SPPS), prior thiol capture strategy, native chemical ligation (NCL), expressed protein ligation (EPL) and Staudinger ligation, and the O-acyl isopeptide method. Such a synthetic polypeptide contains a TTL recognition sequence that is introduced either by addition or modification of the amino acid sequence of the synthetic polypeptide. The term "synthetic" polypeptide as used herein also includes polypeptides which have been treated to alter their natural amino acid sequence, e.g., by deamidation.

The term "recombinant" in the context of the present invention refers to a polypeptide that is genetically engineering, i.e., modified to introduce or add a recognition sequence for TTL at the C-terminus of a polypeptide. It thus excludes such tubulins which naturally contain a TTL recognition sequence.

"Modified to introduce a recognition sequence" means that the amino acid sequence of a polypeptide is modified to introduce a TTL recognition sequence, such as replacing or deleting, but not adding or inserting, one or more amino acids in order to build a TTL recognition sequence at the C-terminus of a polypeptide.

"Modified to add a recognition sequence" means that the amino acid sequence of a polypeptide is modified to add a TTL recognition sequence, i.e., adding or inserting one or more amino acids in order to equip a polypeptide with a TTL recognition sequence at its C-Terminus.

Examples of polypeptides or proteins include recombinant or synthetic hormones, cytokines and lymphokines, antibodies, receptors, adhesion molecules, and enzymes as well as fragments thereof. A non-exhaustive list of desired polypeptides include, e. g., recombinant or synthetic human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A- or B-chain; prorelaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), growth factors including vascular endothelial growth factor (VEGF), nerve growth factor such as NGF-; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-pl, TGF-p2, TGF-p3, TGF-p4, or TGF-p5; insulin-like growth factor-I and -II (IGF-I and IGF-11); des (1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; erythropoietin; T-cell receptors; surface membrane proteins e.g., HER2; decoy accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

The polypeptide of the invention is modified to comprise a recognition sequence for tubulin-tyrosine ligase (TTL) at its C-terminus, comprising at least the amino acid sequence $X_4X_3X_2X_1$. The term "recognition sequence" or "recognition motif" are used interchangeably herein and refer to a stretch of amino acids that is recognized by the TTL. Such recognition sequences are known in the art; see, e.g., Ruediger et al. (1994), Eur. J. Biochem. 220, 309-320 or Prota e al. (2013), J. Cell. Biol. 200, No. 3, 259-270. Moreover, the skilled person can easily test whether or not an amino acid sequence of interest is a TTL recognition sequence by applying, e.g., the assay "Tyrosination of peptides by TTL" described in Ruediger et al., "Recognized" by the TTL includes binding of the TTL to the recognition motif. The recognition motif advantageously comprises at least 4 amino acids which are designated $X_4$, $X_3$, $X_2$ and $X_1$ herein. In general, "X" can denote any amino acid unless indicated otherwise herein. Amino acids include includes but is not limited to the twenty "standard" amino acids: isoleucine (Ile, I), leucine (Leu, L), lysine (Lys, K), methionine (Met, M), phenylalanine (Phe, F), threonine (Thr, T), tryptophan (Trp, W), valine (Val, V), alanine (Ala, A), asparagine (Asn, N), aspartate (Asp, D), cysteine (Cys, C), glutamate (Glu, E), glutamine (Gln, Q), glycine (Gly, G), proline (Prol, P), serine (Ser, S), tyrosine (Tyr, Y), arginine (Arg, R) and histidine (His, H). The present invention also includes, without limitation, D-configuration amino acids, β-amino acids, amino acids having side chains as well as all non-natural amino acids known to one skilled in the art. $X_1$ refers to the ultimate C-terminal amino acid in the polypeptide, $X_2$ to the second to the last, and so on. $X_1$ is E, and $X_2$ is selected from E, D or C. $X_3$ is preferably G, S, A, V, or F, whereas $X_4$ is preferably selected from E, D, A, K or P. In some embodiments, $X_5$ (i.e. the next amino acid towards the N-terminus of $X_4$) is selected from E, A and V. In some embodiments, $X_6$ (i.e. the amino acid following $X_5$) can be selected from E, A, K and G. In general, any combination of $X_1$ and $X_2$ is conceivable which does not abolish the ability of the TTL to recognize the respective recognition motif. The TTL recognition sequence introduced in or added to the polypeptide of the invention can for example be EGEE (SEQ ID No. 2). In one particular embodiment, the TTL recognition sequence is VDSVEGEGEEEGEE (SEQ ID No. 3, sometimes also referred to herein as TTL reactive motif), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8). In general, any recognition sequence is envisaged wherein $X_1$ is E and $X_2$ is E, D or C, which is recognized by the TTL.

The term "having biological activity" as used herein means that a polypeptide has a specific functionality. For example, if the polypeptide of the invention is a modified antibody, "having biological activity" can mean, e.g., having antigen-binding activity. If the polypeptide of the invention is a modified enzyme, "having biological activity" can mean, e.g., having enzymatic activity.

The polypeptide can comprise a linker sequence preceding the recognition sequence of tubulin tyrosine ligase. A "linker sequence" (also referred to as a "spacer sequence") is an amino acid sequence that is introduced between the polypeptide of the invention and the TTL recognition sequence, so as to connect the polypeptide and the TTL recognition sequence. A linker sequence can for example be required in order to allow accurate folding of the polypeptide of the invention, and/or to ensure flexibility and accessibility of the TTL recognition sequence. There are a great variety of possible linker sequences and it is within the knowledge of the person skilled in the art to choose a suitable linker sequence based on, e.g., the size, sequence and physical properties (such as hydrophobicity) of the polypeptide of the invention. Linker sequences can be composed of flexible residues like glycine and serine. It may be preferred that the linker sequence does not adopt a secondary structure (such as a α-helical structure or a β-sheet) in order to ensure maximal flexibility of the attached TTL recognition motif.

In the polypeptide of the invention, a tyrosine derivative can be covalently bonded to said recognition sequence. The tyrosine derivative may be substituted with the above mentioned functional groups at positions 2, 3 and 4 as well as at the benzylic position. The functional groups may be connected directly at the above mentioned positions or via a spacer, such as an alkyl spacer in between. By way of example, the tyrosine derivative may be a 3-substituted or 4-substituted tyrosine, such as 3- or 4-substituted tyrosine derivative is 3-nitrotyrosine, 3-aminotyrosine, 3-azidotyrosine, 3-formyltyrosine, 3-acetyltyrosine, 3-iodotyrosine or 4-aminophenylalanine. Also encompassed by the term "tyrosine derivative" is phenylalanine or any other substrate that is attached by tubulin tyrosine ligase to the C-terminus of a polypeptide which preferably comprises a recognition sequence for TTL. Advantageously said other substrate resembles tyrosine or y tyrosine derivative as described herein. Preferably said other substrate contains an unnatural functional group for chemoselective or bioorthogonal modifications.

The term "covalently bonded" is used herein interchangeably with the terms "covalently attached to" and "covalently joined" and refers to a type of chemical bond involving the sharing of two electron pairs between atoms. Without wishing to be bound by a specific theory, it is envisaged that the tyrosine derivative is covalently attached to the TTL recognition sequence by the action of the TTL, so that the tyrosine derivative is attached to the ultimate C-terminal amino acid of the recognition sequence, which is designated $X_1$ herein. The same applies for the attachment of tyrosine, mutatis mutandis. The resulting C-terminal amino acid sequence will then be $X_4X_3X_2X_1X_0$, wherein $X_0$ refers to a tyrosine or a tyrosine derivative.

The tyrosine derivative may further contain an unnatural (non-natural) functional group, which is preferably used for chemoselective or bioorthogonal modifications. The term "click chemistry" refers to a chemical philosophy introduced by Kolb, Finn and Sharpless in 2001 and encompasses a group of powerful linking reactions that are able to generate covalent bonds quickly and reliably by joining small units comprising reactive groups together. Click chemistry reactions are typically modular, wide in scope, give high chemical yields, generate inoffensive byproducts, are stereospecific, exhibit a large thermodynamic driving force >84 kJ/mol to favor a reaction with a single reaction product, and/or can be carried using readily available starting materials and reagents out under simple, physiological reaction conditions. In addition, click chemistry reactions preferably use no toxic solvents or use a solvent that is benign or easily removed (preferably water), and/or provides simple product isolation by non-chromatographic methods (crystallisation or distillation). A distinct exothermic reaction makes a reactant "spring loaded".

Click chemistry reactions comprise, e.g., cycloaddition reactions, especially from the 1,3-dipolar family, hetero-Diels-Alder reactions; nucleophilic ring-opening reactions, e.g. of strained heterocyclic electrophiles, such as epoxides, aziridines, cyclic sulfates, cyclic sulfamidates, aziridinium ions and episulfonium ions; carbonyl chemistry of the non-aldol type (e.g. the formation of oxime ethers, hydrazones and aromatic heterocycles); and addition to carbon-carbon multiple bonds; e.g. oxidation reactions, such as epoxidation dihydroxylation, aziridination, and nitrosyl and sulfenyl halide additions but also certain Michael addition reactions. General principles of click chemistry reactions have been described by Kolb, Finn and Sharpless (2001). It is within the knowledge of the person skilled in the art to select a click chemistry reaction that is suitable for attaching a desired moiety to the tyrosine derivative covalently bonded to the polypeptide of the invention.

The term "click chemistry handle," as used herein, refers to a reactant, or a reactive group, that can partake in a click chemistry reaction. Such a reactant or reactive group is preferably an unnatural (non-natural) functional group for a chemoselective or bioorthogonal modification; however, it may alternatively be a natural functional group for a chemoselective or bioorthogonal modification. For example, a strained alkyne, e.g., a cyclooctyne, is a click chemistry handle, since it can partake in a strain-promoted cycloaddition, e.g. strain-promoted azide-alkyne cycloaddition (SPARC). In general, click chemistry reactions require at least two molecules comprising click chemistry handles that can react with each other. Such click chemistry handle pairs that are reactive with each other are sometimes referred to herein as "partner click chemistry handles". For example, an azide is a partner click chemistry handle to a cyclooctyne or any other alkyne. In the context of the present invention, the click chemistry handle can preferably be selected from the group consisting of terminal alkyne, azide, strained alkyne, diene, dienophile, alkoxyamine, carbonyl, phosphine, hydrazide, thiol, tetrazine, alkene, and cyclooctyne. Other suitable click chemistry handles are readily accessible to the person skilled in the art.

In the context of conjugation via click chemistry, the conjugation is via a covalent bond formed by the reaction of the click chemistry handles. In certain embodiments, the association is covalent, and the entities are said to be "conjugated" to one another. In some embodiments, a protein is post-translationally conjugated to another molecule, for example, a second protein, by forming a covalent bond between the protein and the other molecule after the protein has been translated, and, in some embodiments, after the protein has been isolated. In some embodiments, the post-translational conjugation of the protein and the second molecule, for example, the second protein, is effected via installing a click chemistry handle on the protein, and a second click chemistry handle, which can react to the first click chemistry handle, on the second molecule, and carrying out a click chemistry reaction in which the click chemistry handles react and form a covalent bond between the protein and the second molecule, thus generating a chimeric protein. In some embodiments, two proteins are conjugated at their respective C-termini, generating a C—C conjugated chimeric protein. In some embodiments, two proteins are conjugated at their respective N-termini, generating an N—N conjugated chimeric protein.

The term "alkene" refers to a hydrocarbon having at least one carbon-carbon double bond.

The term "alkyne" refers to a hydrocarbon having at least one carbon-carbon triple bond. As used herein, the term "terminal alkyne" refers to an alkyne wherein at least one hydrogen atom is bonded to a triply bonded carbon atom. The term "strained alkyne" refers to As used herein the term "strained alkyne group" may comprise the ring that comprises a carbon to carbon triple bond and may also comprise substituent groups. Cyclooctyne is an exemplary strained alkyne that is envisaged for use in the present invention, e.g. Dibenzocyclooctyne (DBCO).

The term "azide" or "azido," as used herein, refers to a group of the formula (—$N_3$).

The term "diene" refers to a hydrocarbon that contains two carbon double bonds.

The term "dienophile" refers to a compound that reacts with a diene in a Diels-Alder reaction to give a cycloaddition product.

The term "alkoxyamine" refers to any alkoxy derivative of an amine.

The term "alkoxy" refers to an alkyl group bonded through an oxygen (—O—).

The term "amine" refers to a derivative of ammonia, wherein one or more hydrogen atoms have been replaced by a substituent such as an alkyl or aryl group.

The terms "alk" or "alkyl" refer to straight or branched chain hydrocarbon groups having 1 to 12 carbon atoms, preferably 1 to 8 carbon atoms.

The term "carbonyl" refers to a group comprising a carbon atom double-bonded to an oxygen atom. Examples include ketones, aldehydes or carboxylic acids or protected forms thereof.

The term "phosphine" refers to the compound with the chemical formula $PZ^1Z^2Z^3$, where each of $Z^1$, $Z^3$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof. The term "phosphonite" $P(OZ^1)(OZ^2)Z^3$, where each of $Z^1$, $Z^3$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof. The term "phosphite" $P(OZ^1)(OZ^2)(OZ^3)$, where each of $Z^1$, $Z^3$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "hydrazide" refers to a compound having a nitrogen-nitrogen covalent bond with four substituents with at least one of them being an acyl group.

The term "thio" or "thiol," as used herein, refers to a group of the formula (—SR), wherein R is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. A "substituted thiol" refers to a group of the formula (—SR'), wherein R' can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$ alkyl). In another embodiment, the alkyl group employed contains 1-15 carbon atoms ($C_{1-15}$ alkyl). In another embodiment, the alkyl group employed contains 1-10 carbon atoms ($C_{1-20}$ alkyl). In another embodiment, the alkyl group employed contains 1-8 carbon atoms ($C_{1-8}$ alkyl). In another embodiment, the alkyl group employed contains 1-6 carbon atoms ($C_{1-6}$ alkyl). In another embodiment, the alkyl group employed contains 1-5 carbon atoms ($C_{1-5}$-alkyl). In another embodiment, the alkyl group employed contains 1-4 carbon atoms ($C_{1-4}$ alkyl). In another embodiment, the alkyl group employed contains 1-3 carbon atoms ($C_{1-3}$ alkyl). In another embodiment, the alkyl group employed contains 1-2 carbon atoms ($C_{1-2}$ alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety.

The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$ alkenyl). In some embodiments, the alkenyl group employed in the invention contains 2-15 carbon atoms ($C_{2-15}$ alkenyl). In another embodiment, the alkenyl group employed contains 2-10 carbon atoms ($C_{2-10}$ alkenyl). In still other embodiments, the alkenyl group contains 2-8 carbon atoms ($C_{2-8}$ alkenyl). In yet other embodiments, the alkenyl group contains 2-6 carbons ($C_{2-6}$ alkenyl). In yet other embodiments, the alkenyl group contains 2-5 carbons ($C_{2-5}$ alkenyl). In yet other embodiments, the alkenyl group contains 2-4 carbons ($C_{2-4}$ alkenyl). In yet other embodiments, the alkenyl group contains 2-3 carbons ($C_{2-3}$ alkenyl). In yet other embodiments, the alkenyl group contains 2 carbons ($C_2$ alkenyl). Alkenyl groups include, for example, ethenyl, propenyl, butenyl, and the like, which may bear one or more substituents. Alkenyl group substituents include, but are not limited to, any of the substituents described herein, that result in the formation of a stable moiety.

The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$ alkynyl). In some embodiments, the alkynyl group employed in the invention contains 2-15 carbon atoms ($C_{215}$ alkynyl). In another embodiment, the alkynyl group employed contains 2-10 carbon atoms ($C_{2-10}$ alkynyl). In still other embodiments, the alkynyl group contains 2-8 carbon atoms ($C_{2-8}$ alkynyl). In still other embodiments, the alkynyl group contains 2-6 carbon atoms ($C_{2-6}$ alkynyl). In still other embodiments, the alkynyl group contains 2-5 carbon atoms ($C_{2-5}$ alkynyl). In still other embodiments, the alkynyl group contains 2-4 carbon atoms ($C_{2-4}$ alkynyl). In still other embodiments, the alkynyl group contains 2-3 carbon atoms ($C_{2-3}$ alkynyl). In still other embodiments, the alkynyl group contains 2 carbon atoms ($C_2$ alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety.

The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms ($C_{3-10}$ carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl,"

"heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$ heteroaliphatic). In certain embodiments, the heteroaliphatic group contains 1-10 carbon atoms and 1-4 heteroatoms ($C_{1-10}$ heteroaliphatic). In certain embodiments, the heteroaliphatic group contains 1-6 carbon atoms and 1-3 heteroatoms ($C_{1-6}$ heteroaliphatic). In certain embodiments, the heteroaliphatic group contains 1-5 carbon atoms and 1-3 heteroatoms ($C_{1-5}$ heteroaliphatic). In certain embodiments, the heteroaliphatic group contains 1-4 carbon atoms and 1-2 heteroatoms ($C_{1-4}$ heteroaliphatic). In certain embodiments, the heteroaliphatic group contains 1-3 carbon atoms and 1 heteroatom ($C_{1-3}$ heteroaliphatic). In certain embodiments, the heteroaliphatic group contains 1-2 carbon atoms and 1 heteroatom ($C_{1-2}$ heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted.

Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms (02-6 heteroalkenyl). In certain embodiments, the heteroalkenyl group contains 2-5 carbon atoms and 1-3 heteroatoms (C2-5 heteroalkenyl). In certain embodiments, the heteroalkenyl group contains 2-4 carbon atoms and 1-2 heteroatoms (C2-4 heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl).

In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C4-C20 aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety.

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula $-C(=O)R^A$, $-C(=O)OR^A$, $-C(=O)-O-C(=O)R^A$, $-C(=O)SR^A$, $-C(=O)N(R^A)_2$, $-C(=S)R^A$, $-C(=S)N(R^A)_2$, and $-C(=S)S(R^A)$, $-C(=NR^A)R^A$, $-C(=NR^A)OR^A$, $-C(=NR^A)SR^A$, and $-C(=NR^A)N(R^A)_2$, wherein $R^A$ is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes ($-CHO$), carboxylic acids ($-CO_2H$), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: $-R^o-(C=X^1)-R^o-$, $-R^o-X^2(C=X^1)-R^o-$, or $-R^o-X^2(C=X^1)X^3-R^o-$, where $X^1$, $X^2$, $X^3$ is, independently, oxygen, sulfur, or $NR^r$, wherein $R^r$ is hydrogen or optionally substituted aliphatic, and $R^o$ is an optionally substituted alkylene, alkenylene, alkynylene, heteroalkylene, heteroalkenylene, or heteroalkynylene group, as defined herein. Exemplary acylene groups wherein $R^o$ is alkylene includes $-(CH_2)_T-O(C=O)-(CH_2)_T-$; $-(CH_2)_T-NR'(C=O)-(CH_2)_T-$; $-(CH_2)_T-O(C=NR')-(CH_2)_T-$; $-(CH_2)_T-NR'(C=NR')-(CH_2)_T-$; $-(CH_2)_T(C=O)-(CH_2)^{\hat{}}$; $_-(CH_2)^{\hat{}}(C=NR^R)-(CH_2)^{\hat{}}$; $-(CH_2)_T-S(C=S)-(CH_2)_T-$; $-(CH_2)_T NR'(C=S)-(CH_2)_T$; $-(CH_2)_T-S(C=NR')-(CH_2)_T$; $-(CH_2)_T-O(C=S)-(CH_2)_T$; $-(CH_2)_T-(C=S)-(CH_2)_T-$; or $-(CH_2)_T-S(C=O)-(CH_2)_T$, and the like, which may bear one or more substituents; and wherein each instance of T is, independently, an integer between 0 to 20. Acylene substituents include, but are not limited to, any of the substituents described herein, that result in the formation of a stable moiety.

It should be noted that the invention is not limited to the foregoing, exemplary click chemistry handles, and additional click chemistry handles, reactive click chemistry handle pairs, and reaction conditions for such click chemistry handle pairs will be apparent to those of skill in the art.

Other methods suitable for conjugating a moiety to the tyrosine derivative of the polypeptide of the invention comprise Staudinger reactions (e.g. Staudinger-ligation, Staudinger-Phosphite reaction), strain-promoted cycloadditions, tetrazine ligations, inverse-electron demand Diels-Alder reactions, thiazolidine-forming reactions of aldehydes or ketones with 1,2-aminothiols, oxazolidine-forming reactions of aldehydes or ketones with 1,2-aminoalcohols, acetal-forming reactions of aldehydes or ketones with 1,2-diols, metal-catalyzed, in particular Pd-, Cu, Ni and Fe-catalyzed cross couplings with tyrosine-derivatives substituted with electron-withdrawing groups.

It is envisaged that a moiety can be attached to the tyrosine derivative covalently bonded to the polypeptide of the invention, for example, by click chemistry or any other suitable method as described herein. A moiety may thus be conjugated to the tyrosine derivative of a tyrosinated polypeptide by a non-peptidic bond, however, in the alternative it may also be conjugated to the tyrosine derivative of a tyrosinated polypeptide by a peptidic-bond. Said moiety can be a carrier, a polypeptide, a detectable label, a chemical compound, a nucleic acid, a carbohydrate, or a lipid.

The term "carrier" when used herein refers to a moiety, such as, e.g., a molecule or polymer, which acts to improve delivery, effectiveness and/or stability of the polypeptide of the invention. For example, if the polypeptide of the invention is envisaged for treatment of a subject as described herein, the carrier may be a pharmaceutically acceptable carrier that can direct the polypeptide of the invention to a specific location, facilitate its transport, enhance its serum stability, bioavailability, and the like. Pharmaceutically acceptable carriers are described herein. A carrier may, however, also be a bead, such as a magnetic bead, or a solid surface. A solid surface may be selected from polystyrene, polypropylene, polyvinylchloride, polyacrylamide, celluloses, dextrans, synthetic polymers and co-polymers, latex, silica, agarose, metal, glass, or carbon.

Alternatively, the moiety that is conjugated to the tyrosine derivative attached to the polypeptide of the invention is a polypeptide (hereinafter referred to as "polypeptide moiety"). Any polypeptide is conceivable that can be attached to the tyrosine derivative covalently bonded to the polypeptide of the invention. The polypeptide moiety may require modification in order to be able to be attached.

In one particular embodiment, the polypeptide moiety is an antibody or fragment thereof. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses monoclonal antibodies, chimeric antibodies, humanized antibodies, human antibodies, scFv, DART, domain antibodies, nanobodies, adnectin, affibodies, anticalins, DARPins, aptamers or functional equivalents thereof of any one of the aforementioned antibody species as well as affinity binders.

A "detectable label" is a molecule or material that can produce a detectable (such as visually, electronically or otherwise) signal that indicates the presence and/or concentration of the label in a sample. Thereby, e.g., the presence, location and/or concentration of the polypeptide in a sample can be detected by detecting the signal produced by the detectable label. A detectable label can be detected directly or indirectly, It will be appreciated that the label may be attached to or incorporated into a molecule, for example, a protein, polypeptide, or other entity, at any position. It will be appreciated that, in certain embodiments, a label may react with a suitable substrate (e.g., a luciferin) to generate a detectable signal. In particular, the detectable label can be a fluorophore, an enzyme (peroxidase, luciferase), a radioisotope, a fluorescent protein, or a fluorescent dye. Other dectectable labels include chemiluminescent labels, electrochemiluminescent labels, bioluminescent labels, polymers, polymer particles, metal particles, haptens, and dyes.

A "fluorophore" (or fluorochrome) is a fluorescent chemical compound that can re-emit light upon light excitation. Examples of fluorophores include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, inorganic fluorescent labels such as particles based on semiconductor material like coated CdSe nanocrystallites.

Examples for fluorescent proteins include Exemplary fluorescent proteins include, e.g., Sirius, Azurite, EBFP, EBFP2, TagBFP, mTurquoise, ECFP, Cerulean, CyPet, TagCFP, mTFPI, mUkGI, mAGI, AcGFPI, TagGFP2, EGFP, GFP, mWasabi, EmGFP, YFP, TagYPF, Ypet, EYFP, Topaz, SYFP2, Venus, Citrine, mKO, mK02, mOrange, mOrange2, TagRFP, TagRFP-T, mStrawberry, mRuby, mCherry, mRaspberry, mKate2, mPlum, mNeptune, mKalama2, T-Sapphire, mAmetrine, mKeima, UnaG, dsRed, eqFP611, Dronpa, KFP, EosFP, Dendra, and IrisFP.

Examples of enzymes used as enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO).

Examples of radioactive labels include radioactive isotopes of hydrogen, iodide, cobalt, selenium, tritium, carbon, sulfur and phosphorous. $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{m}In$, $^{123}I$, $^{125}I$, $^{131}I$, $^{153}Gd$, $^{169}Yb$, and $^{186}Re$.

A "chemical compound" can in general be any chemical compound that can be covalently linked to the tyrosine derivative attached to the polypeptide of the invention. In particular, the chemical compound can be a small molecule, a polymer, such as a synthetic polymer (PEG) or a therapeutic agent, such as a cytotoxic agent. As such, for example an antibody can be equipped by the means and methods of the present invention with a cytotoxic drug to become an antibody-drug conjugate (ADC). Of course, it is envisaged that a linker is conjugated to a tyrosine derivative and a cytotoxic drug, if necessary. However, the cytotoxic drug may also be conjugated to the tyrosine derivative without a linker. Examples of cytotoxic drugs are doxorubicin or derivatives thereof, maytansinoids, e.g. DM1 or DM4, auristatins, e.g. auristatin E or auristatin F, calicheamicins, CC-1065, duocarmycins, anthracyclines, pyrrolobentodiazepins, centanamycin, iriontecan metabolite (SN38).

Exemplary small molecules include hormones, nucleotides, amino acids, sugars, lipids and organic compounds having a molecular weight of less than 100 kD. In some embodiments, small molecules that are approved by the FDA can be preferred.

Exemplary polymers include peptides, oligonucleotides, and polymeric organic compounds. In particular, suitable polymers include, e.g., elastin-like polypeptides (ELP), polypeptide chains of varying length (e.g., XTEN® technology or PASylation®), and carbohydrates, such as hydroxyethyl starch (e.g., HESylation®), polysialic acid (e.g., PolyXen® technology) or polyethylene glycol (PEGylation®).

The term "nucleic acid" as used herein refers to a polymer of nucleotides linked together by phosphodiester bonds. The term in general includes any polynucleotide in any possible configuration, such as single stranded, double stranded, linear, circular or a combination thereof. Nucleic acids include, e.g., DNA molecules, RNA molecules, analogues of the DNA or RNA generated using nucleotide analogues, and aptamers. An aptamer is typically a nucleic acid molecule that is able to bind molecules such as peptides, proteins and low molecular weight compounds.

The invention additionally provides a pharmaceutical composition comprising the polypeptide of the invention. A pharmaceutical composition according to the present invention may further comprise one or more pharmaceutically acceptable carriers. In a specific embodiment, the term "pharmaceutically acceptable" means approved by a regulatory agency or other generally recognized pharmacopoeia for use in animals, and more particularly in humans. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. Particular exemplary pharmaceutically acceptable carriers include (biodegradable) liposomes; microspheres made of the biodegradable polymer poly(D,L-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable carriers and excipients are inter alia described in Remington's Pharmaceutical Sciences, 15$^{th}$ Ed., Mack Publishing Co., New Jersey (1991) and Bauer et al., Pharmazeutische Technologie, 5$^{th}$ Ed., Govi-Verlag Frankfurt (1997). See, e.g., Remington: The Science and Practice of Pharmacy, 21$^{st}$ edition; Lippincott Williams & Wilkins, 2005.

In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients.

The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition.

Pharmaceutical compositions of the invention comprise a therapeutically effective amount of the polypeptide of the invention and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration. A variety of routes are applicable for administration of the polypeptide of the invention, including, but not limited to, orally, topically, transdermally, subcutaneously, intravenously, intraperitoneally, intramuscularly or intraocularly. However, any other route may readily be chosen by the person skilled in the art if desired.

The pharmaceutical compositions can be used for the treatment of a wide variety of different diseases and disorders. Thus the invention also envisages methods of treatment comprising administering an inventive polypeptide to a subject in need thereof. The subject is typically a mammal, e.g., a human. In some embodiments the subject is a non-human animal that serves as a model for a disease or disorder that affects humans. The animal model may be used, e.g., in preclinical studies, e.g., to assess efficacy and/or determine a suitable dose. In some embodiments, an inventive protein is administered prophylactically, e.g., to a subject who does not exhibit signs or symptoms of the disease or disorder (but may be at increased risk of developing the disorder or is expected to develop the disease or disorder). In some embodiments an inventive protein is administered to a subject who has developed one or more signs or symptoms of the disease or disorder, e.g., the subject has been diagnose as having the disease or disorder. Optionally, the method comprises diagnosing the subject as having a disease or disorder for which the protein is an appropriate treatment. By "therapeutically effective amount" is meant an amount of the polypeptide of the invention that elicits a desired therapeutic effect. The exact amount dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art.

The pharmaceutical composition of the present invention may further comprise one or more additional therapeutic agents. Preferably, said agents are therapeutically effective for treatment of the respective disease.

Further, the invention relates to a diagnostic composition comprising the polypeptide of the invention. The diagnostic composition may comprise means for diagnosis, such as detection agents.

Also, a kit comprising means for performing the methods described herein is provided. The kit may comprise an expression vector which allows expression of a protein of interest fused at its C-Terminus to a recognition sequence for tubulin tyrosine ligase having, a tubulin tyrosine ligase and a tyrosine derivative and/or a buffer solution as described herein which can be used for the tyronisnation.

The term "expression vector" refers to a carrier nucleic acid molecule which has the ability to incorporate and transcribe heterologous nucleic acid sequences in a host, host cell or in vitro. Selection of appropriate expression or transcription vectors is within the knowledge of those skilled in the art. Many prokaryotic and eukaryotic expression vectors are commercially available. Examples of vectors used in the present invention include plasmids, viruses, phagemids, bacteriophages, retroviruses, cosmids or F-factors. Specific vectors may be used for specific host or host cell types. Numerous examples of vectors are known in the art and are commercially available (Sambrook and Russell, Molecular Cloning: A Laboratory Manual, 3rd edition (Jan. 15, 2001) Cold Spring Harbor Laboratory Press, ISBN: 0879695765). Examples of vectors commonly used with bacteria include the pET series (Novagen), pGEX series (Ge Healthcare), pBAD-series (Invitrogen). Examples of vectors in yeasts are the pPic series for *Pichia* (Invitrogen), the pKlac system from *Kluyveromyces lactis* (New England biolabs), *S. cereviseae* vectors (Patel et al. Biotechnol Lett. 2003 25(4):331-334) and the pYes system for *S. cereviseae* (Invitrogen). Examples of vectors for use in fungi are the pBAR series (described in Pall et al. 1993. Fungal Genetics Newsletter 40: 59-61). The pIEx plasmid based system (Merck) or the baculovirus based system (Merck) are two examples of systems useful for insect cells. Examples of vectors for use in insect cells include the tetracycline regulated systems pTet and pTre, the adenovirus-based system Adeno-X, the retrovirus-based system Retro-X (Clontech) and the pcDNA vectors (Invitrogen). The expression vector may be naturally-occurring or artificial, linear or circular. The vector may also contain an intron.

The present invention also provides a method for the production of a polypeptide comprising (a) introducing or adding at the C-terminus of a polypeptide a recognition sequence for tubulin tyrosine ligase;
(b) optionally contacting the polypeptide obtained in step (a) in the presence of tubulin tyrosine ligase and a tyrosine derivative under conditions suitable for the tubulin tyrosine ligase to tyrosinate said polypeptide with said tyrosine derivative; and
(c) optionally conjugating a moiety to said tyrosinated polypeptide obtained in step (b).

Step (c) of said method may also be seen as a preferred method step. Accordingly, said method of the present invention further comprises preferably step (c) conjugating a moiety to said tyrosinated polypeptide obtained in step (b).

The present invention, as an alternative to the afore described method, provides a method for the production of a polypeptide, comprising
(a') introducing or adding at the C-terminus of a polypeptide a recognition sequence for tubulin tyrosine ligase; and
(b') contacting the polypeptide obtained in step (a') in the presence of tubulin tyrosine ligase and a tyrosine derivative conjugated to a moiety under conditions suitable for the tubulin tyrosine ligase to tyrosinate said polypeptide with said tyrosine derivative conjugated to said moiety.

The introduction or addition of a recognition sequence for TTL at the C-terminus of a polypeptide is done as described herein. For example, such a recognition sequence may be introduced or added by genetic engineering or by synthesis, either chemical protein synthesis or via synthetic biology.

Several factors may affect the rate at which enzymatic reactions proceed: temperature, pH, enzyme concentration, substrate concentration, and the presence of any inhibitors or activators. In some embodiments, it is envisaged that a buffer containing a nucleoside triphosphate, such as ATP, potassium chloride, magnesium chloride, and a reducing agent such as DTT is employed in the method of the invention in order to provide suitable conditions suitable for the TTL to tyrosinate the polypeptide of the invention. Other exemplary conditions are described in Ruediger et al. (1994), loc. cit.

It is envisaged herein that the pH value in the method of the invention in order to provide suitable conditions for the TTL to tyrosinate the polypeptide of the invention is in the range of 5 to 9, preferably 5.5 to 8.5, even more preferably 6 to 8.

Furthermore, it is envisaged herein that the tyrosine derivative concentration in the method of the invention in order to provide suitable conditions for the TTL to tyrosinate the polypeptide of the invention may be in the range of 0.1 mM to 10 mM, preferably 0.25 mM to 5 mM, more preferably 0.5 mM to 3 mM, and even more preferably 1 mM to 2 mM.

It is also envisaged herein that the reaction temperature in the method of the invention in order to provide suitable conditions for the TTL to tyrosinate the polypeptide of the invention may be in the range of 1° C. to 70° C., preferably 5° C. to 65° C., more preferably 10° C. to 60° C., even more preferably 15° C. to 55° C., most preferably 19° C. to 43° C., and for example 19° C. to 37° C.

A suitable reaction time for the TTL to tyrosinate the polypeptide of the invention may be in the range of 5 minute to 4 hours, preferably 10 minutes to 3 hours, more preferably 1 hour to 3 hours.

The conjugation of a moiety to the tyrosine derivative of a tyrosinated polypeptide is done as described herein.

Also provided by the present invention is the use of tubulin tyrosine ligase for tyrosinating a polypeptide other than tubulin having at its C-terminus a recognition sequence for tubulin tyrosine ligase.

A method for installing a chemistry handle to the C-terminus of a polypeptide other than tubulin is also provided herein, said method comprising:

(a) providing a polypeptide having at its C-terminus a tubulin tyrosine ligase recognition sequence; and
(b) contacting the polypeptide of step (a) in the presence of tubulin tyrosine ligase and a tyrosine derivative containing an unnatural functional group for chemoselective or bioorthogonal modifications under conditions suitable for the tubulin tyrosine ligase to tyrosinate said polypeptide with said tyrosine derivative.

Said method may optionally further comprise the step of conjugating a moiety as described herein to said tyrosinated polypeptide obtained in step (b).

The present invention also provides the use of tubulin tyrosine ligase for installing a chemistry handle to the C-terminus of a polypeptide other than tubulin, said polypeptide having at its C-terminus a tubulin tyrosine ligase recognition sequence.

The embodiments and definitions of terms described in the context of the means such as polypeptides of the invention are equally applicable to the methods and uses described above, mutatis mutandis.

EXAMPLES

Example 1: General Information

Analytical HPLC was conducted on a SHIMADZU HPLC system (Shimadzu Corp., Kyoto, Japan) with a SIL-20A autosampler, 2 pumps LC2 AAT, a 2489 UV/Visible detector, a CTO-20A column oven and an RF-10 A X2 fluorescence detector using an Agilent Eclipse C18 5 µm, 250×4.6 mm RP-HPLC-column with a flow rate of 0.5 mL/min. The following gradient was used: Method A: (A=$H_2O$+0.1% TFA, B=MeCN+0.1% TFA) 35% B, 0-15 min, 10-100% B 15-17 min, 100% B 17-22 min, 100-35% B 22-25 min and 35% B 25-30 min. UV chromatograms were recorded at 220 nm and fluorescence spectra with Ex/Em 495/517 were recorded.

Analytical UPLC:

UPLC-UV traces were obtained on a Waters H-class instrument equipped with a Quaternary Solvent Manager, a Waters autosampler and a Waters TUV detector connected to a 3100 mass detector with an Acquity UPLC-BEH C18 1.7 µm, 2.1×50 mm RP column with a flow rate of 0.6 mL/min. The following gradient was used: Method B: (A=$H_2O$+0.1% TFA, B=MeCN+0.1% TFA) 5-95% B 0-3 min, 95% B 3-5 min. UPLC-UV chromatograms were recorded at 220 nm.

Preparative HPLC was performed on a Gilson PLC 2020 system (Gilson Inc., WI, Middleton, USA) using a Macherey-Nagel Nucleodur C18 HTec Spum column (Macherey-Nagel GmbH & Co. Kg, Düren, Germany). The following gradient was used: Method C: (A=H2O+0.1% TFA, B=MeCN+0.1% TFA) flow rate 32 mL/min, 10% B 0-5 min, 10-100% B 5-35 min, 100% B 35-40 min. Method D: (A=H2O+0.1% TFA, B=MeCN+0.1% TFA) 10% B 0-5 min, 10-100% B 5-50 min, 100% B 50-55 min.

Analytical HPLC-MSMS:

Peptides were analyzed by a Ultimate 3000 nanoLC system (Thermo Scientific, Waltham, Mass., USA) connected to an LTQ Orbitrap XL mass spectrometer (Thermo Scientific). LC separations were performed on a capillary column (Acclaim PepMap100, C18, 3 µm, 100A, 75 µm i.d.×25 cm, Thermo Scientific) at an eluent flow rate of 300 nL/min. The following gradient was used: Method E: (A=H2O+0.1% formic acid, B=MeCN+0.1% formic acid) 3-50% B 0-50 min Mass spectra were acquired in a data-dependent mode with one MS survey scan with a resolution of 30,000 (LTQ Orbitrap XL) or 60,000 (Orbitrap Elite) and MS/MS scans of the five or 5 most intense precursor ions in the linear trap quadrupole, respectively.

Column chromatography was performed on silica gel (Acros Silica gel 60 Å, 0.035-0.070 mm).

High resolution mass spectra (HRMS) were measured on an Acquity UPLC system and a LCT Premier™ (Waters Micromass, Milford, Mass., USA) time-of-flight mass spectrometer with electrospray ionization using water and acetonitrile (10-90% gradient) with 0.1% formic acid as eluent.

NMR spectra were recorded with a Bruker Ultrashield 300 MHz spectrometer (Bruker Corp. Billerica, Mass., USA) at ambient temperature. The chemical shifts are reported in ppm relatively to the residual solvent peak.

Reagents and solvents were, unless stated otherwise, commercially available as reagent grade and did not require further purification. Resins and Fmoc-protected amino acids were purchased from IRIS BioTEch (Marktredwitz, Germany) or Novabiochem (Darmstadt, Germany).

SPPS was either carried out manually or with an Activo-P11 automated peptide synthesizer (Activotec, Cambridge, UK) via standard Fmoc-based conditions (Fast-moc protocol with HOBt/HBUT conditions).

Example 2: Synthesis of Tyrosine Derivatives 1, 2, 3, 4, and 5

Tyrosine derivates 1, 2, 3, 4 and 5

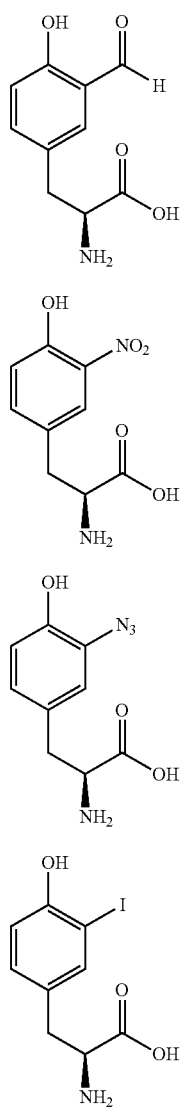

-continued

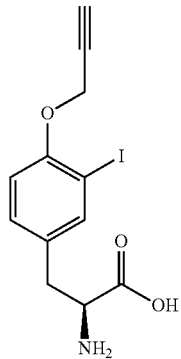

2.1 Synthesis of 3-formyl-L-tyrosine (1)

The synthesis of 1 was performed according to a known procedure in literature (Jung and Lavaroza (1997), J Org Chem, 62: 1553-1555; Banerjee et al. (2010), ACS chemical biology 5: 777-785).

Synthesis of 3-formyl-L-tyrosine (1).

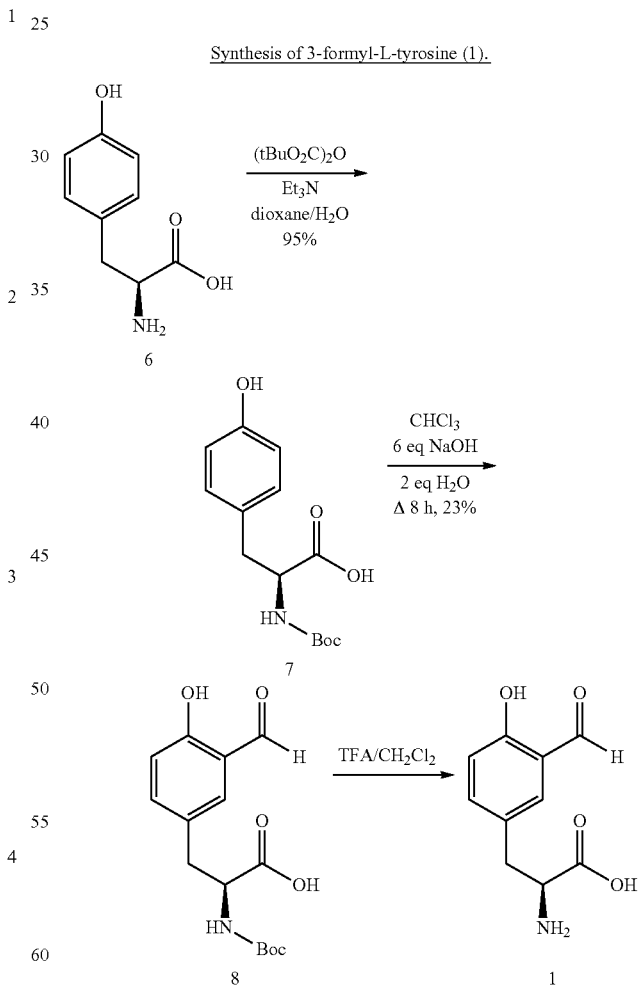

N-[(1,1-dimethylethoxy)carbonyl]-L-tyrosine (7)

To a solution of L-tyrosine (6, 1 g, 5.5 mmol) in 1/1 dioxane/water (50 mL), triethylamine (1.16 mL, 8.28 mmol)

was slowly added. The reaction was cooled to 0° C. with an ice/water bath and di-tert-butyl dicarbonate (1.32 g, 6.07 mmol) was added in two steps. After 1 h at 0° C., the temperature was slowly increased to ambient temperature and the mixture was stirred for further 24 h. Dioxane was removed under reduced pressure and the aqueous solution mixed with 25 mL saturated NaHCO$_3$, washed with ethyl acetated, acidified to pH 1 with 1N HCl, extracted with ethyl acetate and the organic extracts were washed with brine, dried over MgSO4 and evaporated to give N-Boc-L-tyrosine (7) as a white foam (1.471 g, 95%) which was used in the next step without further purification. Analytical data matched the literature (Jung and Lavaroza (1997), J Org Chem, 62: 1553-1555).

N-[(1,1-dimethylethoxy)carbonyl]-3-(3-formyl-4-hydroxyphenyl)-L-alanine (8)

To a suspension of 7 (2.00 g, 7.12 mmol) in chloroform (30 mL) and water (0.256 mL, 14.13 mmol) powdered sodium hydroxide (1.71 g, 42.72 mmol) was added and the mixture was refluxed for 4h. Two additional portions of powdered sodium hydroxide (each 0.42 g, 10.68 mmol) were added after 1 and 2 h. After 8 h at reflux, the reaction was cooled to ambient temperature, diluted with water and ethyl acetate (15 mL each), the organic layer discharged, the aqueous layer acidified to pH1 with 1 N HCl and back-extracted with ethyl acetate. The organic layers were washed with brine, dried over MgSO$_4$ and concentrated. Flash column chromatography (silica gel, 12/1 CHCl$_3$/MeOH, 1% acetic acid) gave compound 8 (0.49 g, 23%). Analytical data matched the literature (Jung and Lavaroza (1997), J Org Chem, 62: 1553-1555).

3-formyl-L-tyrosine (1)

Compound 8 (0.49 g, 1.6 mmol) was dissolved in 4 mL CH$_2$Cl$_2$. TFA (4 mL) was added slowly at 0° C. and the mixture was warmed to ambient temperature within 2 h. The solvent was removed at high vacuum. Preparative HPLC (method C) gave compound 1 as TFA salt (0.29 g, 80%, 18% TFA salt). The TFA salt content was determined by $^{19}$F NMR and tetrafluoroethylene as standard. $^1$H NMR (300 MHz, D$_2$O): δ 9.81 (s, 1H, CHO), 7.52 (d, J=2.4 Hz, 1H, CH$_{phenyl}$), 7.40 (dd, J=8.6, 2.3 Hz, 1H, CH 6.90 (d, J=8.6 Hz, 1H, CH$_{phenyl}$), 4.13 (t, J=6.6 Hz, 1H, CH), 3.15 (m, 2H, CH$_2$). $^{13}$C NMR (75 MHz, D$_2$O): δ 197.18, 171.68, 159.21, 138.07, 134.02, 126.03, 120.97, 117.73, 54.18, 34.48.

2.2 Synthesis of 3-nitro-L-tyrosine (2) and 3-azido-L-tyrosine (3)

Synthesis of tyrosine derivate 2 and 3.

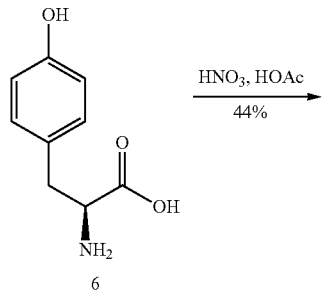

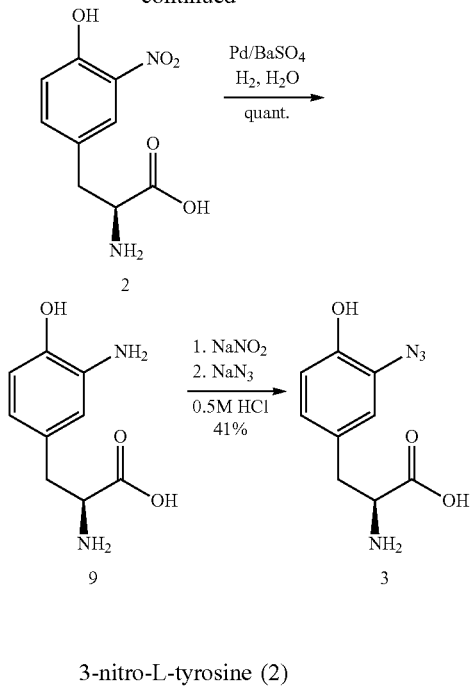

3-nitro-L-tyrosine (2)

L-tyrosine (6, 2.00 g, 11 mmol) was added to 10 mL HOAc, the suspension cooled to 0° C. and HNO$_3$ (1.47 mL, 11 mmol, 7.5 N) was slowly added. As soon as 6 dissolved completely (after 4h), the reaction was stopped by adding 2.5 mL H$_2$O followed by neutralisation with 25% NH$_3$ solution. The resultant solution was filtrated, the filtrate lyophilized and subjected to HPLC purification (method C) to give compound 2 as TFA salt (1.38 g, 44%, 51% TFA salt). The TFA salt content was determined by $^{19}$F NMR and tetrafluoroethylene as standard. $^1$H NMR (300 MHz, D$_2$O): δ 7.89 (d, J=2.3 Hz, 1H, CH$_{phenyl}$), 7.43 (dd, J=8.7, 2.3 Hz, 1H, CH$_{phenyl}$), 7.03 (d, J=8.7 Hz, 1H, CH$_{phenyl}$), 4.18 (t, J=6.6 Hz, 1H, CH), 3.31-3.04 (m, 2H, CH$_2$). $^{13}$C NMR (75 MHz, D$_2$O): δ 171.11, 152.74, 138.21, 133.85, 126.40, 125.76, 120.19, 53.68, 34.23.

3-amino-L-tyrosine (9)

Compound 2 (1.38 g, 4.86 mmol) was dissolved in 100 mL H$_2$O and 500 μL conc. HCl. The solution was supplemented with Pd/BaSO$_4$ (40 mg, 5% catalyst loading) and the mixture incubated at ambient temperature for 12 h under H2 atmosphere. After filtration of the catalyst and removal of the solvent in vacuo, the product 9 was obtained in quantitative yield as TFA salt (18% TFA salt content). The TFA salt content was determined by $^{19}$F NMR and tetrafluoroethylene as standard. $^1$H NMR (300 MHz, D$_2$O): δ 7.42-7.15 (m, 2H, CH$_{phenyl}$), 7.05-6.89 (m, 1H, CH$_{phenyl}$), 4.11 (t, J=6.5 Hz, 1H, CH), 3.24-3.06 (m, 2H, CH$_2$). $^{13}$C NMR (75 MHz, D$_2$O): δ 171.91, 149.37, 131.23, 126.32, 124.68, 117.84, 116.79, 54.47, 34.61.

3-azido-L-tyrosine (3)

3-amino-L-tyrosine (9, 0.696 g, 3.21 mmol) was dissolved in 6 mL 0.5 M HCl and a solution of NaNO$_2$ (0.221 g, 3.21 mmol) in 1 mL ice-cold H$_2$O was slowly added at 0° C. After 20 minutes, 3 mL of a solution of NaN$_3$ (0.560 g, 8.62 mmol) in H$_2$O were added within 30 minutes and stirred at 0° C. for another 8 h. The grey precipitate was isolated and purified by preparative HPLC (method C) to give pure compound 3 (0.290 g, 41%). ¹H NMR (300 MHz, D₂O): δ 6.95 (d, J=2.0 Hz, 1H, CH$_{phenyl}$) 6.89-6.79 (m, 2H, CH$_{phenyl}$), 4.06 (t, J=6.5 Hz, 1H, CH), 3.19-2.95 (m, 2H, CH₂). ¹³C NMR (75 MHz, D₂O): δ 172.04, 146.44, 127.24, 127.07, 126.58, 120.38, 116.86, 54.51, 34.83

2.3 Synthesis of 3-Iodo-L-tyrosine (4)

The synthesis of 4 was performed according to a known procedure in literature (Cochrane et al. (2012), Org. Lett., 14: 2402-2405.

L-tyrosine (6, 5.00 g, 27.5 mmol) was dissolved in conc. NH₄OH (500 mL) and cooled to 0° C. Iodine (7.00 g, 27.5 mmol) was dissolved in ethanol (95%, 100 mL) and added dropwise within 1 h to the tyrosine solution and stirred for 2 additional hours. The solution was concentrated to a volume of approx. 150 mL. It was acidified to pH 4.5 and cooled to 0° C. After one hour at 0° C., the formed crystals were collected and stirred in acetone for two hours. The product was collected to yield 4 as a grey solid (5.40 g, 63%). ¹H NMR (300 MHz, D₂O): δ 7.58 (d, J=2.3 Hz, 1H, CH$_{phenyl}$), 7.06 (dd, J=8.4, 2.2 Hz, CH$_{phenyl}$), 6.81 (d, J=8.3 Hz, CH$_{phenyl}$) 4.01 (t, J=6.5 Hz, 1H, CH), 3.14-2.90 (m, 2H, CH₂). ¹³C NMR (75 MHz, D₂O): δ 172.26, 154.56, 139.81, 130.69, 115.29, 83.67, 75.88, 34.26.

2.4 Synthesis of O-Propargyl-L-Tyrosine (5)

The synthesis of 5 was performed according to a known procedure in literature (Milles et al. (2012), JAGS., 134: 5187-5195.

Synthesis of tyrosine derivate 5.

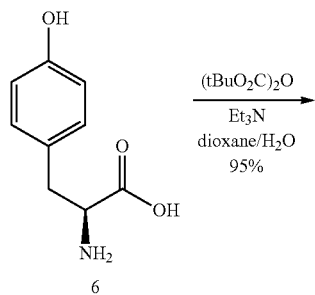

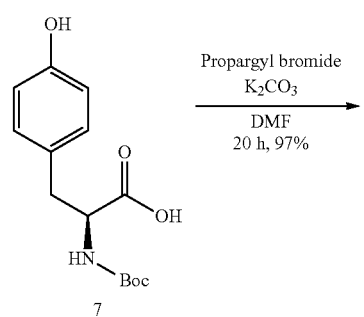

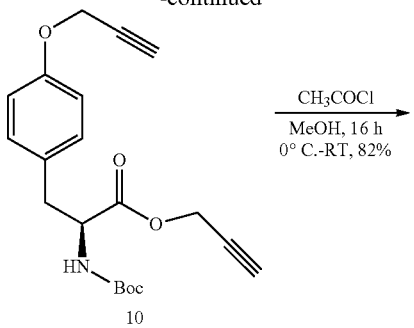

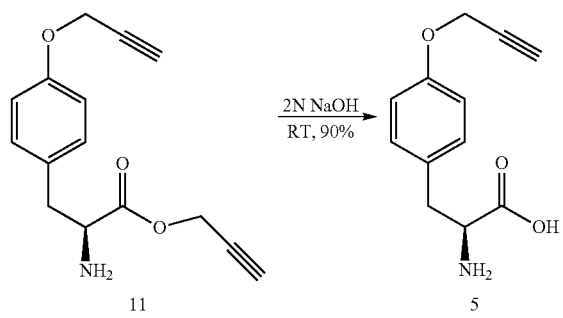

Intermediate 10

7 (5.02 g, 17.8 mmol) and K₂CO₃ (7.39 g, 53.5 mmol) were suspended in dry DMF (30 mL).

Propargylbromide (80% in toluene; 5.76 mL, 53.5 mmol) was added dropwise and the reaction mixture was stirred at room temperature for 20 hours. H₂O (100 mL) and Et²O (100 mL) were added and the two phases separated. The aqueous layer was extracted with Et₂O, the combined org. phases dried over MgSO₄ and evaporated to yield 10 as a yellow oil which was used in the next step without further purification (6.02 g, 94%).

Intermediate 11

Acetyl chloride (7.27 g, 6.58 mL, 92.6 mmol) was slowly added to anhydrous methanol (55 mL) at 0° C. This mixture was then added to compound 10 (6.02 g, 16.86 mmol), allowed to warm to ambient temp. And stirred for additional 16 hours. All volatile components were removed in vacuum to give HCl salt of 11 as a white solid which was used in the next step without further purification (4.01 g, 80%).

O-propargyl-L-tyrosine (5)

11 (4.01 g, 13.63 mmol) was dissolved in methanol (15 mL) and aqueous 2N NaOH (20 mL) was added slowly. The mixture was acidified carefully with conc HCl to pH 3 and kept overnight at 4° C. A white precipitate formed which was filtered off and dried in the vacuum to yield the HCl-salt of compound 5 (3.05 g, 88%). ¹H NMR (300 MHz, DMSO-d₆): δ 7.20 (d, J=8.2 Hz, 2H, CH$_{phenyl}$), 6.90 (d, J=8.3 Hz, 2H, CH$_{phenyl}$), 4.75 (d, J=2.4 Hz, 2H, CH₂), 3.56 (t, J=2.4 Hz, 1H, CH), 3.45 (dd, J=7.8, 4.6 Hz, 1H, CH), 3.08 (dd, J=14.4m 4.6 Hz, 1H, CH), 2.85 (dd, J=14.4, 7.9 Hz, 1H, CH).

2.5 Synthesis of 3-(N-iminoacetyl-N'-D-biotinyl-3,6-dioxaoctane,1,8-diamine)-tyrosine (12)

Synthesis of derivate 13.

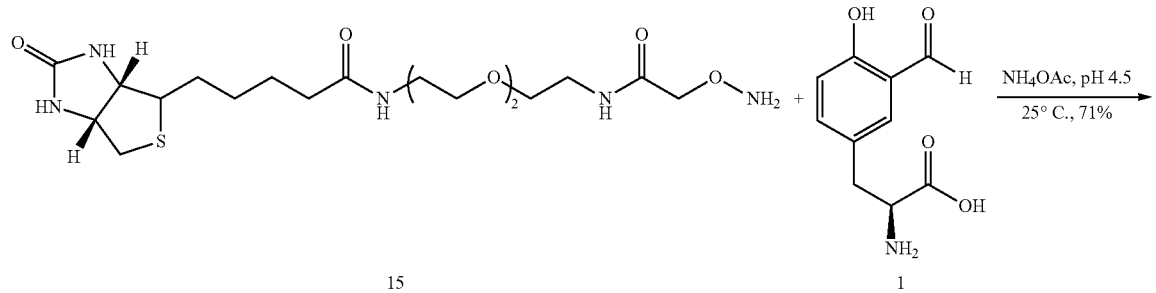

15      1

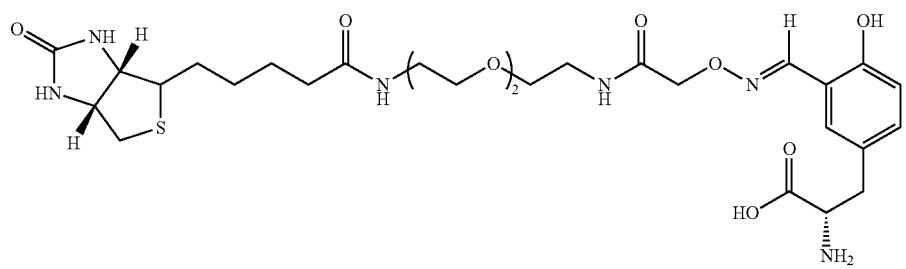

12

Biotin-hydroxylamine (20 mg, 0.04 mmol) was dissolved in 1 mL NH$_4$OAc pH 4.5, 3-formyl-L-tyrosine 1 was added (9.34 mg 0.04 mmol) and the solution incubated at 37° C., 200 rpm for 4 h. The reaction mixture was purified by preparative HPLC (method D). The oxime 12 was obtained with a yield of 71% (20 mg, 0.03 mmol). $^1$H-NMR (300 MHz, D$_2$O): δ 8.38 (s, 1H, ONCH), 7.24 (d, J=2.2 Hz, 1H, CH$_{phenyl}$), 7.17 (dd, J=8.5, 2.2 Hz, 1H, CH$_{phenyl}$), 6.87 (d, J=8.4 Hz, 1H, CH$_{phenyl}$), 4.59 (s, 2H, COCH$_2$O), 4.47-4.41 (m, 1H, CH), 4.27-4.21 (m, 1H, CH), 4.15 (t, J=6.2 Hz, 1H, CH), 3.54-3.45 (m, 4H OCH$_2$CH$_2$O), 3.41-3.32 (m, 6H, CH$_2$O, CH$_2$NH), 3.21-3.00 (m, 5H, CH$_2$NHboc, CH, CH$_2$), 2.83 (dd, J$_1$=13, J$_2$=4.9, Hz 1H, CHH$_{exo}$S), 2.63 (d, J=13 Hz, 1H, CHH$_{endo}$S), 2.10 (t, J=7.2 Hz, 2H, CH$_2$CO), 1.63-1.32 (m, 4H, CH$_2$), 1.32-1.20 (m, 2H, CH$_2$).

Example 3: Synthesis of Peptide CF-Tub-Tag (13)

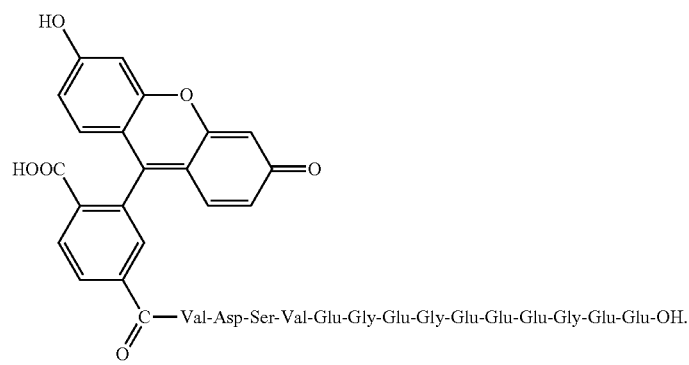

13

5(6)-carboxyfluorescein labelled peptide 13 (SEQ ID No. 3)

Peptide 8 (SEQ ID No. 3) was synthesized by standard Fmoc-based chemistry in a linear synthesis on an Activotec peptide synthesizer followed by manual coupling of 5(6)-carboxyfluorescein. 0.1 mmol of Fmoc-L-Glu(tBu)-Wang resin (subst: 0.58 mmol/g) was added to a reaction vessel and synthesis performed with five-fold amino acid excess. Coupling was achieved by HOBt/HBTU/DIPEA addition. After the final amino acid coupling, the fluorophore was coupled in a double coupling procedure with 5 eq of 5(6)-carboxyfluorescein, HOBt, HBTU and DIPEA in DMF for 1 h. The peptide was cleaved off the resin by addition of TFA/DTT/Tis/thioanisol (95/2/2/1) in 4 h. Subsequently, the cleavage cocktail was evaporated by $N_2$-flow and the peptide was precipitated by the addition of ice-cold diethyl ether. The precipitate was spun down, dissolved in water and acetonitrile and purified by preparative HPLC (method D). The peptide was obtained with a yield of 8% (16 mg, 8 µmol); molar mass peptide=1850.6 Da; HRMS: m/z: 926.3065 $[M+2H]^{2+}$ (calc. m/z: 926.3165).

Example 4: TTL Expression and Purification

TTL (*Canis lupus*) having NCBI Accession number XP_540180.2 was expressed in *E. coli* (BL21DE3) as Sumo-TTL fusion protein with an N-terminal His-Tag. Cells were induced with 0.5 mM IPTG and incubated at 18° C. for 18 h. Lysis was performed in presence of Lysozyme (100 µg/ml), DNAse (25 µg/ml) and PMSF (2 mM) followed by sonification (Branson® Sonifier; 16×8 sec, 20% Amplitude) and debris centrifugation at 20.000 g for 30 min. His-Sumo-TTL was purified using a 5 ml His-Trap. For removal of the Sumo-Tag, peak fractions were incubated with SenP2 protease at 4° C. overnight. A second His-Trap run then removed the Sumo fraction. Purified protein was then desalted on a PD10 column (GE Healthcare); buffer was exchanged to MES/K pH 6.8 (20 mM MES, 100 mM KCl, 10 mM $MgCl_2$). Protein aliquots were shock-frozen and stored at −80° C. at 0.8 g/l.

Example 5: Determination of TTL Activity Using Carboxyfluorescein-Peptide 13

Tyrosination reactions were performed in a 250 µL solution consisting of 20 mM MES/K pH 7.0, 100 mM KCl, 10 mM $MgCl_2$, 2.5 mM ATP, 1 mM tyrosine derivative, 0.2 mM peptide, 1 µM TTL and 5 mM DTT in case of compound 1, 2, 4 and 5 or 5 mM reduced glutathione in case of compound 3, respectively. The mixture was incubated at 37° C. and several aliquots (25 µL) were taken within 24 h, mixed with equal volumes of $H_2O$+0.1% TFA and subjected either to isocratic analytical HPLC equipped with a fluorescence detector (Method A) or analytical UPLC-MS analysis. Quantities of substrate and product peptides were estimated from the corresponding peak-area in the fluorescence or UV detection spectrum (Ex/Em: 495/517).

Example 6: Cloning

A nanobody was equipped with a C-terminal TTL derived tag (Tub-tag) and an N-terminal 6×His-Tag. The DNA coding sequence of the Tubulin A1A derived Tub-tag peptide VDSVEGEGEEEGEE (SEQ ID No: 3) was added to the Nanobody sequences via PCR using Forward Primer 5'-GGGGCCATGGCCCATCATCACCATCACCATGAT-GTGCAGCTGCAGGAGTCT GGGGGAG-3' (SEQ ID NO: 9) and Reverse Primer 5'-CCCCGAATTCTTATTCT-TCGCCTTCTTCTTCGCCT TCGCCTTCCACGCTATC-CACTGAGGAGACGGTGACC-3' (SEQ ID NO: 10) and subcloned into pHen6 bacterial expression vector using NcoI and EcoRI restriction sites. Positive clones were verified by DNA sequencing.

Example 7: Nanobody-Tub-Tag Expression and Purification

Nanobody-Tub-tag fusion proteins were expressed in *E. coli* (JM109). Cells were induced with 0.5 mM IPTG and incubated at 18° C. for 18 h. Lysis was performed in presence of Lysozyme (100 µg/ml), DNAse (25 µg/ml) and PMSF (2 mM) followed by sonification (Branson® Sonifier; 16×8 sec, 20% Amplitude) and debris centrifugation at 20.000 g for 30 min. The protein was purified with an Äkta FPLC system using a 5 ml His-Trap (GE Healthcare) column, peak fractions were concentrated to 2 ml using Amicon filter columns (Cut-off 3 kDa; (Millipore)) and subjected to size exclusion chromatography using a Superdex 75 column (GE Healthcare). Peak fractions were pooled and protein aliquots were shock-frozen and stored at −80° C. at 0.5 g/l. Note: Tub-tag is shown in SEQ ID No. 3.

Example 8: Ligation of Tyrosine Derivatives to Modified Nanobodies

See FIG. 24

Tyrosination reactions were performed in a 50 µL solution consisting of 20 mM MES/K pH 7.0, 100 mM KCl, 10 mM $MgCl_2$, 2.5 mM ATP, 1 mM tyrosine derivative, 1 µM TTL, 5 µM nanobody and 5 mM reduced glutathione in case of azide containing compounds or 5 mM DTT in case of other tyrosine derivatives, respectively. The mixture was incubated at 37° C. for 1-3 h.

8.1 Tryptic Digest and MSMS Analysis of Tyrosinated Nanobodies

Nanobodies were tyrosinated as described in Example 8. Proteins were separated by SDS-PAGE. Protein bands of interest were excised, soaked with 100 µL 50 mM $(NH_4)_2CO_3$/ACN 1:1 and incubated at 30° C. for 10 min. The supernatant was removed and the gel pieces were incubated in 50 mM $(NH_4)_2CO_3$ at 30° C. for further 10 min. The two incubation steps were repeated until the pieces were colorless. Hereafter, the gel pieces were dehydrated by the addition of 25 µL ACN, the supernatant removed and the gels were dried under reduced pressure. In-gel digest was performed in a total volume of 20 µL 50 mM $(NH_4)_2CO_3$ at 37° C. for 12 h using 0.05 µg Trypsin. 20 µL ACN+0.5% TFA were added, the mixture was incubated in an ultrasonic bath, the supernatant transferred to LC glass vials, the solvent was removed under reduced pressure and the residual peptides resuspended in 6 µL 95% $H_2O$+0.1% TFA, 5% ACN+0.1% TFA solution. Peptides were separated by HPLC and analysed by MSMS experiments.

8.2 Bioorthogonal Labeling of Tyrosinated Nanobodies: Biotin Labeling

See FIG. 25

Nanobodies were tyrosinated as described in Example 8, above. The reaction mixtures were rebuffered to 100 mM $NH_4OAc$, 100 mM NaCl pH 5.4 (in case of reaction with biotin-hydroxylamine) or Dulbecco's PBS pH 7.4 (in case of biotin-phosphines and biotin-dibenzylcyclooctynes) and incubated with 20-40 eq of biotin derivative at 20° C. -37° C. for 4-12 h. Proteins were separated by SDS-PAGE and wet blotted onto a nitrocellulose membrane using a Bio-Rad Mini-Protean Tetra System (250 mA, 1 h). The membrane was blocked with Roti-Block (Carl Roth, Karlsruhe, Germany) for 1 h at ambient temperature and incubated for 1 h with streptavidin peroxidase conjugate (Merck Millipore, Darmstadt, Germany) (1:2000) at ambient temperature. Immunodetection was performed with WesternBright chemiluminescence solution (Western Bright ECL, Biozym Scientific, Hessisch Oldendorf, Germany) and a Chemi-Doc™ XRS+ gel imaging system (Bio-Rad, Hercules, Calif., US).

Labelling with Fluorophores Alexa594®-Hydrazide Cy5-dibenzylcyclooctyne and Cy5-alkyne See FIG. 26

Nanobodies were tyrosinated as described in Example 8, above. The reaction mixtures were rebuffered to 100 mM $NH_4OAc$, 100 mM NaCl pH 6.0 (in case of reaction with Alexa594®-hydrazides) or Dulbecco's PBS pH 7.4 (in case of Cy5-dibenzylcyclooctynes) and incubated with 30 eq of fluorophore at 20° C. -37° C. for 4-12h. In case of Cy5-alkyne, the reaction mixture was rebuffered 0.38 mmol $K_2HPO_4$ at pH 7.0 and 30 eq. fluorophore added. A aqueous solution of 0.1 eq $Pd(OAc)_2[DMADHP]_2$ and 0.2 eq sodium-ascorbate was incubated at 37° C. for 10 minutes and added to the protein mixture which was further incubated at 37° C. for 4h. Proteins were separated by SDS-PAGE and visualized by a ChemiDoc™ MP gel imaging system (Bio-Rad, Hercules, Calif., US) and a Fuji FLA-5000 laser imager (Alexa594®: 532 nm excitation, Cy5: 634 nm excitation, LPG-filter)(Fujifilm, Tokyo, Japan).

Pegylation by Staudinger-Phosphite Reaction

Nanobodies were tyrosinated as described in Example 8, above. The reaction mixtures were rebuffered to 50 mM Tris, 100 mM KCl pH 8.5 and incubated with 40 eq. of tris (PEG750)phosphite at 37° C. for 24h. Proteins were separated by SDS-Page. PEGylated nanobodies were wet blotted onto a nitrocellulose membrane using a Bio-Rad Mini-Protean Tetra System (250 mA, 1h). A monoclonal anti PEG-B-47 antibody (Ancam, UK) and a secondary Goat Anti-Rabbit IgG H&L (HRP) (Abcam, UK) were used for detection.

Example 9: One Step Labeling

See FIG. 27

Labeling reactions were performed in a 150 µL solution consisting of 20 mM MES/K pH 7.0, 100 mM KCl, 10 mM $MgCl_2$, 2.5 mM ATP, 1 mM tyrosine-biotin 12, 1 µM TTL, 5 µM nanobody and 5 mM DTT. The mixture was incubated at 37° C. for 20h. Proteins were separated by SDS-PAGE and wet blotted onto a nitrocellulose membrane using a Bio-Rad Mini-Protean Tetra System (250 mA, 1h). The membrane was blocked with Roti-Block (Carl Roth, Karlsruhe, Germany) for 1 h at ambient temperature and incubated for 1 h with streptavidin peroxidase conjugate (Merck Millipore, Darmstadt, Germany) (1:2000) at ambient temperature. Immunodetection was performed with WesternBright chemiluminescence solution (Western Bright ECL, Biozym Scientific, Hessisch Oldendorf, Germany) and a ChemiDoc™ XRS+ gel imaging system (Bio-Rad, Hercules, Calif., US). See FIG. 22.

Example 10: Abbreviations

Da Dalton
DIC diisopropylcarbodiimide
DI PEA diisopropylethylamine
DMADHP N,N-dimethyl-2-amino-4,6-dihydropyrimidine
DMF N,N-dimethylformamide
DTT dithiotreitol
eq equivalents
Em emission wavelength in nanometer
Ex excitation wavelength in nanometer
Fmoc fluorenylmethyloxycarbonyl
HBTU N,N,N',N'-Tetramethyl-O-(1H-benzotriazol-1-yl) uranium hexafluorophosphate
HOAc acetic acid
HOBt hydroxybenzotriazole
HPLC high performance liquid chromatography
HRMS high resolution mass spectrometry
LC liquid chromatography
MeCN acetonitrile
MHz megahertz
SDS-PAGE sodium dodecyl sulfate polyacrylamide gel electrophoresis
TFA trifluoroacetic acid
TIS triisopropylsilane
Tub-tag Tubulin derived TTL recognition sequence
Tub-tag labeling present invention
UPLC ultra performance liquid chromatography
UV ultraviolet Example 11: Versatile and Efficient Site-Specific Protein Functionalization by Tubulin Tyrosine Lipase Here we present a novel chemoenzymatic approach for simple and fast site-specific protein labeling. We repurposed tubulin tyrosine ligase (TTL) to attach various unnatural tyrosine derivatives as small bioorthogonal handles to recombinant proteins containing a short tubulin derived recognition sequence (Tub-tag). This novel strategy enables a broad range of chemoselective C-terminal protein modifications for applications in biochemistry, cell biology and beyond as demonstrated for the site-specific labeling of nanobodies.

Site-specific functionalization of proteins is crucial for a plethora of applications throughout the life sciences. Fluorescent proteins and self-labeling strategies like SNAP-[1] and HALO-[2] tagging have become indispensable tools for cell biologists to analyze intracellular activity and localize proteins of interest. The genetic fusion of GFP or self-labeling protein tags is straightforward, however, the size and biochemical nature of the attachment may affect the properties and application of the chimeric protein[3].

Protein trans-splicing, expressed protein ligation as well as amber suppression and auxotrophic expression in combination with bioorthogonal labeling[4] are prominent tools that allow the placement of small tags and modifications to proteins. However, low expression yields, the need of protein engineering and impaired protein folding are limiting factors of these techniques. In addition, chemoenzymatic approaches find increasing attention for the site-specific addressability of proteins using short and specific recognition tags in conjunction with respective enzymes such as trypsin[5], Sortase A[6], phosphopantetheinyl-transferase (PPTase)[7], biotin ligase[8], lipoic acid ligase[9], and formylglycine generating enzyme[10].

Together, these chemoenzymatic systems open up broad possibilities for subsequent chemoselective and site-specific labeling, but still have chemical limitations. These challenges include large and hydrophobic substrates for the enzymatic reaction that may affect the protein of interest (PPTase, lipoic acid ligase, biotin ligase). Moreover, reaction reversibility and product hydrolysis necessitate a high excess of catalyst and substrate (Sortase labeling, formyl-glycine generating enzyme, trypsin). In particular the targeted incorporation of unnatural functional groups often requires extensive enzyme engineering to improve the overall reaction efficiency.

Figure 1:
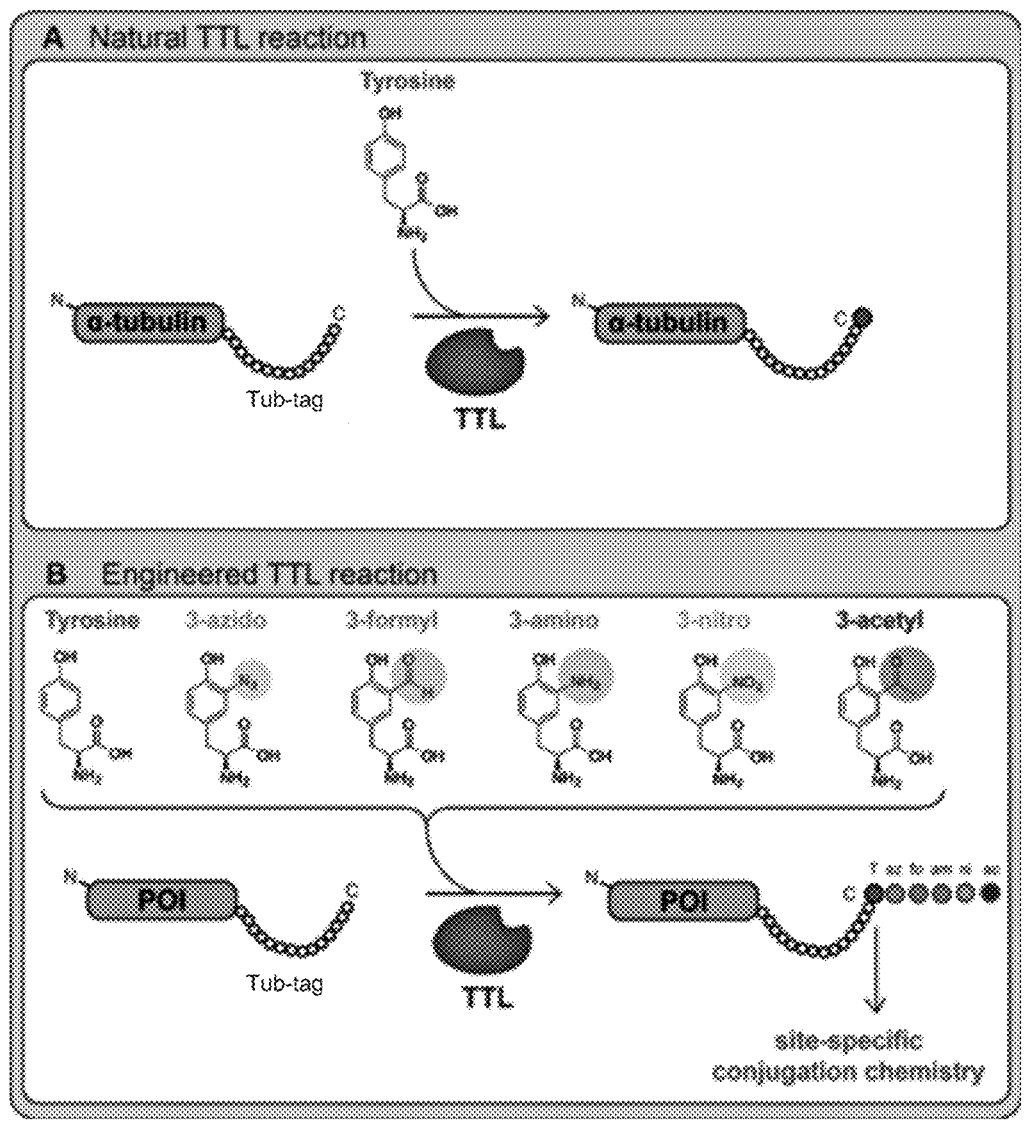
FIG. 1: Schematic illustration of the present invention. (A) Shown is the natural reaction of Tubulin tyrosination catalyzed by TTL. TTL interacts with a C-terminal TTL Reactive Motif (Tub-tag) and catalyzes the ligation of a C-terminal tyrosine. (B) Shown is the engineered reaction. The Tub-tag is recombinantly added to any protein of interest (POI). TTL catalyzes the C-terminal ligation of tyrosine and tyrosine derivatives that can be used for site-specific conjugation chemistry of any reactive molecule.
Figure 2:
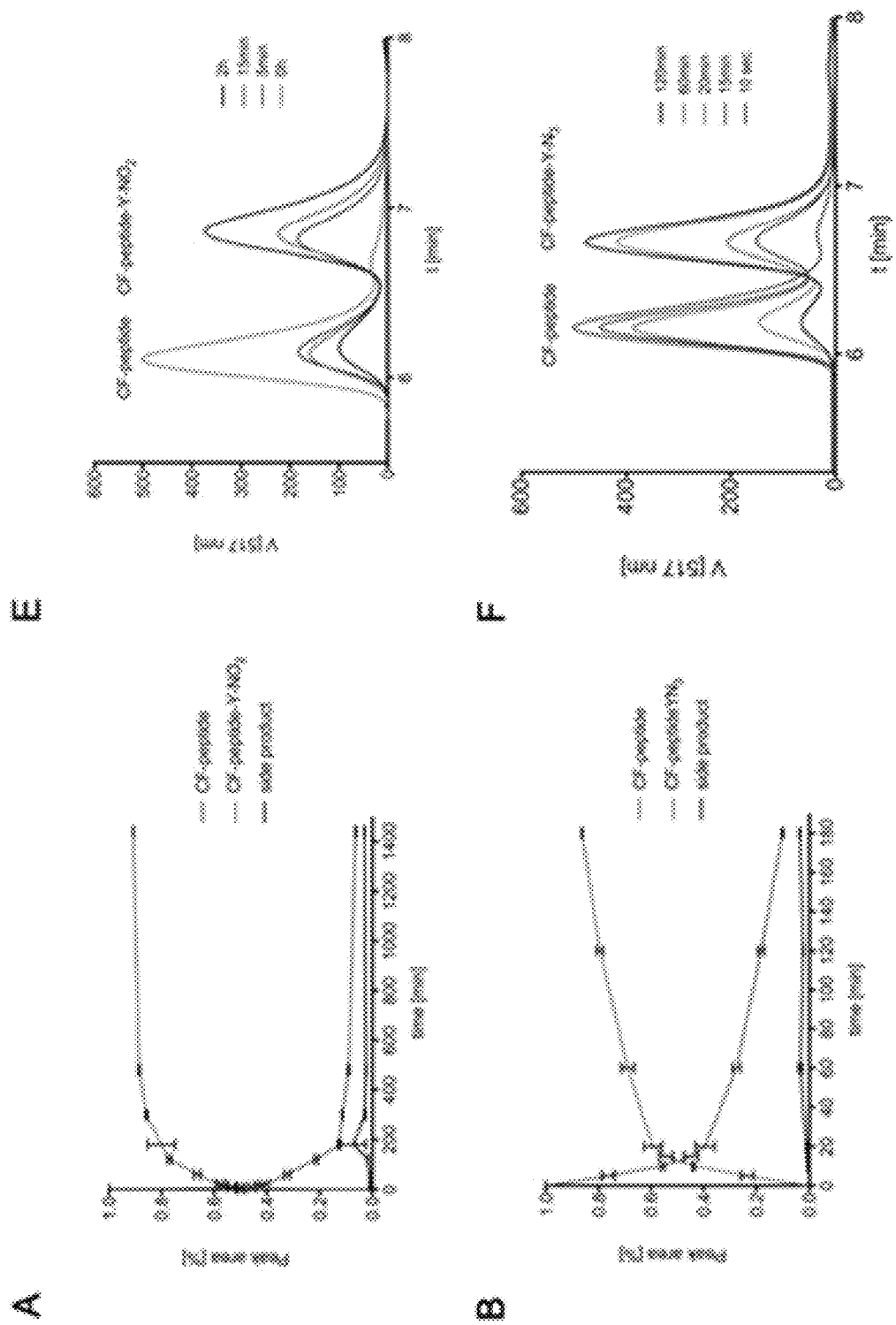
FIG. 2: C-terminal ligation of 3-nitro-tyrosine (A, E), 3-azide-tyrosine (B, F), 3-formyl-tyrosine (C, G) and 3-iodo-tyrosine (D, H) to the α-tubulin derived, 14mer peptide. (A, B, C, D) The red line represents the consumption of peptide, the blue line the formation of C-terminal functionalized peptide, the black line the formation of side product. The mean value of three replicate reactions is shown (SD). Quantitation of substrate and product was done via integration of peak. (E, F, G, H) HPLC-fluorescence traces that were taken at different time points of the TTL reaction with 3-nitro-tyrosine (E), 3-azide-tyrosine (F), 3-formyl-tyrosine (G) and 3-iodo-tyrosine and peptide are shown. The fluorescence peak corresponding to peptide (left) is getting smaller within time and a new peak, corresponding to C-terminal modified peptide, is appearing.
Figure 2:
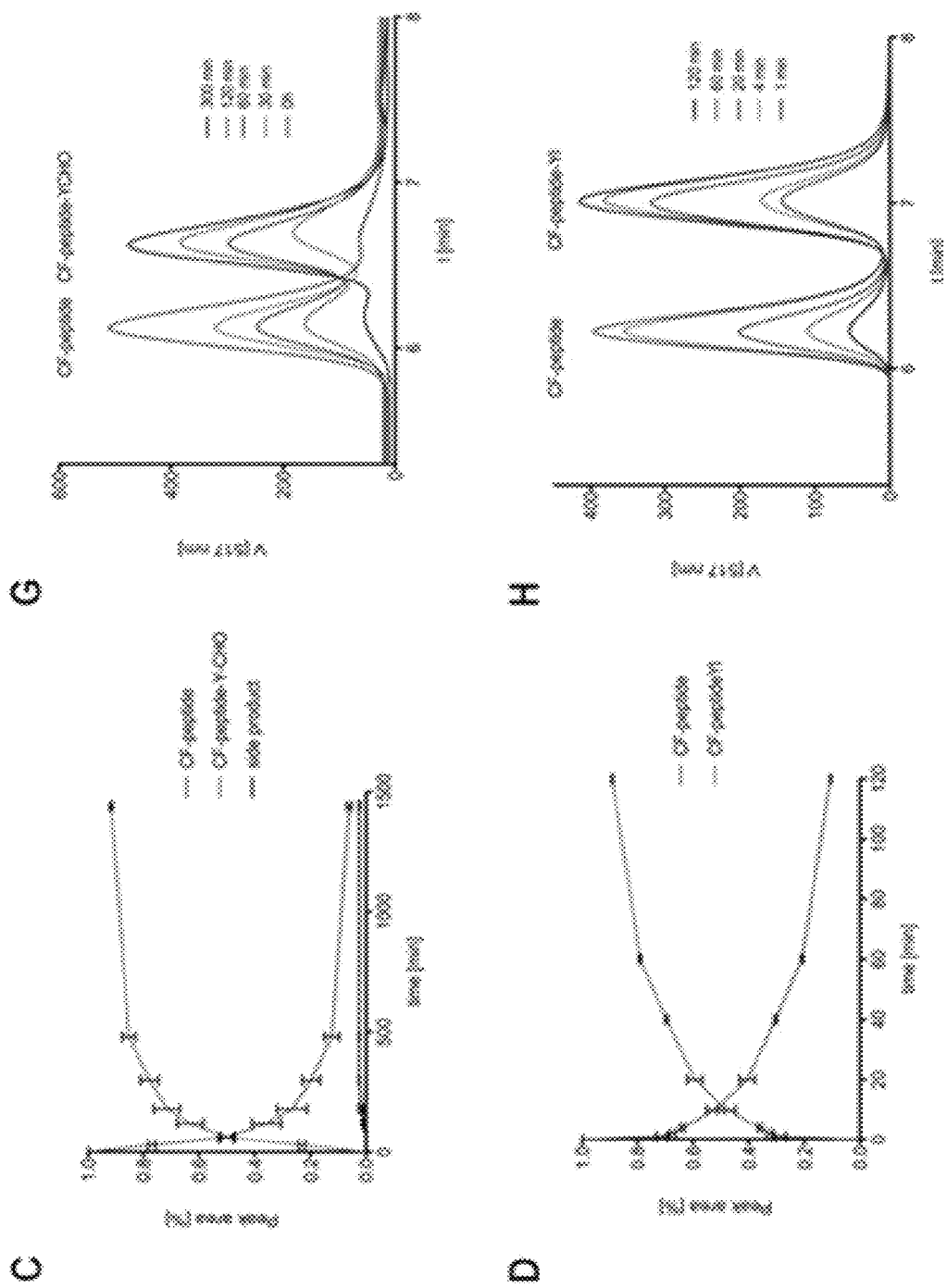
Figure 3:
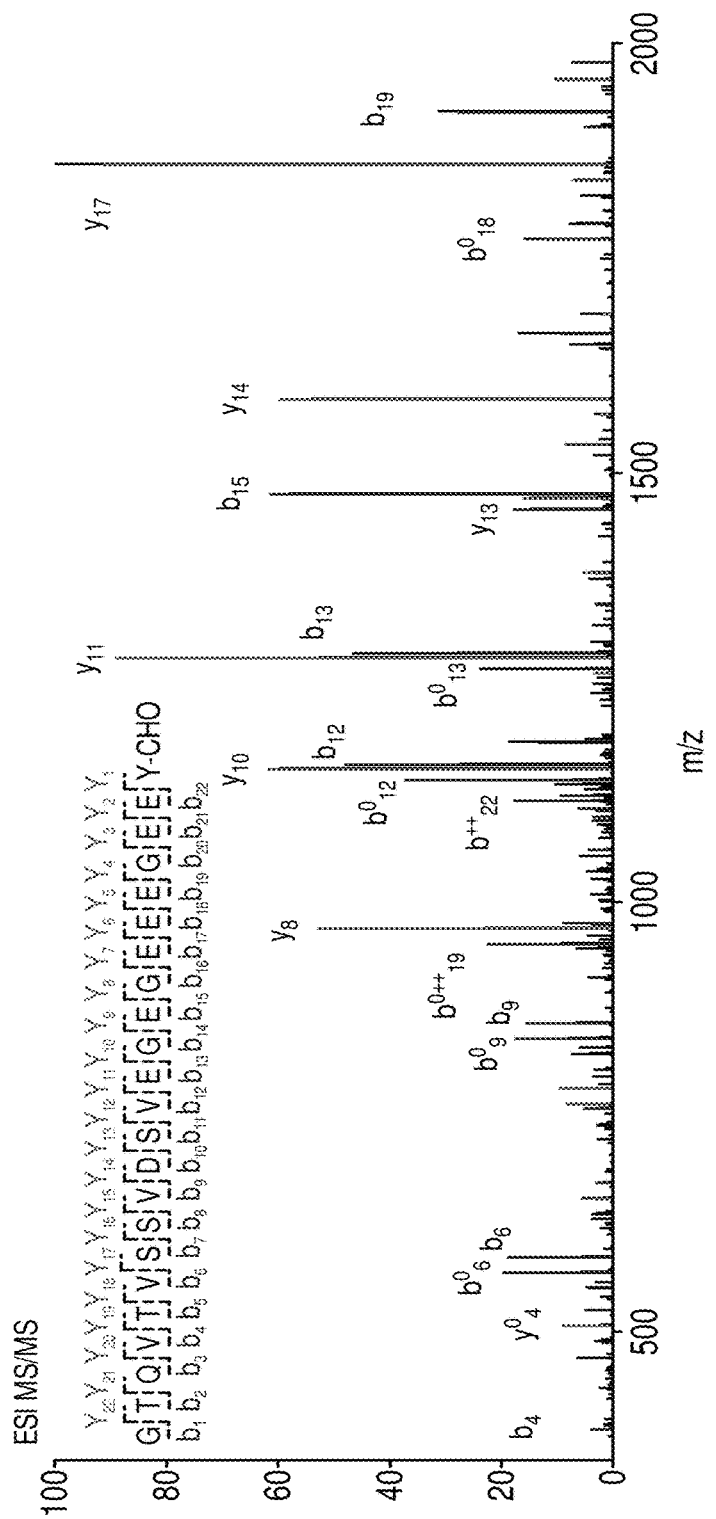
FIG. 3: Mass spectrometric validation of the C-terminal ligation of 3-formyl-tyrosine at the protein level (nanobody with C-terminal α-tubulin derived, 14mer peptide). An ESI MS/MS diagram of the nanobody after in gel digest using trypsin. The MS/MS diagram of the peptide carrying the terminal 3-formyl-tyrosine residue is shown.
Figure 4:
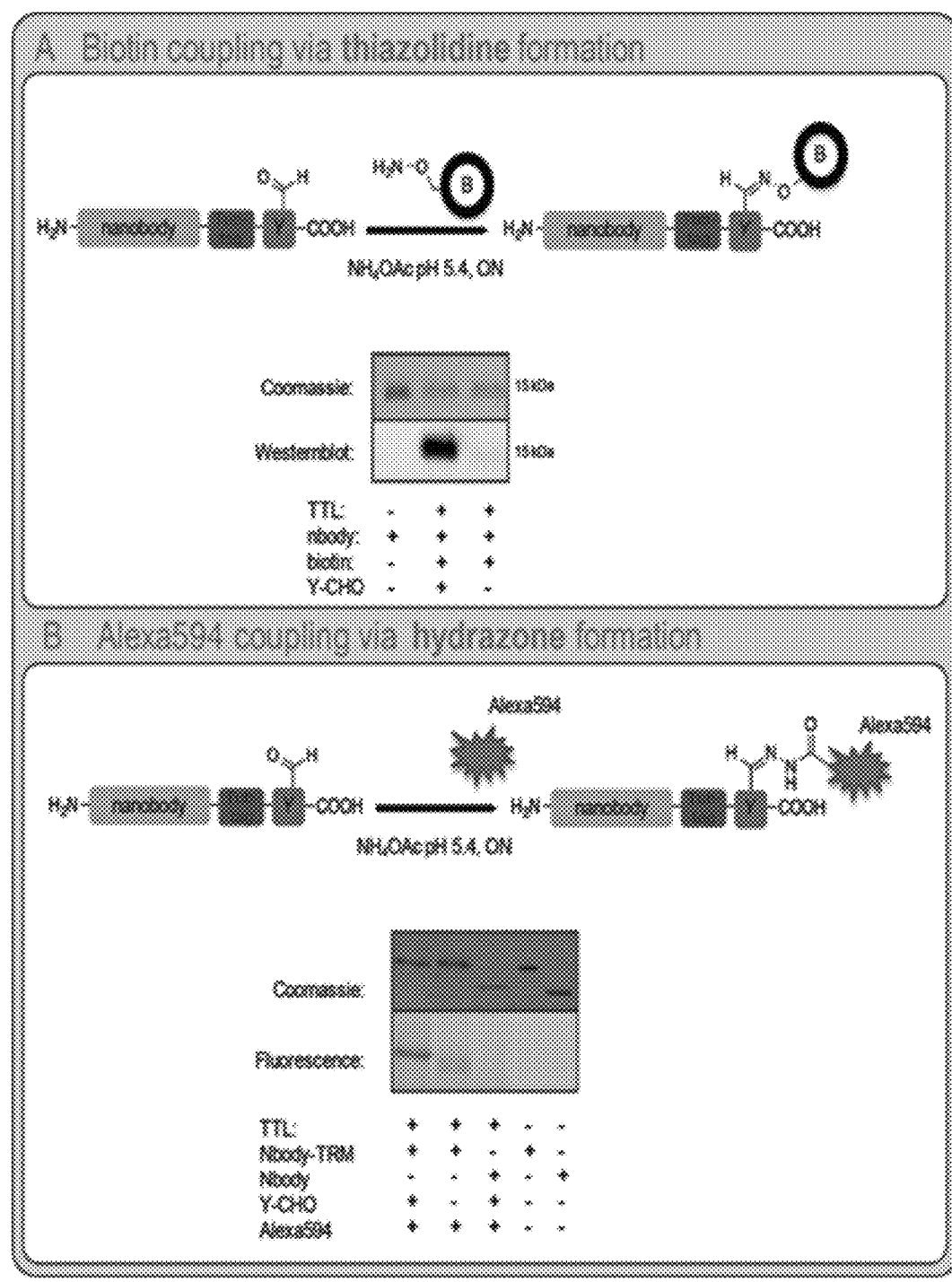
FIG. 4: (A) C-terminal attachment of a biotin-derivative to a nanobody by oxime forming reaction. 3-formyl-L-tyrosine was enzymatically incorporated to the C-terminus of the nanobody. Thus, the site-specifically incorporated aldehyde group was used to install biotin in an oxime forming reaction. The SDS-gel shows the untreated nanobody in lane 1, the reaction where the nanobody was incubated with TTL and 3-formyl-L-tyrosine (lane 2) and the reaction where the nanobody was incubated with TTL alone (lane 2). Following the enzymatic reaction, the samples were incubated with 20 eq. of the biotin. Selective labeling of the 3-formyl-L-tyrosine containing nanobody is shown. (B) C-terminal attachment of Alexa594 to a nanobody by hydrazone forming reaction. 3-formyl-L-tyrosine was enzymatically incorporated to the C-terminus of the nanobody. Thus, the site-specifically incorporated aldehyde group was used to install a fluorophore, namely Alexa594, in a hydrazone forming reaction. The SDS-gel shows the reaction of nanobody-Tub-tag with TTL and 3-formyl-L-tyrosine (lane 1), the reaction where nanobody-Tub-tag was incubated with TTL alone (lane 2) and the reaction where a nanobody without the Tub-tag peptide was used (lane 3). Following the enzymatic reaction, the three samples were incubated with 30 eq. of fluorophore. Selective labeling of the 3-formyl-L-tyrosine containing nanobody is shown.
Figure 5:
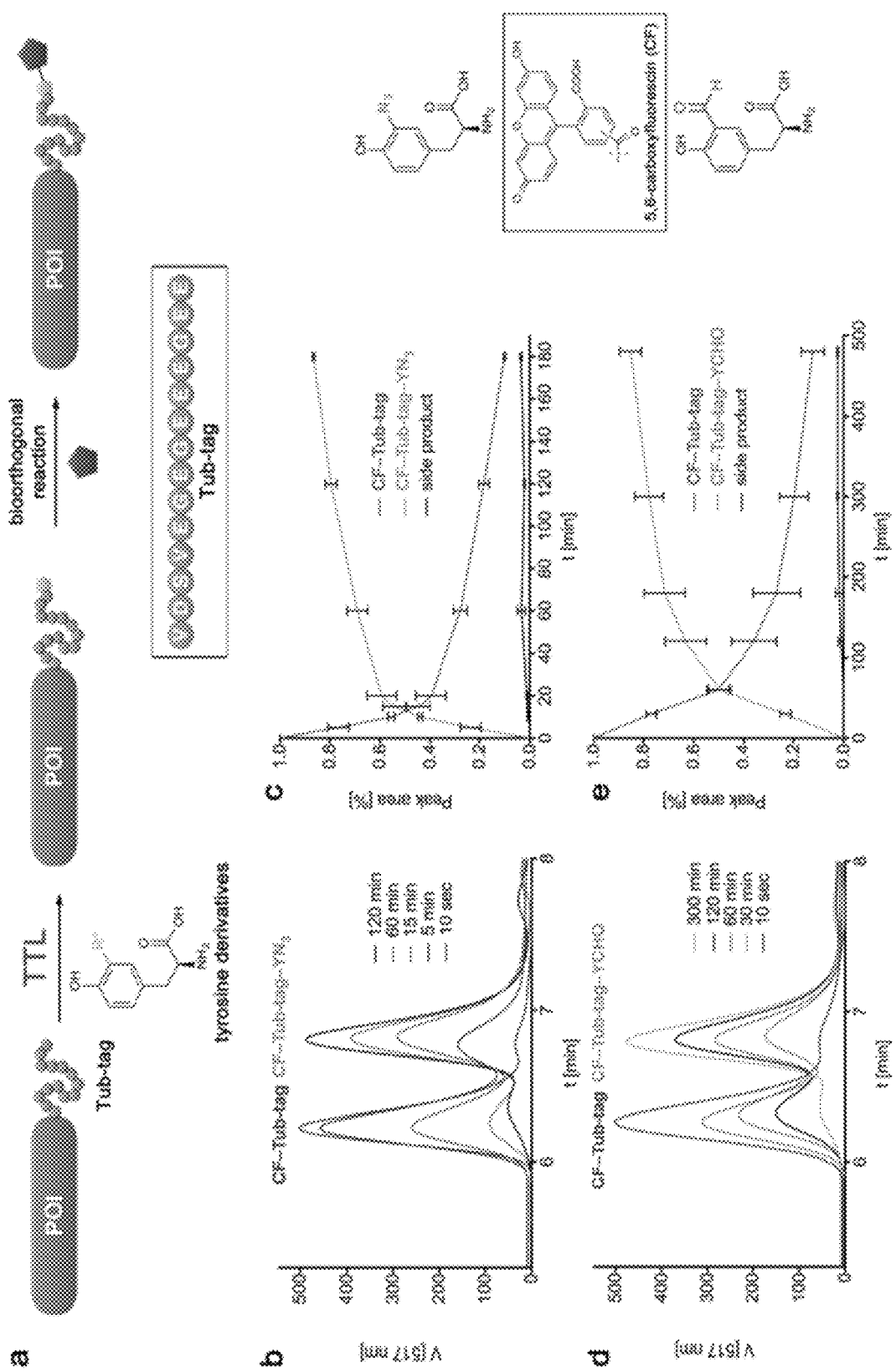
FIG. 5: Tub-tag labeling of proteins. (A) Chemoenzymatic labeling of proteins by tubulin tyrosine ligase (TTL). Unnatural tyrosine derivatives are ligated to the C-terminus of a short recognition tag (Tub-tag) to serve as bioorthogonal handles for a site-specific chemical modification of a protein of interest (POI). (B) C-terminal addition of 3-$N_3$-L-tyrosine to carboxyfluorescein labeled peptide (CF-Tub-tag). HPLC-fluorescence traces were taken at different time points of the TTL reaction. (C) The red line represents the consumption of CF-Tub-tag, the blue line the formation of C-terminally functionalized CF-Tub-tag-$YN_3$. The mean value and standard deviation (SD) of three replicate reactions is shown. Quantitation of substrate and product was performed via peak integration of b. (D) C-terminal addition of 3-formyl-L-tyrosine to CF-Tub-tag. HPLC-fluorescence traces were taken at different time points of the TTL reaction. (E) The red line represents the consumption of CF-Tub-tag, the green line the formation of C-terminally functionalized CF-Tub-tag-YCHO. The mean value and standard deviation (SD) of three replicate reactions is shown. Quantitation of substrate and product was performed via peak integration of d.

Here we present a novel and fast method for the site-specific labeling of proteins that combines the use of small unnatural amino acids as bioorthogonal handles and the technical advantages of chemoenzymatic labeling. The technique, termed Tub-tag labeling, is based on the enzymatic ligation of easy to synthesize, small tyrosine derivatives to the C-terminus of a fourteen amino acid hydrophilic recognition tag (termed Tub-tag) by tubulin tyrosine ligase (TTL, FIG. 5a). In nature, TTL catalyzes the post-translational attachment of tyrosine to the C-terminus of α-tubulin, which is involved in the regulation of microtubule homeostasis[11,12]. Interestingly, TTL also utilizes tyrosine derivatives for tubulin modification[13]. To test whether TTL may conjugate unnatural tyrosine derivatives to the isolated Tub-tag peptide, mimicking the C-terminus of tubulin, we performed an initial ligation experiment with 3-$N_3$-L-tyrosine (3) and 3-formyl-L-tyrosine (1). For this purpose, we first synthesized a 5,6-carboxyfluorescein labeled Tub-tag peptide (CF-Tub-tag) by standard solid phase peptide synthesis (SPPS), used it for Tub-tag labeling with 1 and 3 (TTL:peptide 1:200) and analyzed the reaction process by isocratic HPLC (FIGS. 5b and c for 3, FIGS. 5d and e for 1). After 120 min of incubation at 37° C. the conjugate yield with 1 and 3 was 63% and 80%, respectively.

Figure 6:
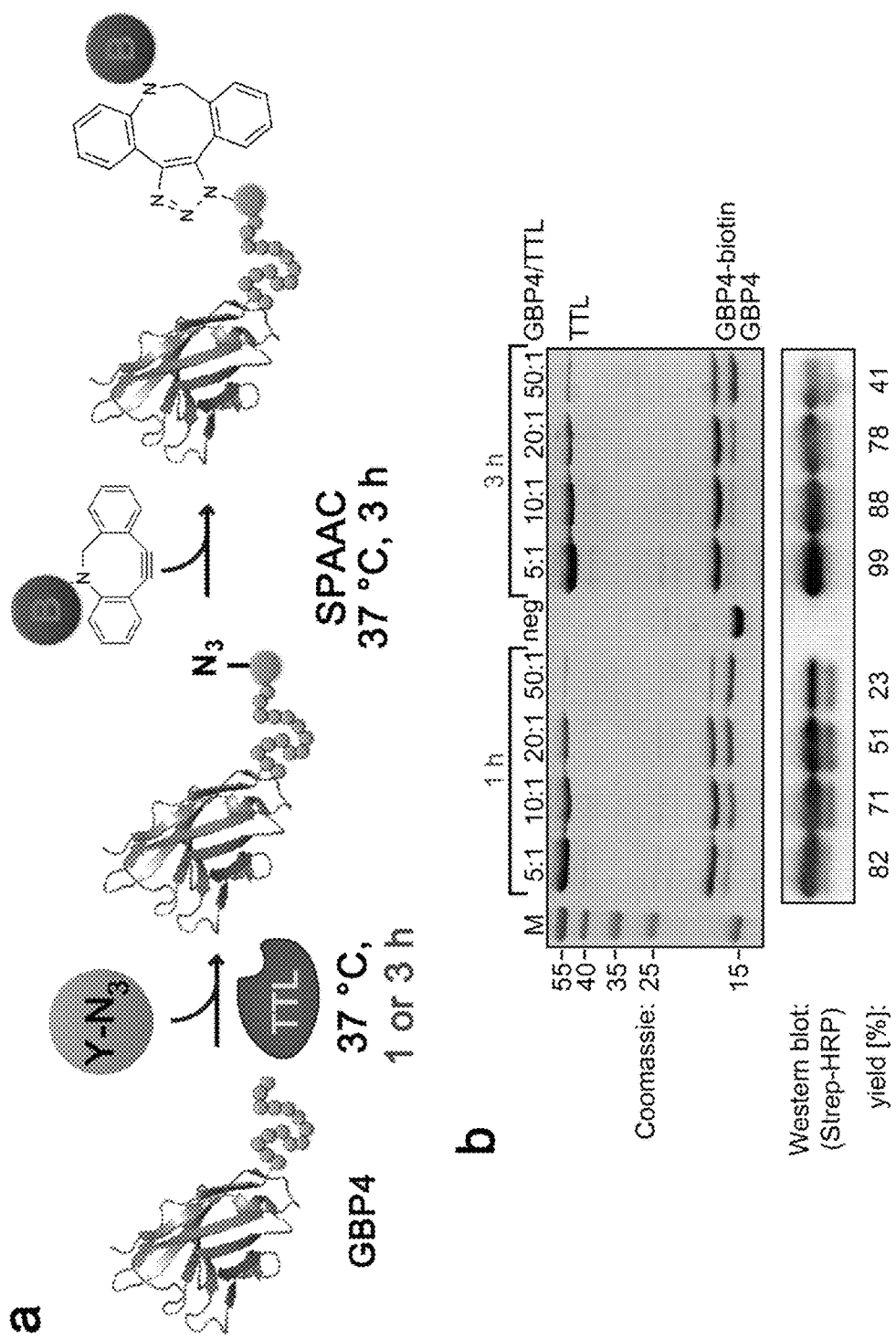
FIG. 6: Principle and efficiency of TTL-mediated functionalization (A) Schematic illustration of TTL mediated incorporation of azide 3 followed by subsequent strain promoted azide-alkyne cycloaddition (SPAAC). (B) Incorporation of azide 3 to the C-terminus of GBP4 using different ratios of GBP4/TTL and reaction times (one and three hours) followed by SPAAC to a DBCO-biotin derivative. SDS-PAGE and western blot (anti-Strep Ab-HRP) show efficient biotin labeling of GBP4 within one hour.
Figure 7:
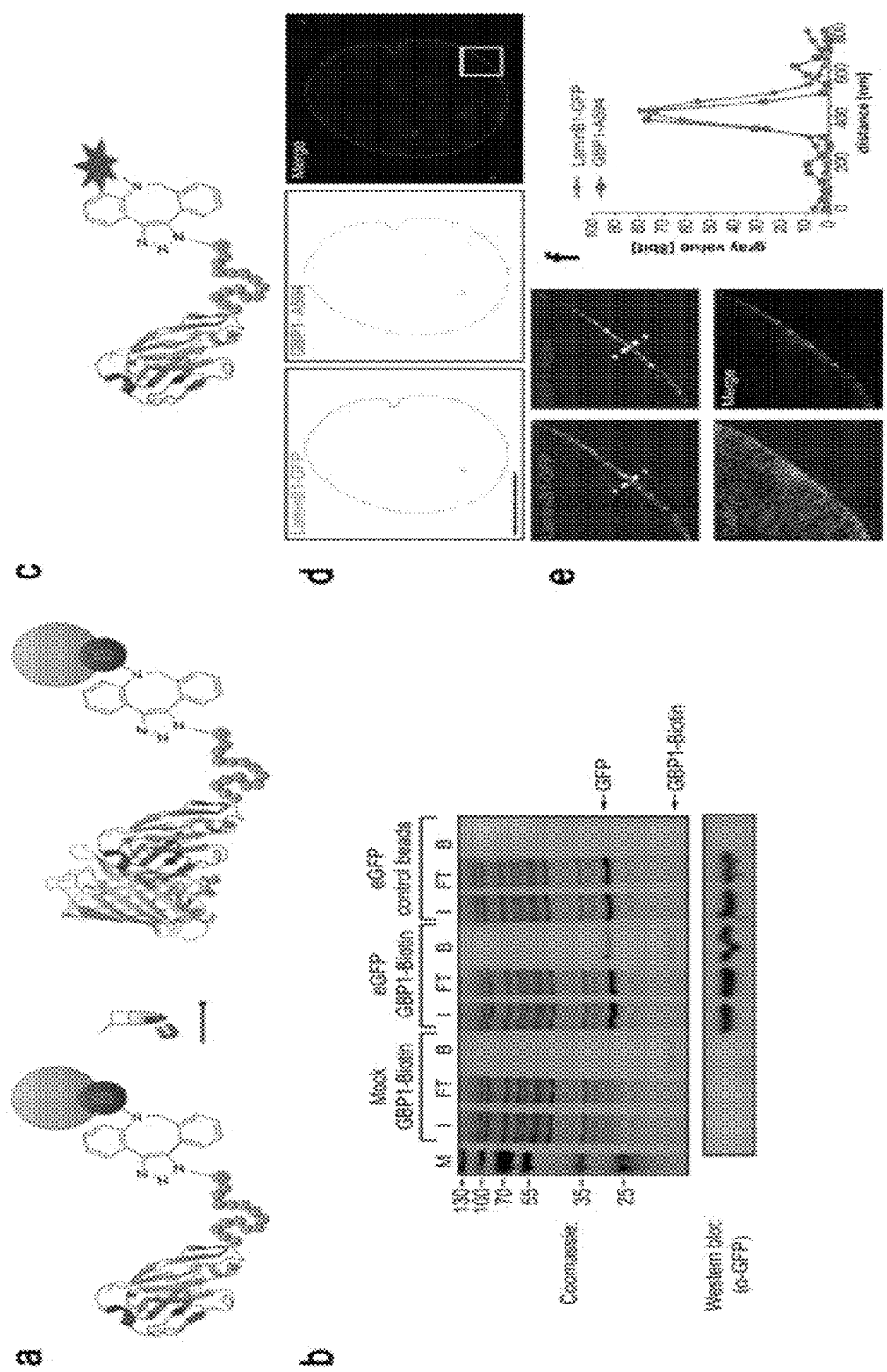
FIG. 7: Application of chemoenzymatically functionalized nanobodies (A) Schematic outline of immunoprecipitation of GFP with site-specifically biotinylated GBP1. (B) Coomassie staining and western blot analysis showing efficient and specific GFP pulldown. (C) Schematic outline of the site-specifically labeled GBP1-Alexa594 (D) Immunofluorescence with GBP1-Alexa594. Shown is a HeLa cell nucleus with the lamina co-labeled with LaminB1-GFP and GBP1-Alexa594. Scale bar is 10 μm. (E) zoom region of d. (F) A fluorescence intensity profile along the dotted line (shown in e) demonstrates high colocalization accuracy at subdiffraction resolution.
Figure 8:
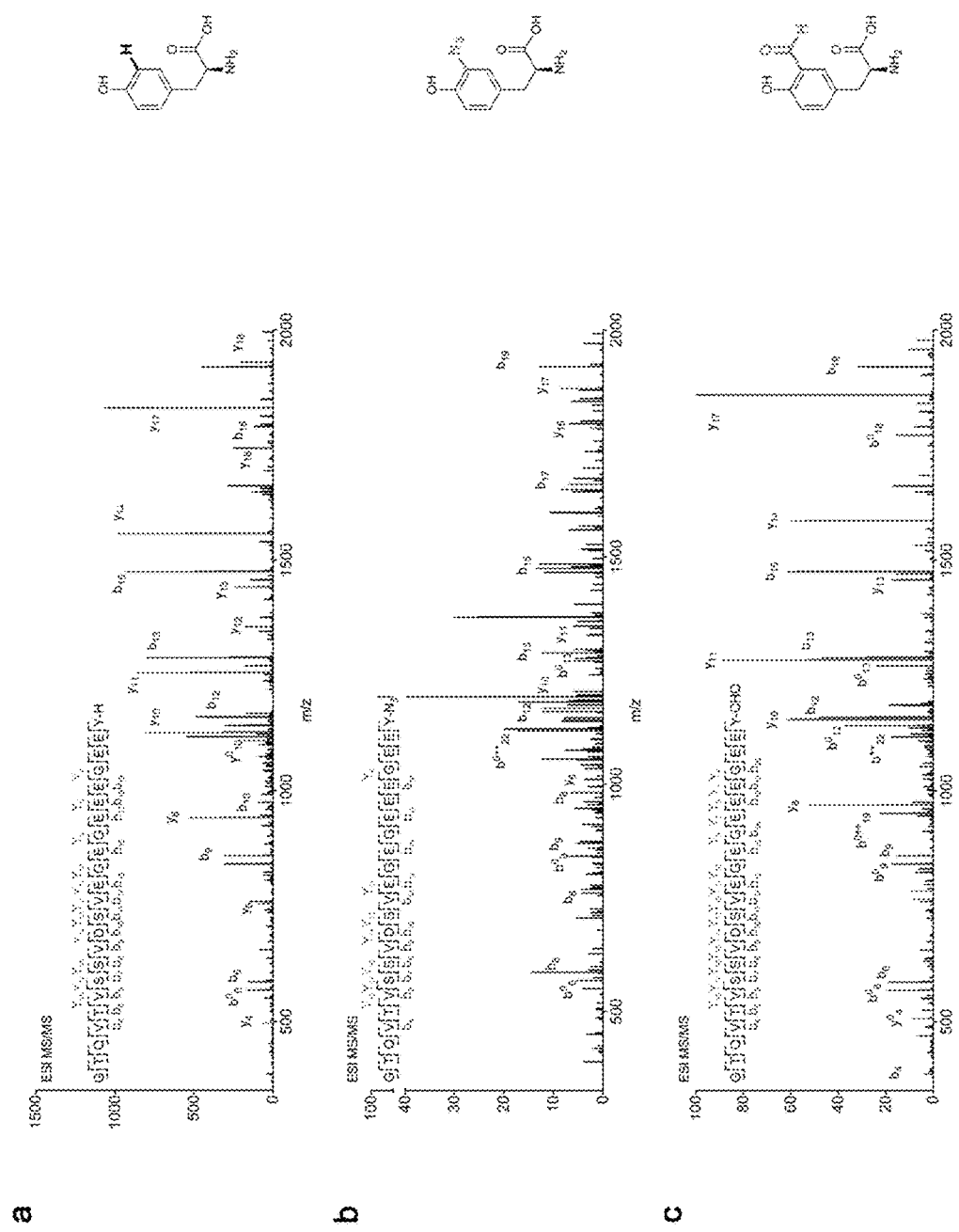
FIG. 8: Different tyrosine derivatives have been added to the C-terminus of the nanobody GBP4 using Tub-tag labeling. Tryptic digest followed by HPLC-MS/MS experiments revealed successful incorporation of (A) L-tyrosine, (B) 3-$N_3$-L-tyrosine, (C) 3-formyl-L-tyrosine, (D) 3-$NH_2$-L-tyrosine and (E) 3-$NO_2$-L-tyrosine.
Figure 8:
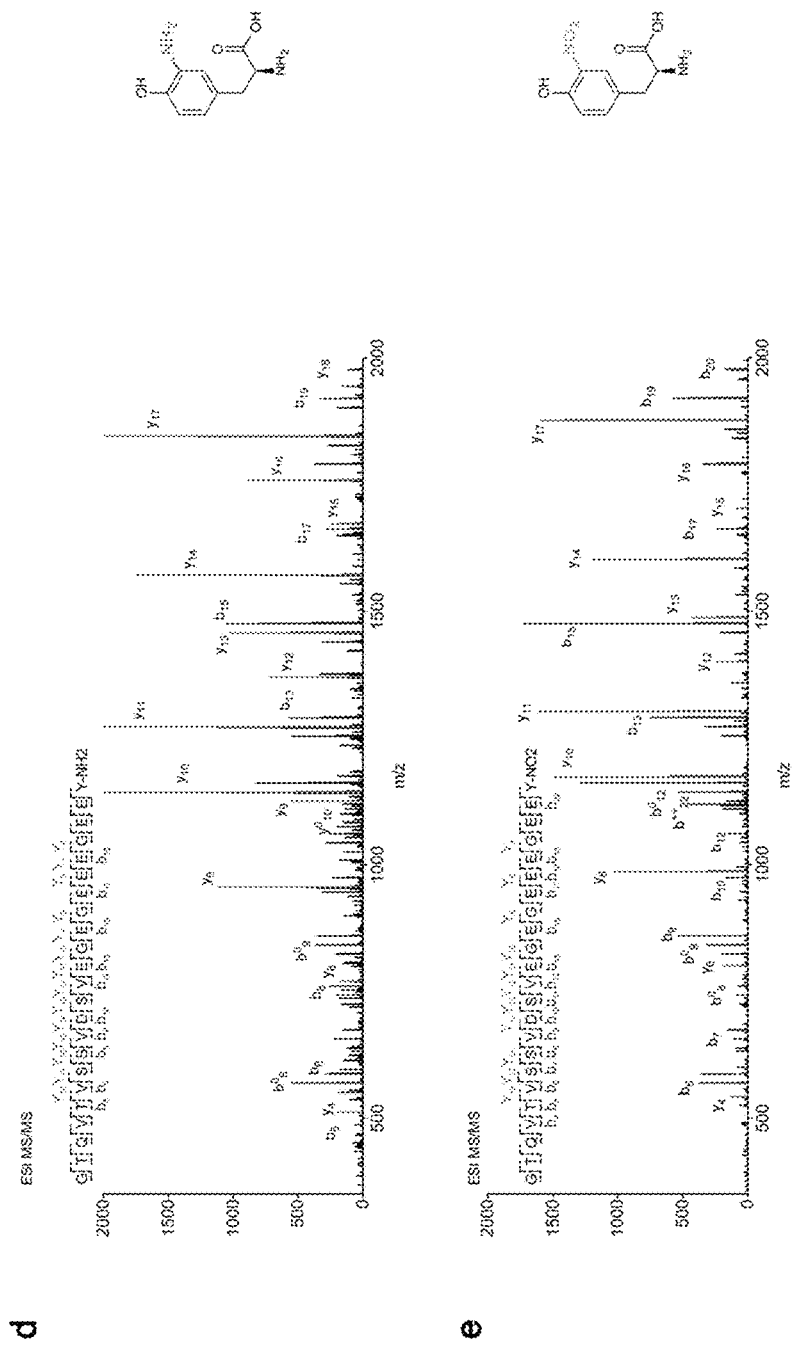
Figure 9:
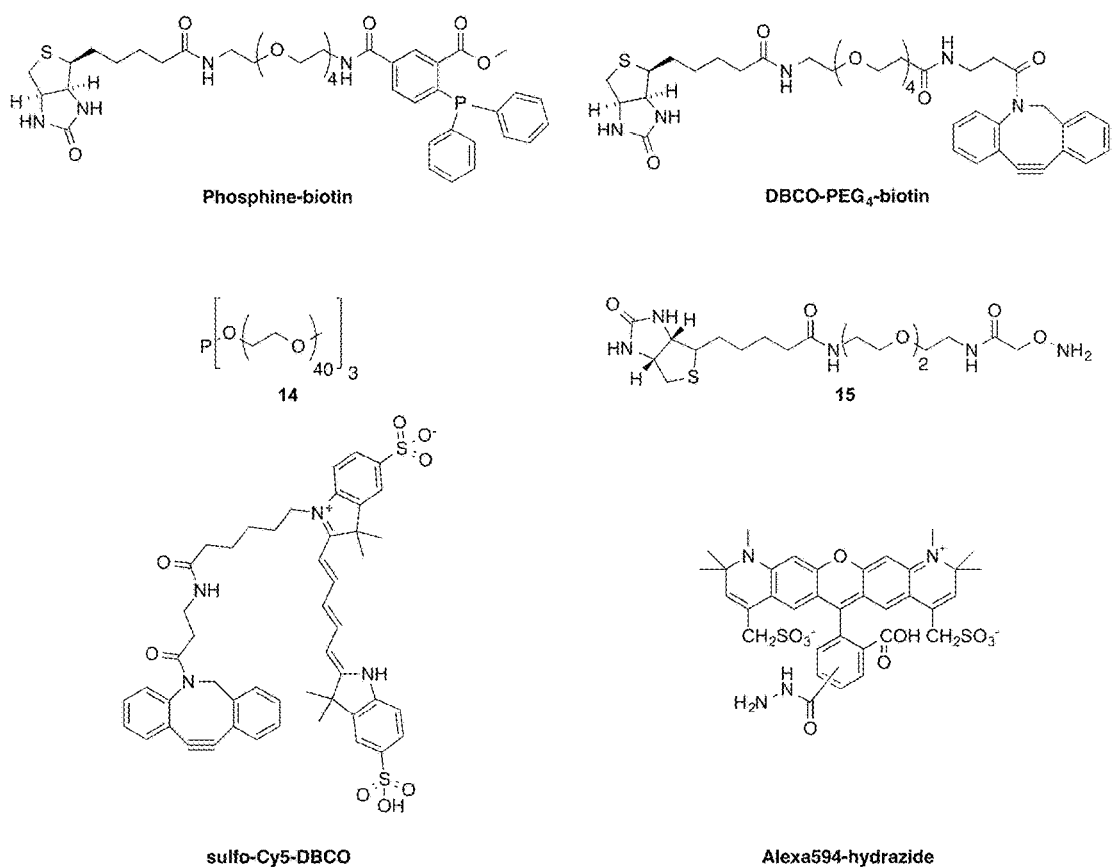
FIG. 9: Molecules used for bioorthogonal addition to C-terminal modified nanobodies.
Figure 10:
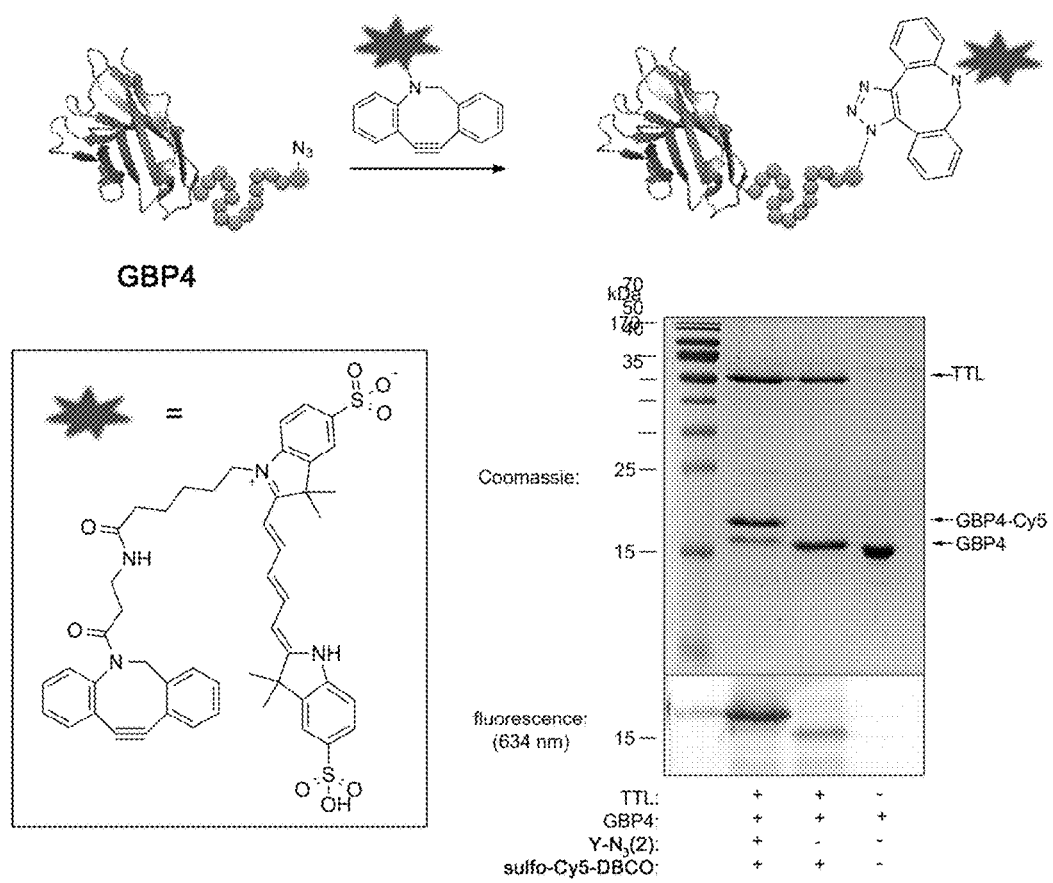
FIG. 10: Shown is the fluorescent labeling of GBP4 with sulfo-Cy5-DBCO. 3-$N_3$-L-tyrosine was enzymatically incorporated to the C-terminus of GBP4 using TTL. A following incubation with 30 eq. sulfo-Cy5-DBCO shows selective labeling of 3-$N_3$-L-tyrosine containing nanobody by strain promoted azide-alkyne click reaction (SPAAC).
Figure 11:
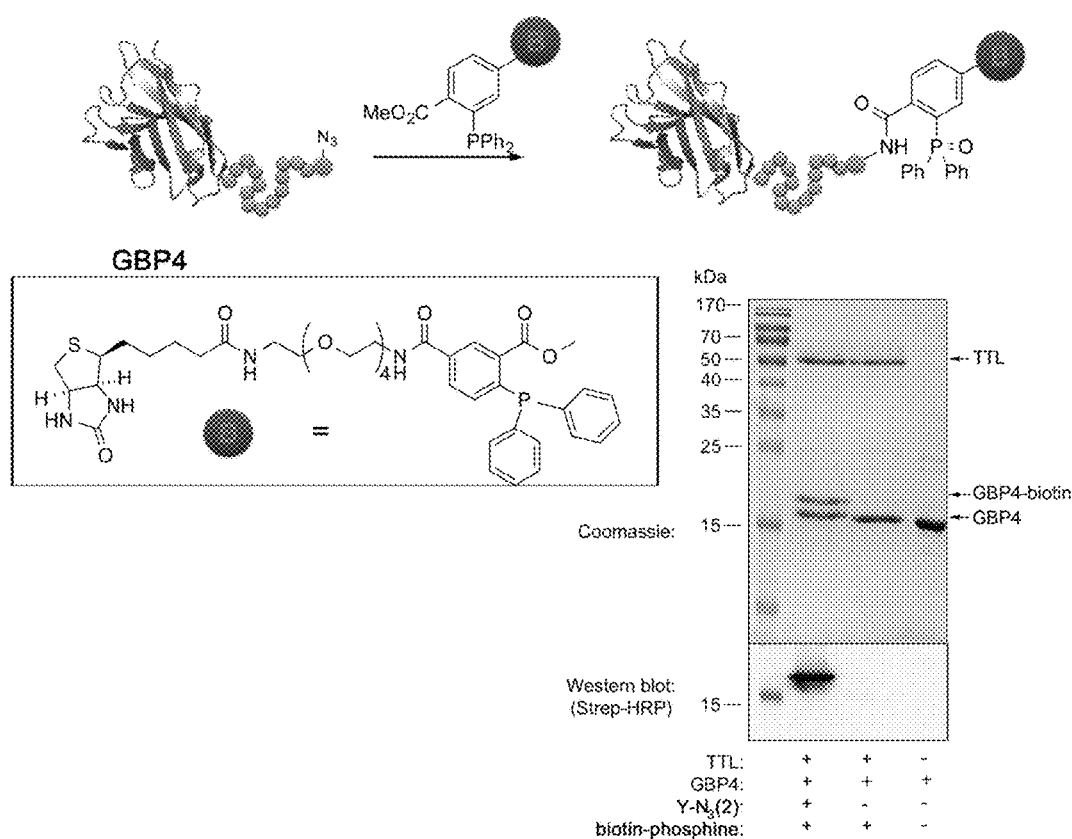
FIG. 11: Shown is the labeling of GBP4 with biotin-phosphine using Staudinger-Ligation. 3-$N_3$-L-tyrosine was enzymatically incorporated to the C-terminus of GBP4 using TTL. A following incubation with 40 eq. Biotin-phosphine shows selective labeling of 3-$N_3$-L-tyrosine containing nanobody by Staudinger-Ligation.
Figure 12:
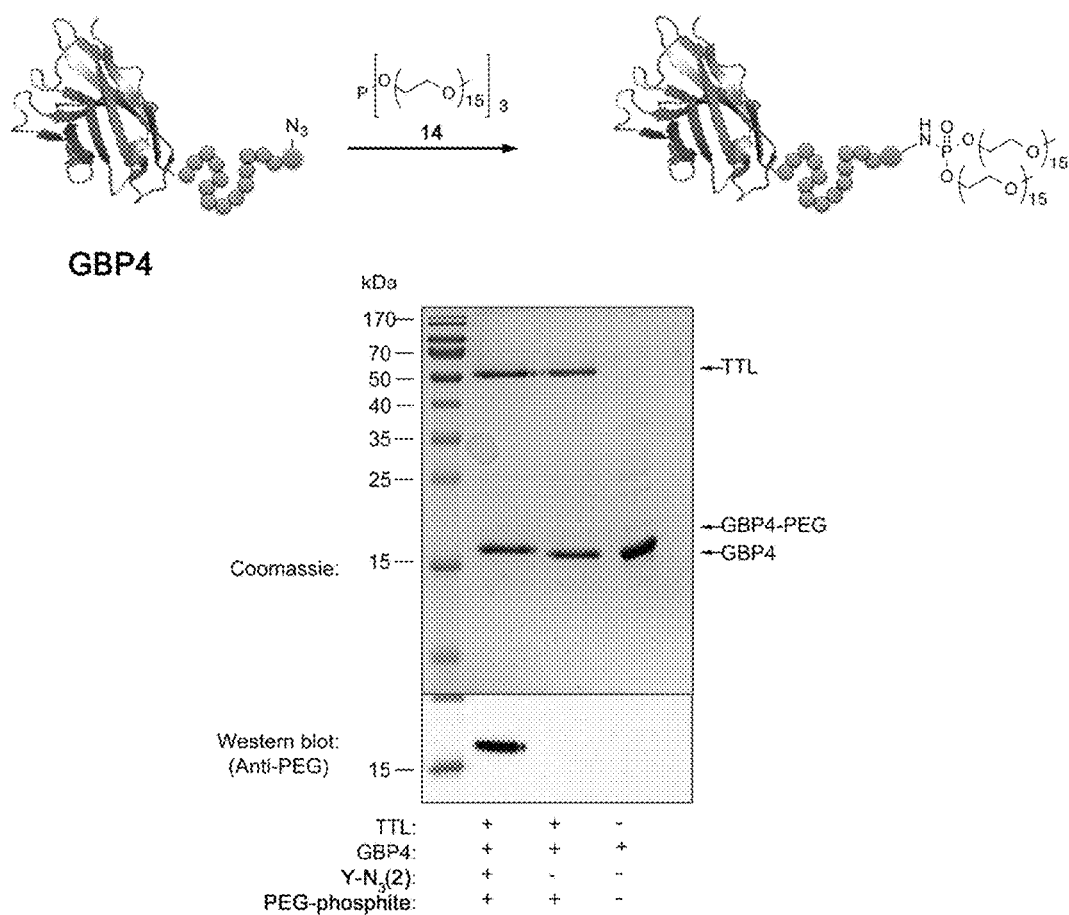
FIG. 12: Shown is the PEGylation of GBP4 with tris (PEG750)phosphite (14) by Staudinger-Phosphite reaction. 3-$N_3$-L-tyrosine was enzymatically incorporated to the C-terminus of GBP4 using TTL. A following incubation with 40 eq. phosphite shows selective labeling of 3-$N_3$-L-tyrosine containing nanobody by Staudinger Ligation.
Figure 13:
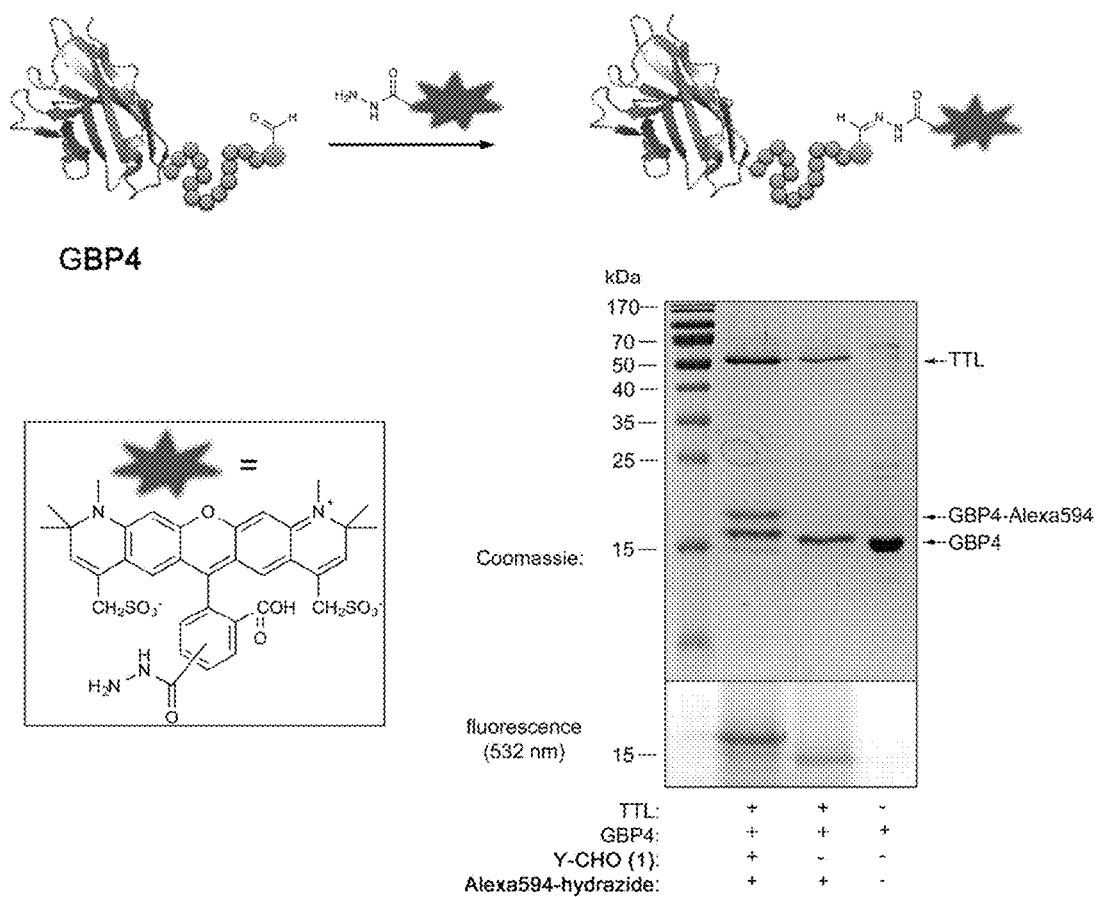
FIG. 13: Shown is the labeling of GBP4 with Alexa594-hydrazide using hydrazone forming reaction. 3-formyl-L-tyrosine was enzymatically incorporated to the C-terminus of GBP4 using TTL. A following incubation with 30 eq. Alexa594-hydrazide shows selective labeling of 3-formyl-L-tyrosine containing nanobody by aldehyde condensation.
Figure 14:
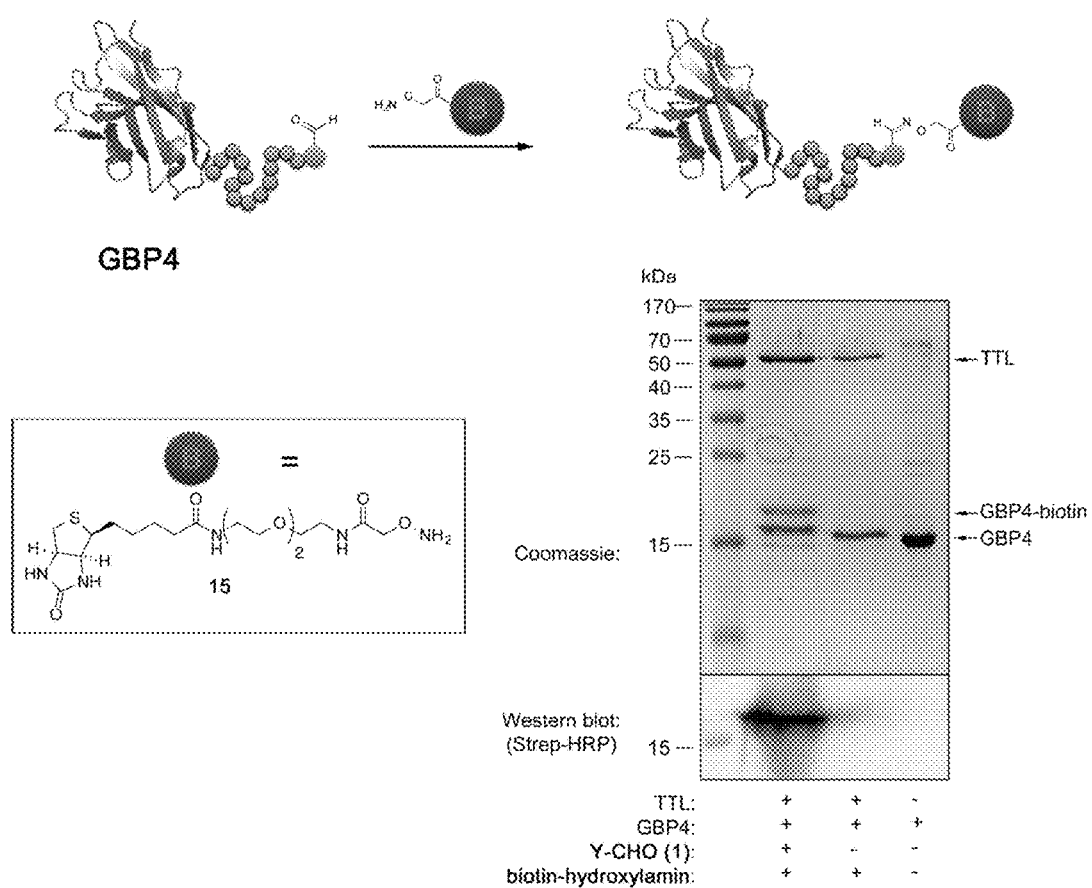
FIG. 14: Shown is the labeling of GBP4 with biotin 15 using oxime forming reaction. 3-formyl-L-tyrosine was enzymatically incorporated to the C-terminus of GBP4 using TTL. A following incubation with 30 eq. S2 shows selective labeling of 3-formyl-L-tyrosine containing nanobody by aldehyde condensation.
Figure 15:
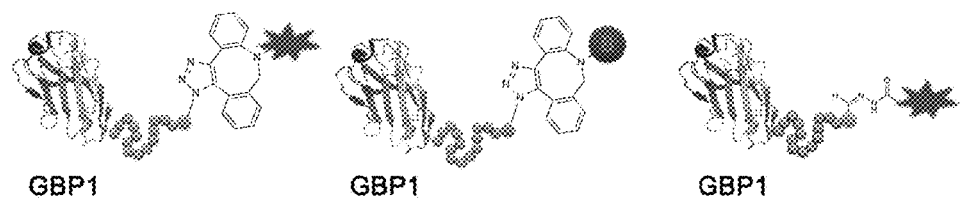
FIG. 15: Shown is the site-specific labeling of the GFP specific nanobody GBP1 using Tub-tag labeling. (A) 3-$N_3$-L-tyrosine was enzymatically incorporated to the C-terminus of GBP1 using TTL. A following incubation with 30 eq. sulfo-Cy5-DBCO or 30 eq. biotin-DBCO shows selective labeling of 3-$N_3$-L-tyrosine containing nanobody by strain promoted azide-alkyne click reaction (SPAAC). (B) 3-formyl-L-tyrosine was enzymatically incorporated to the C-terminus of GBP4 using TTL. A following incubation with 30 eq. Alexa594-hydrazide shows selective labeling of 3-formyl-L-tyrosine containing nanobody by aldehyde condensation.
Figure 15:
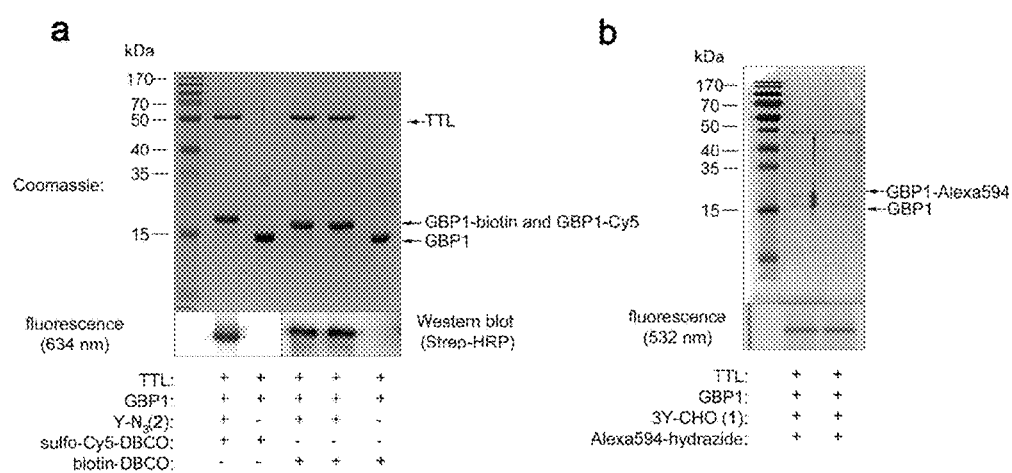

Next, we tested whether the Tub-tag labeling can be transferred to unrelated proteins of interest. For proof-of-principle we used camel-derived, single-domain nanobodies[14] that are used as analytical tools in biochemistry as well as for the intracellular recognition and manipulation of antigens in cell biology[15,16]. We fused the Tub-tag sequence to the C-terminus of a GFP-specific nanobody (GBP4[17]) and performed TTL-mediated labeling experiments. Tryptic digest followed by HPLC-MS/MS experiments showed the successful C-terminal addition of tyrosine (6), 3-$N_3$-L-tyrosine (3), 3-formyl-L-tyrosine (1), 3-$NH_2$-L-tyrosine (9) and 3-NO2-L-tyrosine (2) (FIG. 8). Next, we combined the incorporation of 3 with subsequent strain-promoted azide-alkyne cycloaddition (SPAAC)[18] for the conjugation of a DBCO-biotin derivative (FIG. 6). Using a ratio of 1:5 TTL/GBP4 at 37° C. we found that 82% of GBP4 was converted after one hour, whereas a ratio of 1:10 TTL/GBP4 delivered 71% C-terminally modified GBP4. Extending the ligation time to three hours resulted in 99% and 88% conversions at 1:5 and 1:10 TTL/GBP4 ratios, respectively. The incorporation of 3-formyl-L-tyrosine (1) could be achieved with similar efficiencies. To further validate the modularity of the Tub-tag labeling concept, we performed fluorescent labeling by SPAAC (FIG. 10) and employed a variety of well-established bioorthogonal reactions including the Staudinger-ligation[19] (FIG. 11) and the Staudinger-Phosphite reaction[20] (FIG. 12) to 3-N3-L-tyrosine (3). In addition, hydrazone (FIG. 13) and oxime forming reactions[21] (FIG. 14) were applied on site-specifically incorporated 3-formyl-L-tyrosine (1). This allowed us to incorporate different biotin derivatives, fluorophores and even enabled the branched PEGylation of GBP4 (FIG. 12). After having established this chemoenzymatic modification, we used this method for the fluorescent and biotin labeling of another GFP-specific nanobody (GBP1[17]) (FIG. 15). To test whether TTL-mediated modification yields functional nanobodies, we used GBP1 for biochemical and cell biological applications. Following 3-N3-L-tyrosine (3) incorporation via TTL, GBP1 was biotinylated using DBCO-biotin as described above and immobilized on Streptavidin-coated magnetic beads (Figure. 7a). These beads were then used for immunoprecipitation of GFP from HEK cell lysates. Subsequent western blot analysis demonstrated specific GFP pulldown compared to controls with mock transfected cell lysate and non-functionalized beads (Figure. 7b).

Figure 16:
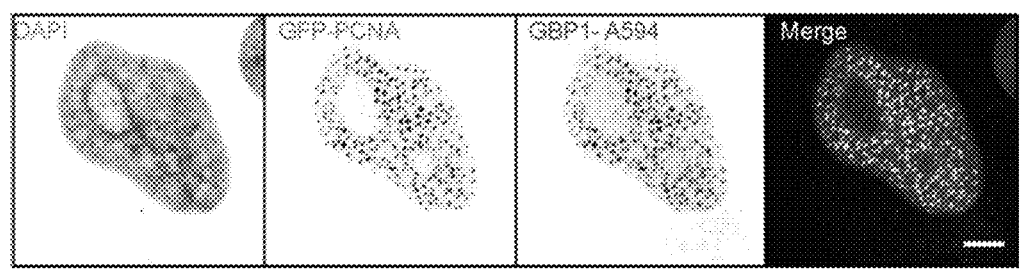
FIG. 16: Confocal micrographs of HeLa cells transfected with GFP-PCNA fusions. Cells were labeled with anti-GFP (GBP1) conjugated to the fluorescent dye Alexa594 at 1:25. The DAPI, GFP and Alexa594 channels, as well as the overlay are shown. Scale bar: 5 μm.
Figure 17:
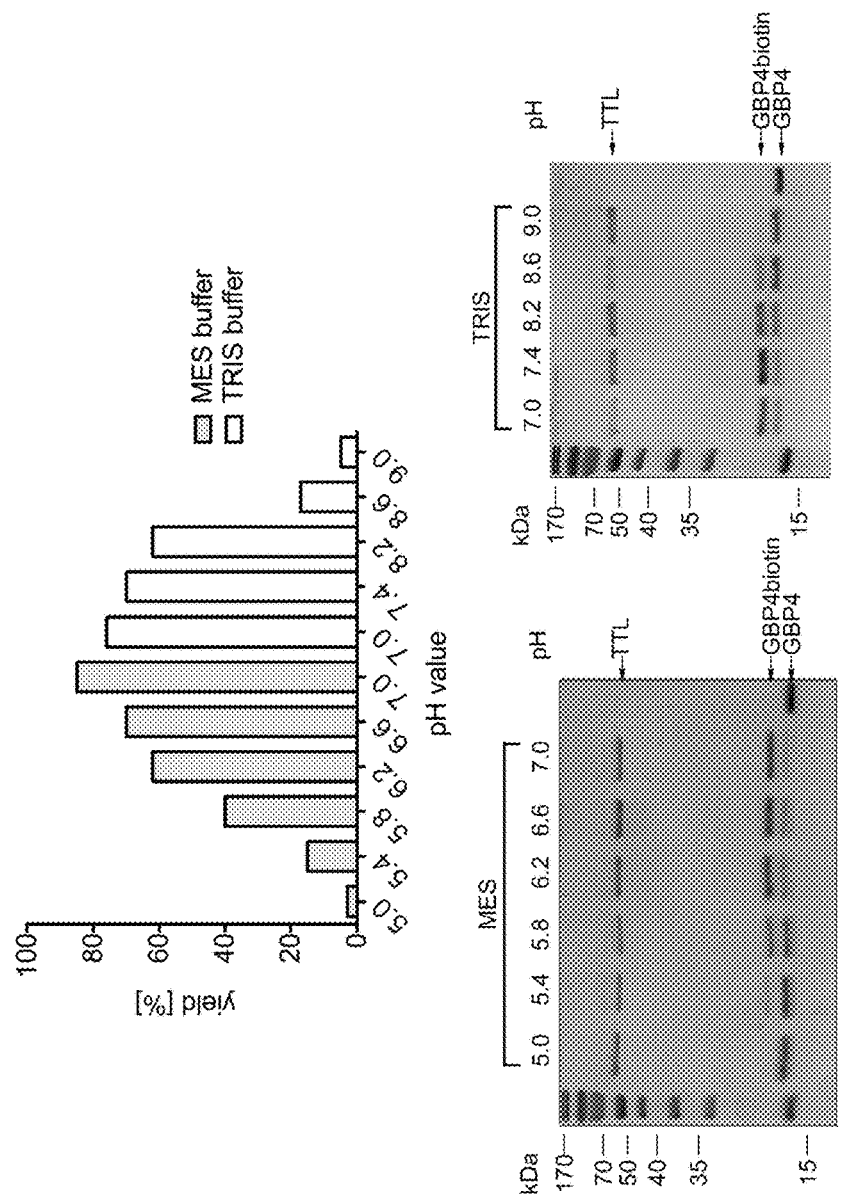
FIG. 17: 3-$N_3$-L-tyrosine incorporation to the C-terminus of GBP4 in relation to pH value is shown. Reactions were performed using a 10:1 ratio GBP4:TTL at different pH values (5.0-9.0) for 3 h. Reactions were quickly cooled to 4° C., excess of 3-$N_3$-L-tyrosine removed via dialysis (at 4° C.) and SPAAC to DBCO-biotin performed. The yields were estimated using the software Image Lab (Bio-Rad, USA).
Figure 18:
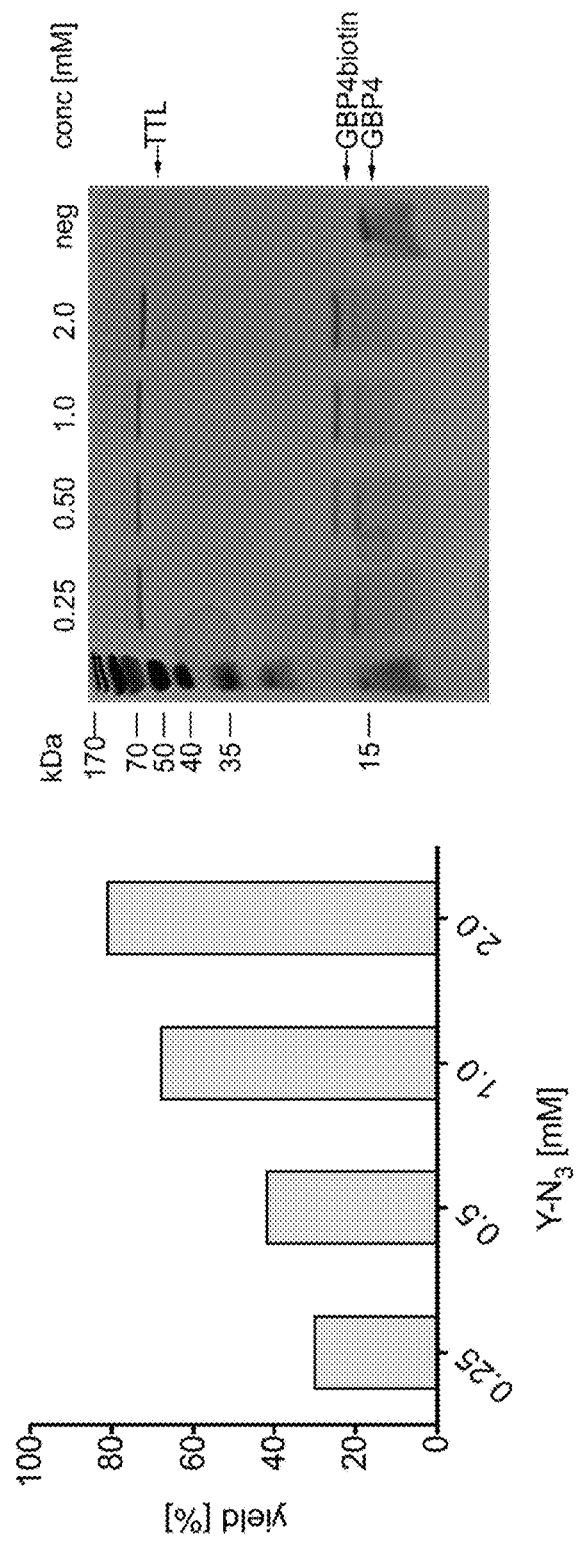
FIG. 18: 3-$N_3$-L-tyrosine incorporation to the C-terminus of GBP4 in relation to 3-$N_3$-L-tyrosine concentration is shown. Reactions were performed using a 10:1 ratio GBP4:TTL at using different tyrosine derivative concentration (0.25-2 mM) for 1 h. Reactions were quickly cooled to 4° C., excess of 3-$N_3$-L-tyrosine removed via dialysis (at 4° C.) and SPAAC to DBCO-biotin performed. The yields were estimated using the software Image Lab (Bio-Rad, USA).
Figure 19:
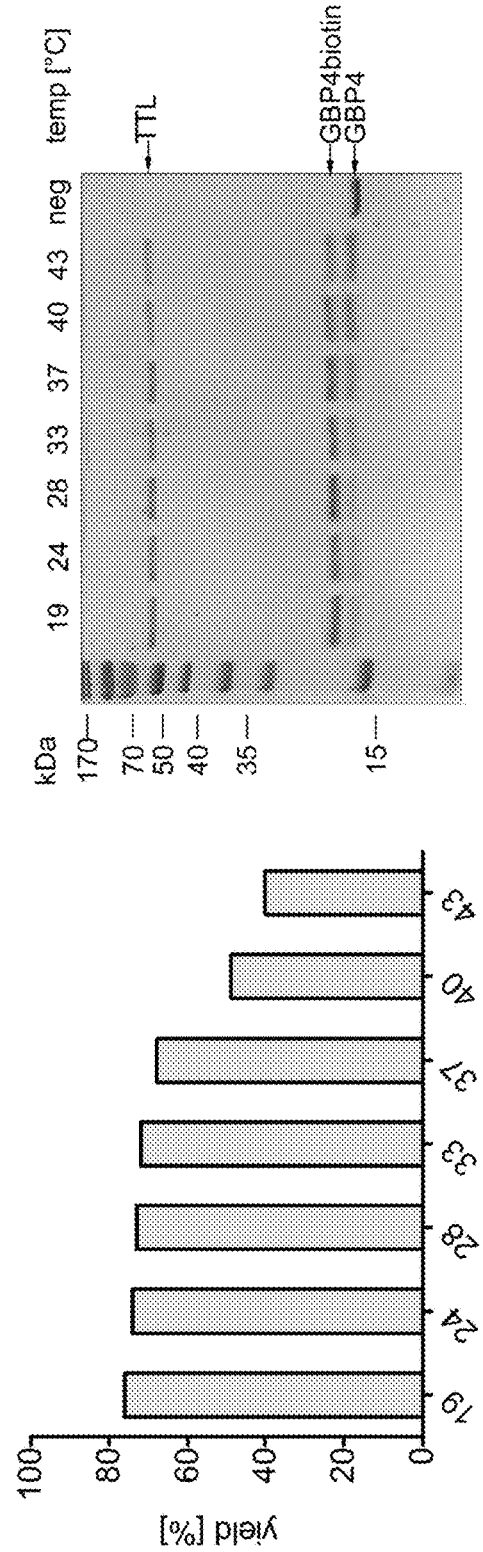
FIG. 19: 3-$N_3$-L-tyrosine incorporation to the C-terminus of GBP4 in relation to reaction temperature is shown. Reactions were performed using a 10:1 ratio GBP4:TTL at different temperatures for 1 h. Reactions were quickly cooled to 4° C., excess of 3-$N_3$-L-tyrosine removed via dialysis (at 4° C.) and SPAAC to DBCO-biotin performed. The yields were estimated using the software Image Lab (Bio-Rad, USA).
Figure 20:
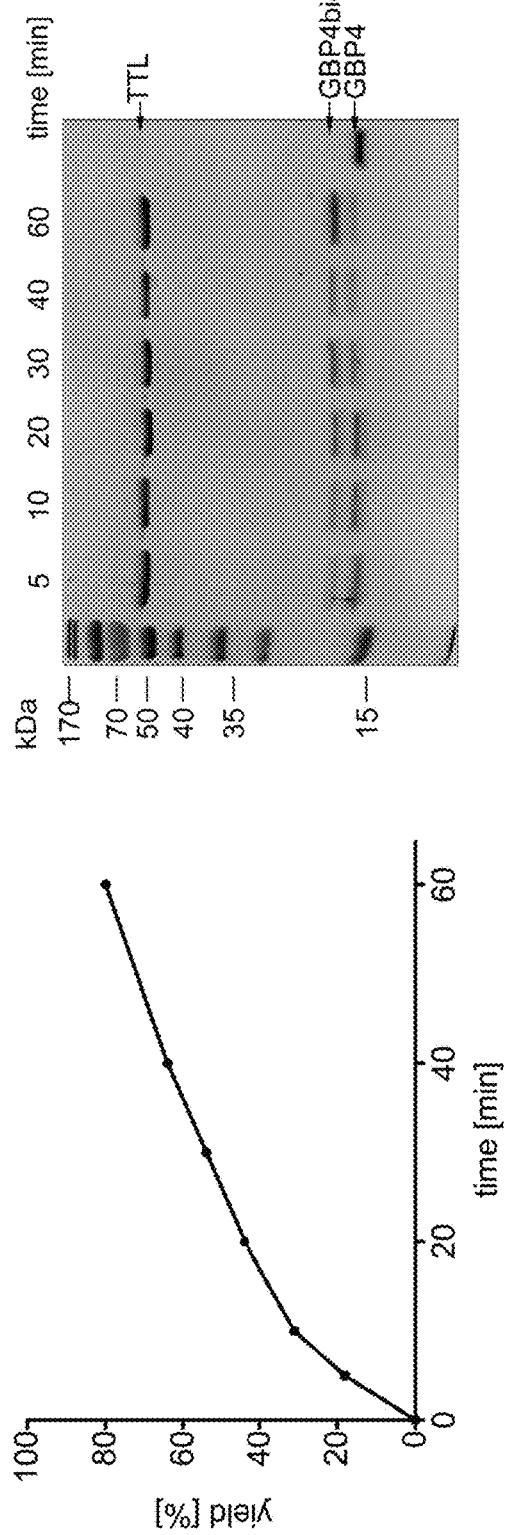
FIG. 20: The time correlation of 3-$N_3$-L-tyrosine incorporation to the C-terminus of GBP4 is shown. Reactions were performed using a 5:1 ratio GBP4:TTL at 37° C. Reactions were quickly cooled to 4° C. at specific timepoints, excess of 3-$N_3$-L-tyrosine removed via dialysis (at 4° C.) and SPAAC to DBCO-biotin performed. The yields were estimated using the software Image Lab (Bio-Rad, USA).
Figure 21:
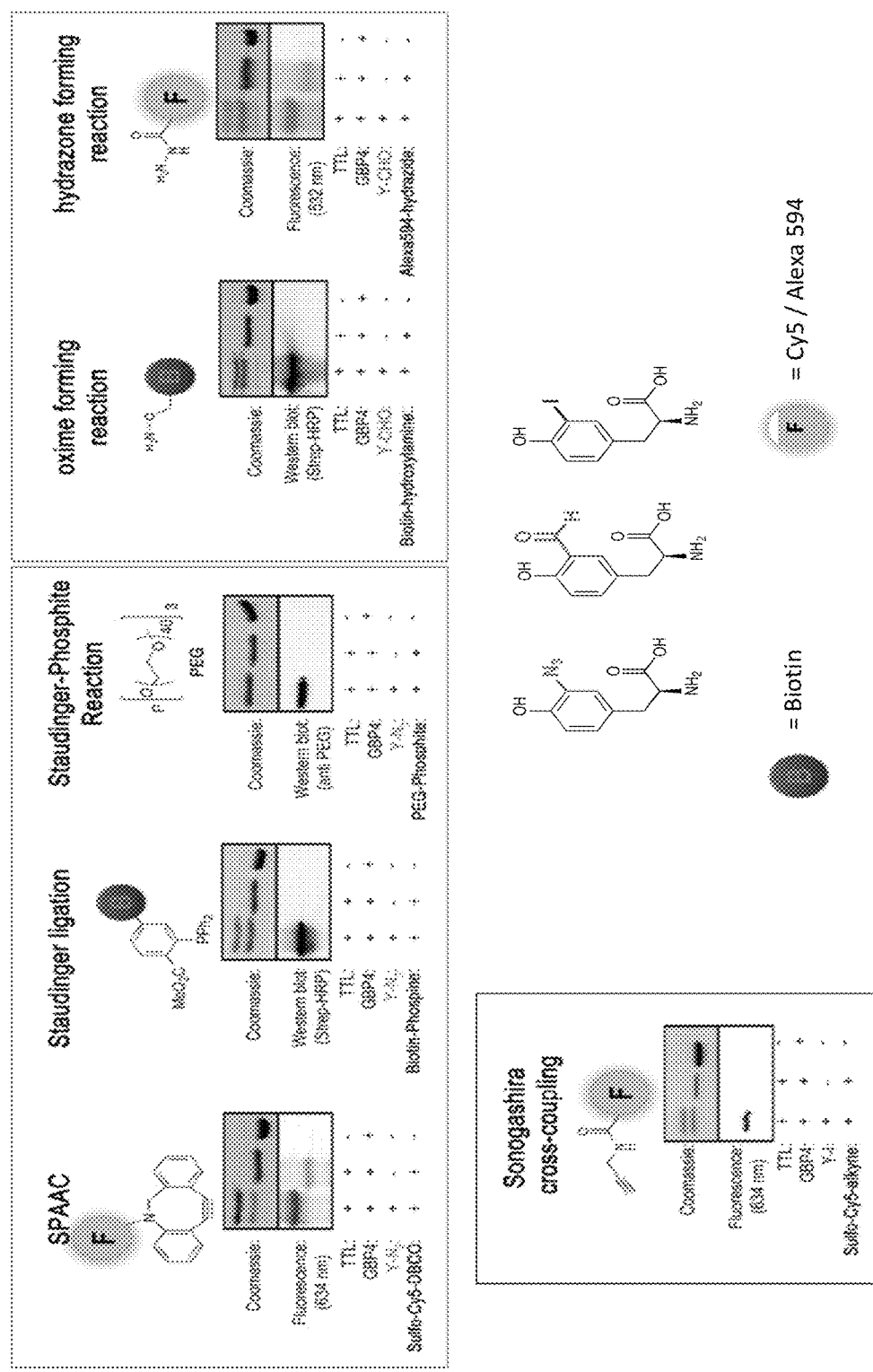
FIG. 21: Coupling reactions

We subsequently studied, whether site-specifically labeled GBP1 can be used to stain cellular structures in immunofluorescence experiments. We have previously used this GFP-binding nanobody as a staining reagent for super-resolution microscopy techniques[22]. The higher resolution imposes new requirements on detection reagents and, thus, using the smallest possible immunofluorescent binding reagents is important to unleash the full potential of super-resolution microscopy[23]. Here, following 3-formyl-L-tyrosine (1) incorporation via TTL, GBP1 was labeled with Alexa594 dye using oxime forming reaction (FIG. 7c). HeLa cells expressing GFP-LaminB1, which localizes at the interior of the nuclear envelope and forms the nuclear lamina, were stained with GBP1-Alexa594. 3D-SIM super-resolution microscopy then revealed laminar colocalization of the GBP1 staining reagent at high resolution, indicating functional binding to GFP in this cellular context (FIGS. 7d, e and f). Similar results were obtained with GFP-PCNA and the detection of subnuclear DNA replication sites (FIG. 16).

In summary, we introduce Tub-tag labeling for simple, site-specific modification of proteins. We show TTL-mediated, chemoenzymatic ligation of unnatural tyrosine derivatives like 3-$N_3$-L-tyrosine (3) and 3-formyl-L-tyrosine (1) with up to 99% efficiency using moderate enzyme concentrations and short reaction times. These modified tyrosine residues then serve as bioorthogonal handles for a variety of well-established chemoselective labeling reactions. The overall labeling efficiency under mild reaction conditions yields homogeneously modified and functional proteins as demonstrated with nanobodies for immunoprecipitation and super-resolution microscopy. Thus, Tub-tag labeling endows recombinant antibodies—and proteins in general—with novel properties to explore and manipulate cellular functions with possible applications in biotechnology as well as in diagnosis and therapy.

Example 12: TTL Expression and Purification

TTL (*Canis lupus*) coding sequence was amplified from a mammalian expression vector24, cloned into a pET28-SUMO3 (EMBL-Heidelberg, Protein Expression Facility) and expressed in *E. coli* BL21(DE3) as Sumo-TTL fusion protein with an N-terminal His-Tag. Cells were induced with 0.5 mM IPTG and incubated at 18° C. for 18 h. Lysis was performed in presence of Lysozyme (100 μg/ml), DNAse (25 μg/ml) and PMSF (2 mM) followed by sonification (Branson® Sonifier; 16×8 sec, 20% amplitude) and debris centrifugation at 20.000 g for 30 min. His-Sumo-TTL was purified using a 5 ml His-Trap. Purified protein was then desalted on a PD10 column (GE Healthcare); buffer was exchanged to MES/K pH 6.8 (20 mM MES, 100 mM KCl, 10 mM MgCl2). Protein aliquots were shock-frozen and stored at −80° C. at 2.7 g/l.

Example 13: Determination of TTL Activity Using CF-Tub-Tact Peptide 13

Tyrosination reactions were performed in a 250 μL solution consisting of 20 mM MES/K pH 7.0, 100 mM KCl, 10 mM MgCl2, 2.5 mM ATP, 1 mM tyrosine derivative, 0.2 mM CF-Tub-tag 13, 1 μM TTL and 5 mM DTT in case of compound 2 or 5 mM reduced glutathione in case of compound 1, respectively. The mixture was incubated at 37° C. and several aliquots (25 μL) were taken, mixed with equal volumes of H₂O+0.1% TFA and subjected to isocratic analytical HPLC equipped with a fluorescence detector (Method: A=H2O+0.1% TFA, B=MeCN+0.1% TFA; 35% B, 0-15 min, 10-100% B 15-17 min, 100% B 17-22 min, 100-35% B 22-25 min and 35% B 25-30 min.). Quantities of substrate and product peptides were estimated from the corresponding peak-area in the fluorescence detection spectrum (Ex/Em: 495/517).

Example 14: Nanobody-Tub-Tag Expression and Purification

Nanobody-Tub-tag fusion proteins were expressed in *E. coli* (JM109). Cells were induced with 0.5 mM IPTG and incubated at 18° C. for 18 h. Lysis was performed in presence of Lysozyme (100 μg/ml), DNAse (25 μg/ml) and PMSF (2 mM) followed by sonication (Branson® Sonifier; 16×8 sec, 20% Amplitude) and debris centrifugation at 20.000 g for 30 min. The protein was purified with an Äkta FPLC system using a 5 mL His-Trap (GE Healthcare, USA) column, peak fractions were concentrated to 2 ml using Amicon filter columns (cut-off 3 kDa; (Merck Millipore, Germany) and subjected to size exclusion chromatography using a Superdex 75 column (GE Healthcare, USA). Peak fractions were pooled and protein aliquots were shock-frozen and stored at −80° C.

Example 15: TTL Reaction on GBP4 Followed by Tryptic Digest and MSMS Analysis Tyrosination reactions were performed in a 50 μL solution consisting of 20 mM MES/K pH 7.0, 100 mM KCl, 10 mM MgCl₂, 2.5 mM ATP, 1 mM tyrosine derivative, 1 μM TTL, 5 μM nanobody and 5 mM reduced glutathione in case of compound 3 and 5 mM DTT in case of compound 1, 2, 9 and tyrosine (6), respectively. The mixture was incubated at 37° C. for 24 h. Proteins were separated by SDS-PAGE. Protein bands of interest were excised, soaked with 100 μL 50 mM (NH₄)₂CO₃/ACN 1:1 and incubated at 30° C. for 10 min. The supernatant was removed and the gel pieces were incubated in 50 mM (NH₄)₂CO₃ at 30° C. for further 10 min. The two incubation steps were repeated until the pieces were colourless. Hereafter, the gel pieces were dehydrated by the addition of 25 μL ACN, the supernatant removed and the gels were dried under reduced pressure. In-gel digest was performed in a total volume of 20 μL 50 mM (NH₄)₂CO₃ at 37° C. for 12 h using 0.05 μg trypsin (Thermo Fisher Scientific, USA). 20 μL ACN+0.5% TFA was added, the mixture incubated in an ultrasonic bath, the supernatant transferred to LC glass vials, the solvent removed under reduced pressure and the residual peptides resuspended in 6 μL 95% H₂O+0.1% TFA, 5% ACN+0.1% TFA solution. Peptides were separated by HPLC and analyzed by MSMS experiments.

Example 16: Chemoenzymatic Addition of Tyrosine Derivatives to Nanobodies

Tyrosination reactions were performed in a 150 μL solution consisting of 20 mM MES/K pH 7.0, 100 mM KCl, 10 mM MgCl₂, 2.5 mM ATP, 1 mM tyrosine derivative, 0.1-1 μM TTL, 5 μM nanobody and 5 mM reduced glutathione in case of compounds containing azides or 5 mM DTT for all other derivatives, respectively. The mixture was incubated at 37° C. for 1-3 h.

Example 17: SPAAC to Sulfo-Cy5-DBCO or Biotin-DBCO

Tyrosination reactions were performed as described in Example 16 using compound 3, 5 mM reduced glutathione and a ratio of 10:1 GBP4/TTL for 3 h. The reaction mixtures were rebuffered to Dulbecco's PBS pH 7.4 and incubated with 30 eq. of Sulfo-Cy5-DBCO (Jena Bioscience GmbH, Germany) or DBCO-PEG4-biotin (Jena Bioscience GmbH, Germany) at 30° C. for 4 h. Proteins were separated by SDS-PAGE. Biotinylated nanobodies were wet blotted onto a nitrocellulose membrane using a Bio-Rad Mini-Protean Tetra System (250 mA, one hour). A streptavidin peroxidase conjugate (Merck Millipore, Germany) was used for detection. Fluorescently labeled nanobodies were visualized by a Fuji FLA-5000 laser imager (634 nm excitation, LPG-filter) (Fujifilm, Japan).

Example 18: Staudinger-Ligation

Tyrosination reactions were performed as described in Example 16 using compound 3, 5 mM reduced glutathione and a ratio of 10:1 GBP4/TTL for 3 h. The reaction mixtures were rebuffered to Dulbecco's PBS pH 7.4 and incubated with 40 eq. of biotin-phosphine (BIOMOL GmbH, Germany) at 37° C. for 24 h. Proteins were separated by SDS-PAGE. Biotinylated nanobodies were wet blotted onto a nitrocellulose membrane using a Bio-Rad Mini-Protean Tetra System (250 mA, 1 h). A streptavidin peroxidase conjugate (Merck Millipore, Germany) was used for detection.

Example 19: Staudinger-Phosphite Reaction

Tyrosination reactions were performed as described in Example 16 using compound 3, 5 mM reduced glutathione and a ratio of 10:1 GBP4/TTL for 3 h. The reaction mixtures were rebuffered to 50 mM Tris pH 8.5, 100 mM KCl and incubated with 40 eq. of tris(PEG750)phosphite (14) at 37 C for 24 h. Proteins were separated by SDS-PAGE. PEGylated nanobodies were wet blotted onto a nitrocellulose membrane using a Bio-Rad Mini-Protean Tetra System (250 mA, 1h). A monoclonal anti PEG-B-47 antibody (Abcam, UK) and a secondary Goat Anti-Rabbit IgG H&L (HRP) (Abcam, UK) were used for detection.

Example 20: Hydrazone and Oxime Forming Reactions

Tyrosination reactions were performed as described in Example 16 with compound 1, 5 mM DTT and a ratio of 10:1 GBP4/TTL for 3 h. The reaction mixtures were rebuffered to 50 mM MES/K pH 6.0, 100 mM KCl and incubated with 30 eq of Alexa594-hydrazide (Thermo Fisher Scientific, USA) or hydroxylamine-biotin (15) at 37° C. for 4 h. Proteins were separated by SDS-PAGE. Biotinylated nanobodies were wet blotted onto a nitrocellulose membrane using a Bio-Rad Mini-Protean Tetra System (250 mA, 1 h). A streptavidin peroxidase conjugate (Merck Millipore, Germany) was used for detection. Fluorescently labeled nanobodies were visualized by a Fuji FLA-5000 laser imager (532 nm excitation, LPG-filter) (Fujifilm, Japan).

Example 21: Immunofluorescence

HeLa-Kyoto cells were maintained in DMEM supplemented with 10% fetal calf serum and gentamycin at 50

µg/ml (PAA, Germany). For immunofluorescence experiments $10^6$ cells were seeded on gridded 18×18 mm coverslips in a 6-well plate. Transfection with LaminB1-GFP encoding plasmid DNA (kind gift from Jan Ellenberg) was performed with Lipofectamine 3000 (Life Technologies, USA) according to the manufacturers' instructions. 18 h post transfection, cells were washed with PBST, fixed with 2% formaldehyde/PBS, and permeabilized with 0.5% Triton X-100/PBS. Next, cells were blocked with 2% BSA/PBST. Cells were then incubated with Atto594 Tub-tag labeled GBP1 for 1 h, washed with PBST, DAPI stained (Life Technologies, USA) and mounted in Vectashield anti-fading reagent (Vector Laboratories, USA) on object slides. High-resolution microscopy was performed with an DeltaVision OMX v3 (Applied Precision, Slovakia) equipped with 405, 488 and 593 nm laser diodes, a 100×/1.4 NA Plan-Apochromat oil objective lens (Olympus, Japan) and Cascade 11:512 EM CCD cameras (Photometrics, USA) as described previously (Guizetti, J. et al. Cortical constriction during abscission involves helices of ESCRT-III-dependent filaments. Science 331, 1616-1620, doi:science.1201847 [pii] 10.1126/science.1201847 (2011)). Line scan fluorescence intensity analysis was performed with ImageJ.

Example 22: Streptavidin Pulldown Assay

HEK 293T cells were maintained in DMEM supplemented with 10% fetal calf serum and gentamycin at 50 µg/ml (PM, Germany). For pulldown experiments 107 cells were seeded in p100 dishes. Transfection with eGFP encoding plasmid DNA peGFP-C1 (Life Technologies, Germany) was performed with polyethylenimine (PEI, Sigma, USA) with 24 µg DNA per dish. Pulldown reagent was prepared by using biotinylated GBP1 (Tub-tag mediated). For this purpose, 200 µl slurry of Streptavidin-coated, magnetic beads (Dynabeads MyOne Streptavidin T1) were washed with PBS and then loaded with 40 µg biotinylated GBP1 according to the manufacturers' instructions. Functionalized beads were equilibrated with IP buffer (0.5 mM EDTA, 50 mM Tris/Cl pH 7.0, 150 mM NaCl). Whole cell lysates were prepared using 200 µl lysis buffer (0.5 mM EDTA, 50 mM Tris/Cl pH 7.0, 150 mM NaCl, 1% NP40, 2 mM PMSF, 1× Mammalian Protease Inhibitor Cocktail. 5% of lysate supernatants were collected as input samples. The remaining sample was diluted to 1 ml using IP buffer and incubated with 50 µl bead slurry for 4 h. After magnetic pulldown, 5% supernatant were collected as flowthrough samples. For Coomassie staining and western blotting 2% input, 2% flowthrough and 20% bead fractions were boiled with Laemmli buffer at 95° C. and subjected to SDS-PAGE and transfer to a nitrocellulose membrane (Bio-Rad, USA). A monoclonal anti-GFP antibody (Roche, Switzerland) and HRP-conjugated anti-mouse IgG secondary antibody (Jackson ImmunoResearch, USA) was used for detection.

Example 23: Confocal Microscopy

Transfection. HeLa cells were seeded at sub-confluent concentration on glass coverslips (Carl Roth, Germany) the day before PEI transfection (Sigma-Aldrich, USA) with 2 µg pENeGFP-PCNA1. After transfection, cells were incubated for 18-24 h at 37° C., 5% CO2. Immunofluorescence. Cells were fixed in 3.7% formaldehyde in PBS for 10 min, permeabilized with 0.5% Triton X-100 (neoLab Migge Laborbedarf-Vertriebs, Germany) for 10 min, and blocked in 2% bovine serum albumin (Sigma-Aldrich, UK) for 60 min. For GFP labeling, cells were incubated for 60 min with GBP1-Tub-tag-Alexa594 (1:25 or 1:50) prior to extensive washing and DNA counterstain with 1 µg/mL DAPI for 10 min. All steps except fixation were carried out in PBS supplemented with 0.02% Tween 20 (PBST, Carl Roth, 9127.1) at room temperature. Glass coverslips were then mounted with anti-fade Mowiol mounting medium (Sigma-Aldrich, UK).

Confocal Microscopy and Image Analysis. Imaging was carried out with a Leica SP5 II confocal point scanner (Leica Microsystems, Germany) equipped with two HyD hybrid detectors. Image acquisition was performed with a ×60/1.4-0.6 NA Planapochromat oil immersion objective lens. To visualize DAPI, GFP and GBP1-Tub-tag-Alexa594, the 405, 488 and 561 nm excitation lasers were used, respectively. 16 bit images were collected and analyzed with Fiji2.

Example 24: Chemical Synthesis

Analytical HPLC was conducted on a SHIMADZU HPLC system (Shimadzu Corp., Japan) with a SIL-20A autosampler, 2 pumps LC2 AAT, a 2489 UV/Visible detector, a CTO-20A column oven and an RF-10 A X2 fluorescence detector using an Agilent Eclipse C18 5 µm, 250×4.6 mm RP-HPLC-column with a flow rate of 0.5 mL/min. The following gradient was used: Method A: (A=$H_2O$+0.1% TFA, B=MeCN+0.1% TFA) 35% B, 0-15 min, 10-100% B 15-17 min, 100% B 17-22 min, 100-35% B 22-25 min and 35% B 25-30 min. UV chromatograms were recorded at 220 nm and fluorescence spectra with Ex/Em 495/517 were recorded.

Analytical UPLC: UPLC-UV traces were obtained on a Waters H-class instrument equipped with a Quaternary Solvent Manager, a Waters autosampler and a Waters TUV detector connected to a 3100 mass detector with an Acquity UPLC-BEH C18 1.7 µm, 2.1×50 mm RP column with a flow rate of 0.6 mL/min (Water Corp., USA). The following gradient was used: Method B: (A=$H_2O$+0.1% TFA, B=MeCN+0.1% TFA) 5-95% B 0-3 min, 95% B 3-5 min. UPLC-UV chromatograms were recorded at 220 nm.

Preparative HPLC was performed on a Gilson PLC 2020 system (Gilson Inc., WI, Middleton, USA) using a Macherey-Nagel Nucleodur C18 HTec Spurn column (Macherey-Nagel GmbH & Co. Kg, Germany). The following gradient was used: Method C: (A=H2O+0.1% TFA, B=MeCN+0.1% TFA) flow rate 32 mL/min, 10% B 0-5 min, 10-100% B 5-35 min, 100% B 35-40 min. Method D: (A=H2O+0.1% TFA, B=MeCN+0.1% TFA) 10% B 0-5 min, 10-100% B 5-50 min, 100% B 50-55 min.

Analytical HPLC-MSMS: Peptides were analyzed by a Ultimate 3000 nanoLC system (Thermo Scientific, USA) connected to an LTQ Orbitrap XL mass spectrometer (Thermo Scientific, USA). LC separations were performed on a capillary column (Acclaim PepMap100, C18, 3 µm, 100 Å, 75 µm i.d.×25 cm, Thermo Scientific, USA) at an eluent flow rate of 300 nL/min. The following gradient was used: Method D: (A=$H_2O$+0.1% formic acid, B=MeCN+0.1% formic acid) 3-50% B 0-50 min Mass spectra were acquired in a data-dependent mode with one MS survey scan with a resolution of 30,000 (LTQ Orbitrap XL) or 60,000 (Orbitrap Elite) and MS/MS scans of the five most intense precursor ions in the linear trap quadrupole, respectively. Column chromatography was performed on silica gel (Acros Silica gel 60 Å, 0.035-0.070 mm). High resolution mass spectra (HRMS) were measured on an Acquity UPLC system and a LCT Premier™ (Waters Corp., USA) time-of-flight mass spectrometer with electrospray ionization using water and acetonitrile (10-90% gradient) with 0.1% formic acid as eluent. NMR spectra were recorded with a Bruker Ultrashield 300 MHz spectrometer (Bruker Corp., USA) at ambient temperature. The chemical shifts are reported in ppm relative to the residual solvent peak.

Product yields were calculated based on $^1$H-NMR spectra. TFA salt content was determined by $^{19}$F-NMR, tetrafluoroethylene as standard and considered in product yield calculation. Reagents and solvents were, unless stated otherwise, commercially available as reagent grade and did not require further purification. Resins and Fmoc-protected amino acids were purchased from IRIS BioTEch (Germany) or Novabiochem (Germany).

SPPS was either carried out manually or with an Activo-P11 automated peptide synthesizer (Activotec, UK) via standard Fmoc-based conditions (Fast-moc protocol with HOBt/HBUT conditions).

Example 25: Synthesis of 3-nitro-L-tyrosine (2), 3-amino-L-tyrosine (9) and 3-azido-L-tyrosine (3)

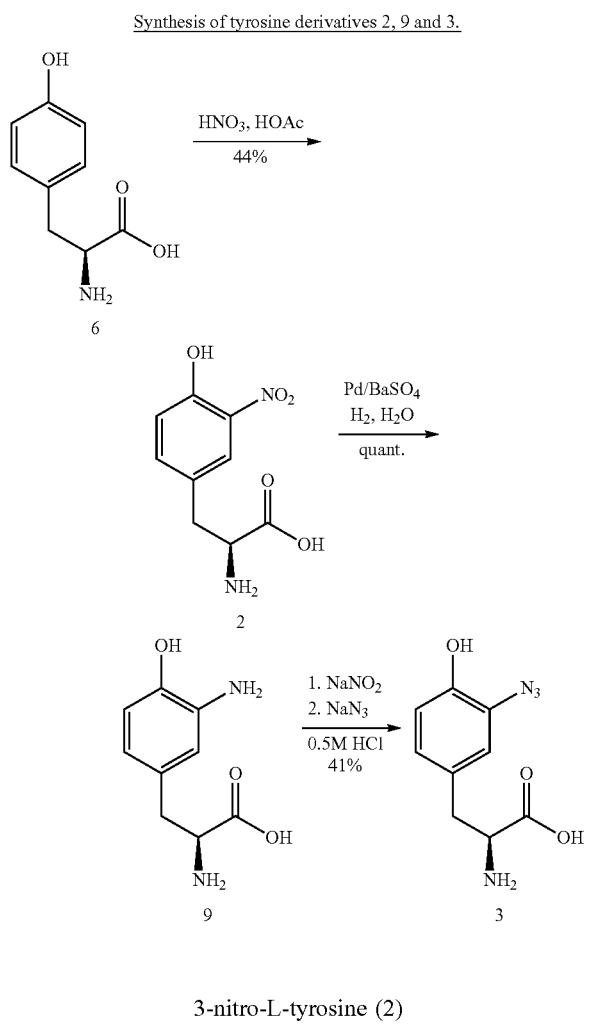

3-nitro-L-tyrosine (2)

L-tyrosine (6, 2.00 g, 11 mmol) was added to 10 mL HOAc, the suspension cooled to 0° C. and HNO3 (1.47 mL, 11 mmol, 7.5 N) was slowly added. After 4 h (when the starting material was dissolved completely) the reaction was diluted with H2O (2.5 mL) followed by neutralization with NH3 solution (25%). The resultant solution was filtrated, the filtrate lyophilized and subjected to HPLC purification (method C) to give compound 2 as TFA salt (1.38 g, 44%). Analytical data matched the literature (Seyedsayamdost, M. R., Argirevic, T., Minnihan, E. C., Stubbe, J. & Bennati, M. J. Am. Chem. Soc. 131, 15729-15738 (2009)).

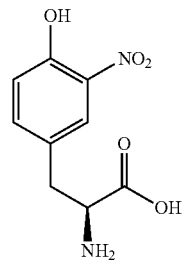

$^1$H-NMR (300 MHz, D2O): δ 7.89 (d, J=2.3 Hz, 1H, CH$_{phenyl}$), 7.43 (dd, J=8.7, 2.3 Hz, 1H, CH$_{phenyl}$), 7.03 (d, J=8.7 Hz, 1H, CH$_{phenyl}$), 4.18 (t, J=6.6 Hz, 1H, CH), 3.31-3.04 (m, 2H, CH2); $^{13}$C-NMR (75 MHz, D2O): δ 171.11, 152.74, 138.21, 133.85, 126.40, 125.76, 120.19, 53.68, 34.23; ESI-HRMS (m/z): [M]$^+$ calcd. for C$_9$H$_{12}$N$_2$O$_5$, 227.0660; found 227.0674.

3-amino-L-tyrosine (9)

Compound 2 (1.38 g, 4.86 mmol) was dissolved in H2O (100 mL) and conc. HCl (500 μL). The solution was supplemented with Pd/BaSO4 (40 mg, 5% catalyst loading) and the mixture incubated at ambient temperature for 12 h under H2 atmosphere. After filtration of the catalyst and removal of the solvent in vacuo, the product 9 was obtained in quantitative yield as TFA salt. Analytical data matched the literature (Seyedsayamdost, M. R., Argirevic, T., Minnihan, E. C., Stubbe, J. & Bennati, M. J. Am. Chem. Soc. 131, 15729-15738 (2009)).

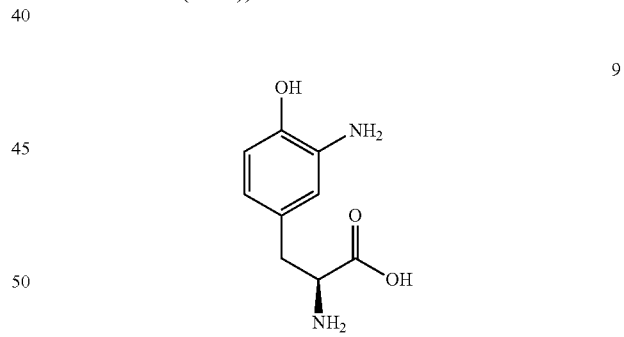

$^1$H-NMR (300 MHz, D2O): δ 7.42-7.15 (m, 2H, CH$_{phenyl}$) 7.05-6.89 (m, 1H, CH$_{phenyl}$), 4.11 (t, J=6.5 Hz, 1H, CH), 3.24-3.06 (m, 2H, CH2); $^{13}$C-NMR (75 MHz, D2O): δ=171.91, 149.37, 131.23, 126.32, 124.68, 117.84, 116.79, 54.47, 34.61; ESI-HRMS (m/z): [M]$^+$ calcd. for C$_9$H$_{13}$N$_2$O$_3$, 197.0918; found 197.0910.

3-azido-L-tyrosine (3)

3-amino-L-tyrosine (9, 0.696 g, 3.21 mmol) was dissolved in 0.5 M HCl (6 mL) and a solution of NaNO2 (0.221 g, 3.21 mmol) in ice-cold H2O (1 mL) was slowly added at 0° C. After 20 min, a solution of NaN3 (0.560 g, 8.62 mmol) in H2O (3 mL) was added within 30 min and stirred at 0° C.

for another 8 h. The grey precipitate was isolated and purified by preparative HPLC (method C) to give pure compound 3 (0.290 g, 41%).

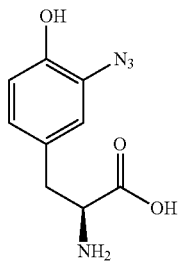

3

¹H-NMR (300 MHz, D₂O): δ 6.95 (d, J=2.0 Hz, 1H, CH$_{phenyl}$), 6.89-6.79 (m, 2H, CH$_{phenyl}$), 4.06 (t, J=6.5 Hz, 1H, CH), 3.19-2.95 (m, 2H, CH2); ¹³C-NMR (75 MHz, D2O): δ 172.04, 146.44, 127.24, 127.07, 126.58, 120.38, 116.86, 54.51, 34.83; ESI-HRMS (m/z): [M]⁺ calcd. for C₉H₁₁N₄O₃, 223.0823; found 223.0830.

Example 26: Synthesis of 3-formyl-L-tyrosine (1)

The synthesis of 1 was performed according to a known procedure in literature (Jung, M. E. & Lazarova, T. I. J. Org. Chem. 62, 1553-1555 (1997); Banerjee, A. et al. ACS Chem. Biol. 5, 777-785 (2010)).

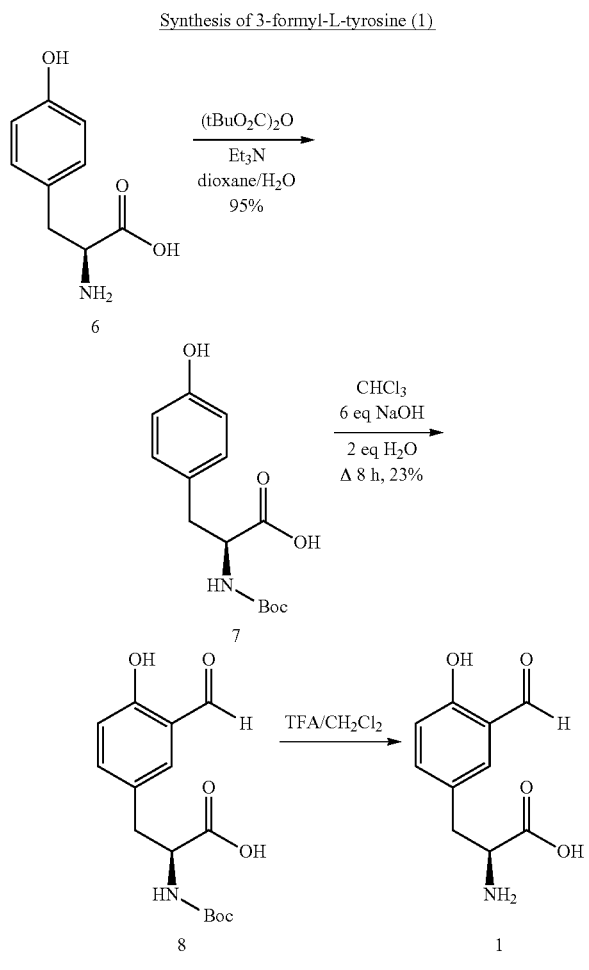

N-[(1,1-dimethylethoxy)carbonyl]-L-tyrosine (7)

To a solution of L-tyrosine (6, 1 g, 5.5 mmol) in 1/1 dioxane/water (50 mL), triethylamine (1.16 mL, 8.28 mmol) was slowly added. The reaction was cooled to 0° C. with an ice/water bath and di-tert-butyl dicarbonate (1.32 g, 6.07 mmol) was added in two steps. After 1 h at 0° C., the temperature was slowly increased to ambient temperature and the mixture was stirred for further 24 h. Dioxane was removed under reduced pressure and the aqueous solution mixed with saturated NaHCO₃ (25 mL), washed with ethyl acetate, acidified to pH 1 with 1 N HCl, extracted with ethyl acetate and the organic extracts were washed with brine, dried over MgSO₄ and evaporated to give Boc protected tyrosine 7 as a white foam (1.471 g, 95%) which was used in the next step without further purification. Analytical data matched the literature (Jung, M. E. & Lazarova, T. I. J. Org. Chem. 62, 1553-1555 (1997)).

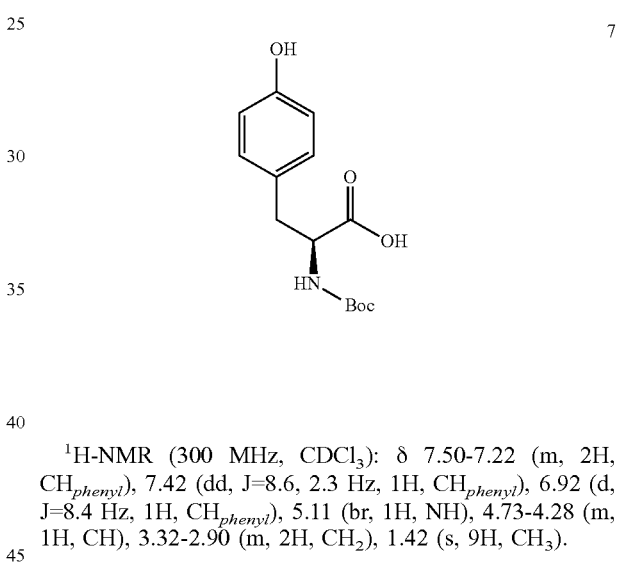

¹H-NMR (300 MHz, CDCl₃): δ 7.50-7.22 (m, 2H, CH$_{phenyl}$), 7.42 (dd, J=8.6, 2.3 Hz, 1H, CH$_{phenyl}$), 6.92 (d, J=8.4 Hz, 1H, CH$_{phenyl}$), 5.11 (br, 1H, NH), 4.73-4.28 (m, 1H, CH), 3.32-2.90 (m, 2H, CH₂), 1.42 (s, 9H, CH₃).

N-[(1,1-dimethylethoxy)carbonyl]-3-(3-formyl-4-hydroxyphenyl)-L-alanine (8)

To a suspension of 7 (2.00 g, 7.12 mmol) in chloroform (30 mL) and H₂O (0.256 mL, 14.13 mmol) powdered sodium hydroxide (1.71 g, 42.72 mmol) was added and the mixture was refluxed for 4 h. Two additional portions of powdered sodium hydroxide (each 0.42 g, 10.68 mmol) were added after 1 and 2 h. After 8 h at reflux, the reaction was cooled to ambient temperature, diluted with water and ethyl acetate (15 mL each), the organic layer discharged, the aqueous layer acidified to pH 1 with 1 N HCl and back-extracted with ethyl acetate. The organic layers were washed with brine, dried over MgSO₄ and concentrated. Flash column chromatography (silica gel, 12/1 CHCl₃/MeOH, 1% acetic acid) gave compound 8 (0.49 g, 23%). Analytical data matched the literature (Jung, M. E. & Lazarova, T. I. J. Org. Chem. 62, 1553-1555 (1997)).

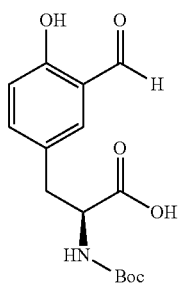

¹H-NMR (300 MHz, CDCl₃): δ 9.85 (s, 1H, CHO), 7.49-7.21 (m, 2H, CH$_{phenyl}$) 7.40 (dd, J=8.6, 2.3 Hz, 1H, CH$_{phenyl}$), 6.94 (d, J=8.4 Hz, 1H, CH$_{phenyl}$), 5.10 (br, 1H, NH), 4.73-4.27 (m, 1H, CH), 3.30-2.89 (m, 2H, CH₂), 1.40 (s, 9H, CH₃).

3-formyl-L-tyrosine (1)

Compound 8 (0.49 g, 1.6 mmol) was dissolved in CH₂Cl₂. TFA (4 mL) was added slowly at 0° C. and the mixture was warmed to ambient temperature within 2 h. The solvent was removed at high vacuum. Preparative HPLC (method C) gave compound 1 as TFA salt (0.29 g, 80%). Analytical data matched the literature (Jung, M. E. & Lazarova, T. I. J. Org. Chem. 62, 1553-1555 (1997)).

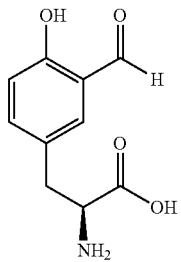

¹H-NMR (300 MHz, D₂O): δ 9.81 (s, 1H, CHO), 7.52 (d, J=2.4 Hz, 1H, CH$_{phenyl}$), 7.40 (dd, J=8.6, 2.3 Hz, 1H, CH$_{phenyl}$), 6.90 (d, J=8.6 Hz, 1H, CH) 4.13 (t, J=6.6 Hz, 1H, CH), 3.15 (m, 2H, CH₂); ¹³C-NMR (75 MHz, D₂O): δ 197.18, 171.68, 159.21, 138.07, 134.02, 126.03, 120.97, 117.73, 54.18, 34.48; ESI-HRMS (m/z): [M]⁺ calcd. for C₁₀H₁₂NO₄, 210.0758; found 210.0760.

Example 27: Synthesis of tris(PEG750)phosphite 14

14 was synthesized based on a protocol by Nischan et al (Angew. Chem. Int. Ed. 52, 11920-11924 (2013)). Polyethylene glycomethylether was carefully dried at 70° C. under high vacuum. Hexamethylphosphortriamide (1 eq., 0.135 mmol, 24.5 µL) was added to dry polyethylene glycomethylether (3 eq., 0.406 mmol, 0.314 g) at 110° C. and stirred under N2 stream for 72 h. The product was recovered as a white paraffinic solid (0.133 mmol, 0.311 g). In order to avoid hydrolysis of the product, no purification was done. Due to the chemoselective character of the Staudinger-phosphite reaction, impurities do not interfere in the reaction and can be removed easily after the Staudinger-phosphite reaction.

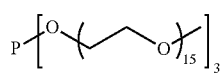

¹H-NMR (400 MHz, [D]-acetonitrile): δ 3.58-3.57 (m, 198.9H, OCH₂CH₂O—), 3.32 (s, 9H, OCH₃); ³¹P-NMR (400 MHz, [D]-acetonitrile): δ 140.

Example 28: Synthesis of hydroxylamine-biotin S2

Synthesis of hydroxylamine biotin 15

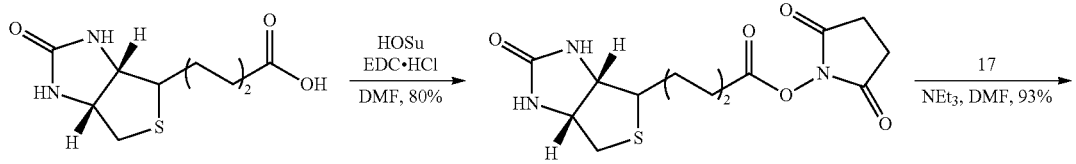

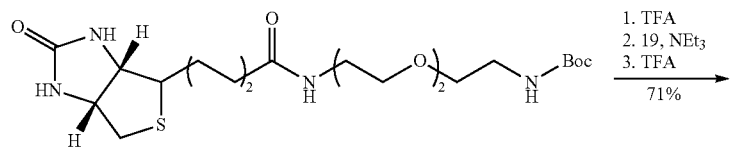

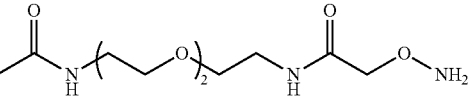

15

D-biotin N-hydroxysuccinimide ester (16)

1-ethyl-3-(3-dimethylaminopropyl)carbodiimid (184 mg, 0.96 mmol) was added to a solution of D-biotin (200 mg, 0.82 mmol) and N-hydroxysuccinimid (102 mg, 0.89 mmol) in dry DMF (10 mL). The solution was stirred for 12 h at ambient temperature, concentrated and the product crystallized from 2-propanol to give succinimide ester 16 (261 mg, 80). The product was used without further purification and analytical data are in accordance with those reported in the literature (Gerard, E., Meulle, A., Feron, O. & Marchand-Brynaert, J. Bioorg. Med. Chem. Lett. 22, 586-590 (2012)).

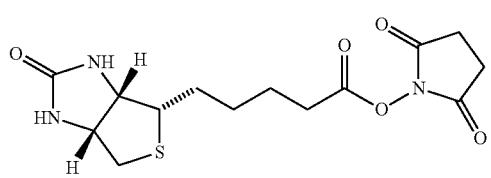

16

$^1$H-NMR (300 MHz, DMSO): δ 6.41 (s, 1H, NH), 6.36 (s, 1H, NH), 4.35-4.26 (m, 1H, CH), 4.18-4.11 (m, 1H, CH), 3.14-3.05 (m, 1H, CH), 2.89-2.75 (m, 5H, 2×CH$_2$, CH), 2.64 (t J=7.4 Hz, 2H, CH$_2$), 2.60-2.55 (m, 1H, 3.32, CH), 1.72-1.32 (m, 6H, 3×CH$_2$).

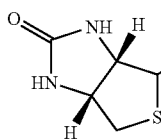

17

$^1$H-NMR (300 MHz, CDCl$_3$): δ 5.17 (br, 1H, NHBoc), 3.63 (s, 4H, OCH$_2$CH$_2$O), 3.56-3.47 (m, 4H, CH$_2$O), 3.35-3.23 (m, 2H, CH$_2$NHBoc), 2.86 (t, J=5.2 Hz, 2H, CH$_2$NH$_2$), 1.51 (s, 2H, NH$_2$), 1.42 (s, 9H, CH$_3$); $^{13}$C-NMR (75 MHz, CDCl$_3$): δ 155.90, 79.03, 73.27, 70.08, 41.61, 40.21, 28.30.

N-Boc-N'-D-biotinyl-3,6-dioxaoctane,1,8-diamine (18)

To a solution of Boc-diamine 17 (109 mg, 0.44 mmol) and NEt$_3$ (81 μL, 0.59 mmol) in dry DMF (5 mL), D-biotin N-hydroxysuccinimide ester (16, 100 mg, 0.29 mmol) was added and stirred for 12 h. The solvent was removed, the residue resolved in CH$_2$Cl$_2$ (40 mL), washed with 20 mL brine, dried over MgSO$_4$ and concentrated. Flash column chromatography (silica gel, CH$_2$Cl$_2$/MeOH: 99/1→93/7) gave compound 18 (0.128 g, 93%). Analytical data matched the literature (Braun, M. et al. Eur. J. Org. Chem., 1173-1181 (2000)).

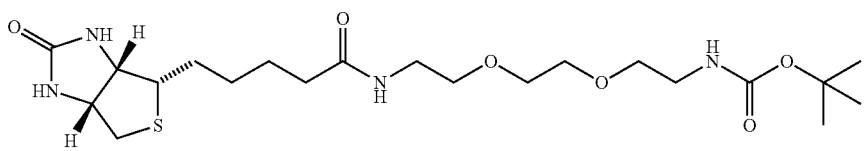

18

2-Amino-3'[(tert-butoxycarbonyl)amino]ethylene glycol diethyl ether (17)

To a solution of 2,2'-(ethylenedioxy)-bis(ethylamine) (4.07 g, 27.46 mmol) and N,N-Diisopropylethylamine (1.56 mL, 9.17 mmol) in dry CH$_2$Cl$_2$ (50 mL) at ambient temperature a solution of di-tert-butyl dicarbonate (2.0 g, 9.16 mmol) in dry CH$_2$Cl$_2$ (20 mL) was added dropwise within 20 min. After additional stirring for 1 h at ambient temperature, the mixture was concentrated, redissolved in 20 mL water and extracted four times with CH$_2$Cl$_2$ (10 mL). The organic layers were combined, washed three times with brine, dried with MgSO$_4$ and concentrated to give 2.02 g of a colorless oil of 17 in an overall yield of 88.8% containing some impurities of double protected species (20% determined from $^1$H-NMR). The analytical data are in accordance with those reported in the literature (Ishida, M. et al. J. Am. Chem. Soc. 135, 12684-12689 (2013)).

TLC (CH$_2$Cl$_2$:MeOH, 90:10 v/v): R$_f$ =0.37; $^1$H-NMR (300 MHz, CDCl$_3$): δ 7.35-7.23 (br, 1H. CONH), 6.77-6.19 (br, 2H, NH), 5.24-5.04 (br, 1H, CONH), 4.59-4.48 (m, 1H, CH), 4.40-4.28 (m, 1H, CH), 3.63 (s, 4H, OCH$_2$CH$_2$O), 3.58 (dt, J$_1$=J$_2$=5.4 Hz, 4H, CH$_2$O), 3.46 (dt, J$_1$=J$_2$=4.9 Hz, 2H, CH$_2$NH), 3.32 (dt, J$_1$=J$_2$=5.4 Hz, 2H, CH$_2$NHboc), 3.22-3.12 (m, 1H, CH), 2.98-2.89 (m, 1H, CHH$_{exo}$S), 2.76 (d, J=12.8 Hz, 1H, CHH$_{endo}$S), 2.26 (t, J=7.4 Hz, 2H, CH$_2$CO), 1.82-1.61 (m, 4H, CH$_2$), 1.46 (s, 9H, CH$_3$), 1.26 (m, 2H, CH$_2$); $^{13}$C-NMR (75 MHz, CDCl$_3$): δ 173.52, 165.20, 156.94, 79.10, 70.03 (4C), 61.78, 60.30, 55.30, 40.55, 40.31, 39.13, 35.64, 29.61, 28.35 (3C) 27.96, 25.46.

N'-Boc-aminooxyacetyl-N-hydroxysuccinimide ester (19)

1-ethyl-3-(3-dimethylaminopropyl)carbodiimid (227 mg, 1.8 mmol) and N-hydroxysuccinimide (190 mg, 1.65 mmol) was added to a solution of N-Boc-aminooxyacetic acid (287 mg, 1.5 mmol) in dry DMF (10 mL) and stirred at ambient temperature for 12 h. The mixture was diluted by the addition of H2O (10 mL), extracted twice with EtOAc, the organic phase dried over MgSO4 and concentrated under vacuum. The yellowish liquid was used without further purification (352 mg, 81%). Analytical data matched the literature (Palaniappan, K. K. et al. Angew. Chem. Int. Ed. 52, 4849-4853 (2013)).

chromatography (silica gel, $CH_2Cl_2$:MeOH, 99:1 to 93:7) gave boc protected hydroxylamine S2 (TLC=[$CH_2Cl_2$: MeOH, 90:10 v/v]: $R_f$=0.3). A final deprotection in 25% TFA solution ($CH_2Cl_2$) followed by TFA removal gave deprotected hydroxylamine 15 (102.2 mg, 71%).

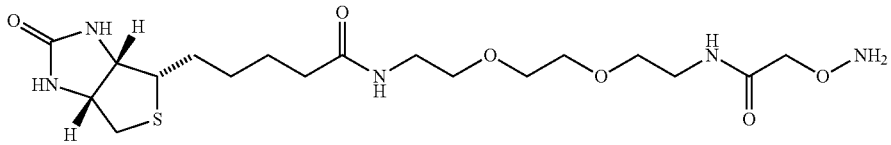

15

$^1$H-NMR (300 MHz, D2O): δ 4.50 (s, 2H, COCH2O), 4.49-4.43 (m, 1H, CH), 4.24-4.31 (m, 1H, CH), 3.54 (s, 4H, $OCH_2CH_2O$), 3.52-3.45 (m, 4H, $CH_2O$), 3.33 (dt, $J_1=J_2$=5.3 Hz, 2H, $CH_2NH$), 3.24 (dt, $J_1=J_2$=5.4 Hz, 2H, $CH_2NHboc$), 3.21-3.14 (m, 1H, CH), 2.85 (dd, $J_1$=13, $J_2$=4.9, Hz 1H, $CHH_{exo}S$), 2.62 (d, J=13 Hz, 1H, $CHH_{endo}S$), 2.13 (t, J=7.2 Hz, 2H, $CH_2CO$), 1.65-1.36 (m, 4H, $CH_2$), 1.32-1.20 (m, 2H, $CH_2$); $^{13}$C-NMR (151 MHz, $D_2O$) δ 176.79, 168.56, 165.14, 71.52, 69.26, 69.23, 68.70, 68.44, 61.93, 60.09, 55.20, 39.52, 38.67, 38.50, 35.26, 27.68, 27.52, 24.97; ESI-MS (m/z): [M]$^+$ calcd. for $C_{18}H_{34}N_5O_6S$, 448.22; found 448.21.

Example 29: Synthesis of CF-Tub-Tag Peptide 13

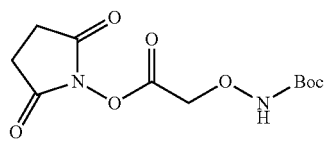

19

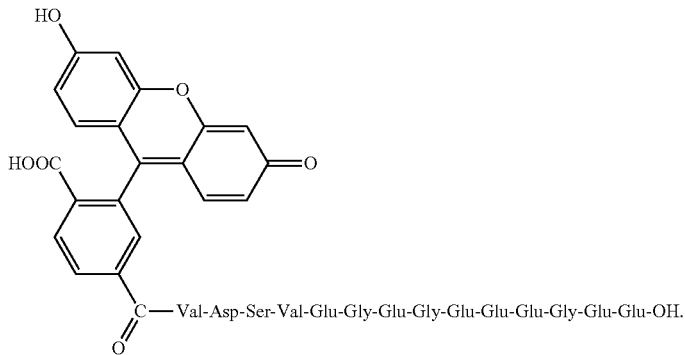

13

5(6)-carboxyfluorescein labeled Tub-tag peptide 13

$^1$H-NMR (300 MHz, $CDCl_3$): δ 7.84 (s, 1H, NH), 4.61 (s, 2H, $CH_2$), 2.82 (s, 4H, 2×$CH_2$), 1.31 (s, 9H, $CH_3$); $^{13}$C-NMR (151 MHz, $CDCl_3$) δ 164.83, 162.92, 156.41, 82.17, 70.48, 27.88, 25.39.

N-aminooxyacetyl-N'-D-biotinyl-3,6-dioxaoctane,1,8-diamine (15)

Boc protected diamine 18 (127 mg, 0.32 mmol) was dissolved in $CH_2Cl_2$ (4 mL), TFA (1 mL) was added and the solution stirred at ambient temperature for 2 h. TFA was removed and the remaining solid was dried using high vacuum. The deprotected diamine was dissolved in a mixture of dry DMF (3 mL) and $NEt_3$ (89 µL, 0.64 mmol). Hydroxysuccinimide ester 19 (152 mg, 0.52 mmol) was dissolved in dry DMF (0.5 mL), slowly added to the diamine and the resulting mixture was stirred at ambient temperature for 12 h. The solvent was removed and flash column CF-Tub-tag peptide was synthesized by standard Fmoc-based chemistry in a linear synthesis on an Activotec peptide synthesizer followed by manual coupling of 5(6)-carboxyfluorescein.

0.1 mmol of Fmoc-L-Glu(tBu)-Wang resin (subst: 0.58 mmol/g) was added to a reaction vessel and synthesis was performed with five fold amino acid excess. Coupling was achieved by HOBt/HBTU/DIPEA addition. After the final amino acid coupling, the fluorophore was coupled in a double coupling procedure with 5 eq of 5(6)-carboxyfluorescein, HOBt, HBTU and DIPEA in DMF for 1 h. The peptide was cleaved off the resin by addition of TFA/DTT/Tis/thioanisol (95/2/2/1) within 4 h. Subsequently, the cleavage cocktail was evaporated by N2-flow and the peptide was precipitated by the addition of ice cold diethyl ether. The precipitate was spun down, dissolved in water and purified by preparative HPLC (method D). The peptide was obtained with a yield of 8% (16 mg, 8 μmol); molar mass peptide=1850.6 Da; ESI-HRMS (m/z): [M+2H]$^{2+}$ calcd. 926.3165; found 926.3065.

Example 30: LC-UV at 220 nm, 10 to 100% of Acetonitrile in Water Containing 0.1% TFA on a RP-C18 Column See FIG. 28

REFERENCES

1 Keppler, A. et al. A general method for the covalent labeling of fusion proteins with small molecules in vivo. Nature Biotechnology 21, 86-89, doi:10.1038/nbt765 (2003).
2 Los, G. V. et al. HaloTag: a novel protein labeling technology for cell imaging and protein analysis. Acs Chem Biol 3, 373-382, doi:10.1021/cb800025k (2008).
3 Schumacher, D. & Hackenberger, C. P. More than add-on: chemoselective reactions for the synthesis of functional peptides and proteins. Current opinion in chemical biology 22, 62-69, doi:10.1016/j.cbpa.2014.09.018 (2014).
4 Hackenberger, C. P. & Schwarzer, D. Chemoselective ligation and modification strategies for peptides and proteins. Angewandte Chemie International Edition 47, 10030-10074, doi:10.1002/anie.200801313 (2008).
5 Liebscher, S. et al. N-terminal protein modification by substrate-activated reverse proteolysis. Angewandte Chemie International Edition 53, 3024-3028, doi:10.1002/anie.201307736 (2014).
6 Mao, H., Hart, S. A., Schink, A. & Pollok, B. A. Sortase-mediated protein ligation: a new method for protein engineering. Journal of the American Chemical Society 126, 2670-2671, doi:10.1021/ja039915e (2004).
7 Yin, J. et al. Genetically encoded short peptide tag for versatile protein labeling by Sfp phosphopantetheinyl transferase. Proceedings of the National Academy of Sciences of the United States of America 102, 15815-15820, doi:10.1073/pnas.0507705102 (2005).
8 Chen, I., Howarth, M., Lin, W. & Ting, A. Y. Site-specific labeling of cell surface proteins with biophysical probes using biotin ligase. Nature methods 2, 99-104, doi: 10.1038/nmeth735 (2005).
9 Fernandez-Suarez, M. et al. Redirecting lipoic acid ligase for cell surface protein labeling with small-molecule probes. Nature Biotechnology 25, 1483-1487, doi: 10.1038/nbt1355 (2007).
10 Wu, P. et al. Site-specific chemical modification of recombinant proteins produced in mammalian cells by using the genetically encoded aldehyde tag. Proceedings of the National Academy of Sciences of the United States of America 106, 3000-3005, doi:10.1073/pnas.0807820106 (2009).
11 Rudiger, M., Wehland, J. & Weber, K. The carboxy-terminal peptide of detyrosinated alpha tubulin provides a minimal system to study the substrate specificity of tubulin-tyrosine ligase. European journal of biochemistry/FEBS 220, 309-320 (1994).
12 Szyk, A., Deaconescu, A. M., Piszczek, G. & Roll-Mecak, A. Tubulin tyrosine ligase structure reveals adaptation of an ancient fold to bind and modify tubulin. Nature structural & molecular biology 18, 1250-1258, doi:10.1038/nsmb.2148 (2011).
13 Banerjee, A. et al. Site-specific orthogonal labeling of the carboxy terminus of alpha-tubulin. ACS chemical biology 5, 777-785, doi:10.1021/cb100060v (2010).
14 Hamers-Casterman, C. et al. Naturally occurring antibodies devoid of light chains. Nature 363, 446-448, doi:10.1038/363446a0 (1993).
15 Trinkle-Mulcahy, L. et al. Identifying specific protein interaction partners using quantitative mass spectrometry and bead proteomes. J Cell Biol 183, 223-239, doi:DOI 10.1083/jcb.200805092 (2008).
16 Rothbauer, U. et al. Targeting and tracing antigens in live cells with fluorescent nanobodies. Nature Methods 3, 887-889, doi:Doi 10.1038/Nmeth953 (2006).
17 Kirchhofer, A. et al. Modulation of protein properties in living cells using nanobodies. Nat Struct Mol Biol 17, 133-138, doi:10.1038/nsmb.1727 (2010).
18 Agard, N. J., Prescher, J. A. & Bertozzi, C. R. A strain-promoted [3+2] azide-alkyne cycloaddition for covalent modification of biomolecules in living systems. Journal of the American Chemical Society 126, 15046-15047, doi:10.1021/ja044996f (2004).
19 Saxon, E. & Bertozzi, C. R. Cell surface engineering by a modified Staudinger reaction. Science 287, 2007-2010 (2000).
20 Serwa, R. et al. Site-specific PEGylation of proteins by a Staudinger-phosphite reaction. Chem Sci 1, 596-602, doi:Doi 10.1039/C0sc00324g (2010). 12
21 Sletten, E. M. & Bertozzi, C. R. Bioorthogonal chemistry: fishing for selectivity in a sea of functionality. Angewandte Chemie International Edition 48, 6974-6998, doi:10.1002/anie.200900942 (2009).
22 Guizetti, J. et al. Cortical constriction during abscission involves helices of ESCRT-III-dependent filaments. Science 331, 1616-1620, doi:science.1201847 [pii] 10.1126/science.1201847 (2011).
23 Ries, J., Kaplan, C., Platonova, E., Eghlidi, H. & Ewers, H. A simple, versatile method for GFP-based super-resolution microscopy via nanobodies. Nat Methods 9, 582-584, doi:nmeth.1991 [pii] 10.1038/nmeth.1991 (2012).
24 Zink, S. et al. Tubulin detyrosination promotes monolayer formation and apical trafficking in epithelial cells. J Cell Sci 125, 5998-6008, doi:10.1242/jcs.109470 (2012).

The invention claimed is:

1. A method for the production of a polypeptide comprising
    (a) introducing or adding at the C-terminus of a polypeptide a recognition sequence for tubulin tyrosine ligase; and
    (b) contacting the polypeptide obtained in step (a) in the presence of tubulin tyrosine ligase and a tyrosine derivative under conditions suitable for the tubulin tyrosine ligase to tyrosinate said polypeptide with said tyrosine derivative.

2. The method of claim 1, further comprising
    (c) conjugating a moiety to said tyrosinated polypeptide obtained in step (b).

3. A method for the production of a polypeptide comprising
    (a') introducing or adding at the C-terminus of a polypeptide a recognition sequence for tubulin tyrosine ligase; and
    (b') contacting the polypeptide obtained in step (a') in the presence of tubulin tyrosine ligase and a tyrosine derivative conjugated to a moiety under conditions suitable for the tubulin tyrosine ligase to tyrosinate said polypeptide with said tyrosine derivative conjugated to said moiety.

4. The method of claim 1, wherein the recognition sequence for tubulin tyrosine ligase has at least the amino acid sequence $X_1X_2X_3X_4$ (SEQ ID No: 11), wherein $X_1$ and $X_2$ is any amino acid, $X_3$ is E, D or C and $X_4$ is E.

5. The method of claim 1, wherein $X_2$ is G, S, A, V, or F.

6. The method of claim 1, wherein $X_1$ is E, D, A, K, or P.

7. The method of claim 1, wherein the recognition sequence is EGEE (SEQ ID No. 2).

8. The method of claim 1, wherein the recognition sequence is VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

9. The method of claim 1, wherein said polypeptide comprises a linker sequence preceding the recognition sequence for the tubulin tyrosine ligase added in step (a).

10. The method of claim 1, wherein said moiety conjugated to a tyrosinated polypeptide is a carrier, a polypeptide, a detectable label, a chemical compound, a nucleic acid, a carbohydrate, or a lipid.

11. The method of claim 10, wherein the polypeptide is an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer.

12. The method of claim 10, wherein the detectable label comprises a fluorophore, an enzyme (peroxidase, luciferase), a radioisotope, a fluorescent protein, or a fluorescent dye.

13. The method of claim 10, wherein said chemical compound is a small molecule, a polymer, or a therapeutic agent.

14. The method of claim 10, wherein the nucleic acid is DNA, RNA, or an aptamer.

15. The method of claim 1, wherein the suitable conditions comprise a buffer containing a nucleoside triphosphate, such as ATP, potassium chloride, magnesium chloride, a reducing agent such as DTT.

16. The method of claim 1, wherein the suitable conditions further comprise a pH-value in the range of 5 to 9.

17. The method of claim 1, wherein the suitable conditions further comprise a tyrosine derivative concentration in the range of 0.1 mM to 10 mM.

18. The method of claim 1, wherein the suitable conditions further comprise a reaction temperature in the range of 1° C. to 70° C. or 19° C. to 37° C.

19. The method of claim 1, wherein the suitable conditions further comprise a reaction time in the range of 5 minutes to 4 hours or 1 hour to 3 hours.

20. The method of claim 1, wherein said tyrosine derivative contains an unnatural functional group for chemoselective or bioorthogonal modifications.

21. The method of claim 20, wherein the unnatural functional group is selected from the group consisting of terminal alkyne, azide, strained alkyne, diene, dienophile, alkoxyamine, carbonyl, phosphine, phosphonite, phosphite, hydrazide, thiol, tetrazine, alkene, cyclooctyne, electron-withdrawing substitutents, phenol-derivatives, nitriles (CN), carbonyls (CO), or nitro groups ($NO_2$).

22. The method of claim 1, wherein said tyrosine derivative is a 2, substituted, 3-substituted or 4-substituted tyrosine or a tyrosine derivative substituted at the benzylic position.

23. The method of claim 22, wherein said 3- or 4-substituted tyrosine derivative is 3-nitrotyrosine, 3-aminotyrosine, 3-azidotyrosine, 3-formyltyrosine, 3-acetyltyrosine, or 4-aminophenylalanine.

24. The method of claim 1, wherein said polypeptide has a length of more than 19 amino acids.

25. The method of claim 1, wherein said polypeptide is a polypeptide other than tubulin.

26. A method for installing a click chemistry handle to the C-terminus of a polypeptide other than tubulin, comprising:
    (a) providing a polypeptide having at its C-terminus a tubulin tyrosine ligase recognition sequence; and
    (b) contacting the polypeptide of step (a) in the presence of tubulin tyrosine ligase and a tyrosine derivative containing an unnatural functional group for chemoselective or bioorthogonal modifications under conditions suitable for the tubulin tyrosine ligase to tyrosinate said polypeptide with said tyrosine derivative.

27. The method of claim 26, optionally further comprising conjugating a moiety selected from a carrier, a polypeptide, a detectable label, a chemical compound, a nucleic acid, a carbohydrate, or a lipid to said tyrosinated polypeptide obtained in step (b).

28. The method of claim 13, wherein the synthetic polymer is PEG.

29. The method of claim 26 wherein said unnatural functional group is selected from the group consisting of terminal alkyne, azide, strained alkyne, diene, dienophile, alkoxyamine, carbonyl, phosphine, phosphonite, phosphite, hydrazide, thiol, tetrazine, alkene, cyclooctyne, F, Br, Cl, I, phenol-derivatives, nitriles, carbonyls, or nitro groups.

30. The method of claim 21, wherein the electron-withdrawing substituent is a halogen.

31. The method of claim 30, wherein the halogen is F, Br, Cl or I.

* * * * *